United States Patent
Lee et al.

(10) Patent No.: US 10,344,068 B2
(45) Date of Patent: Jul. 9, 2019

(54) NATRIURETIC POLYPEPTIDES

(71) Applicant: Mayo Foundation for Medical Education and Research, Rochester, MN (US)

(72) Inventors: Candace Y. W. Lee, Dollard-des-Ormeaux (CA); John C. Burnett, Jr., Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/411,630

(22) Filed: Jan. 20, 2017

(65) Prior Publication Data

US 2017/0129934 A1 May 11, 2017

Related U.S. Application Data

(63) Continuation of application No. 15/232,429, filed on Aug. 9, 2016, now Pat. No. 9,587,004, which is a continuation of application No. 14/791,047, filed on Jul. 2, 2015, now Pat. No. 9,441,027, which is a continuation of application No. 14/003,481, filed as application No. PCT/US2012/051734 on Aug. 21, 2012, now Pat. No. 9,102,707.

(60) Provisional application No. 61/648,718, filed on May 18, 2012, provisional application No. 61/529,113, filed on Aug. 30, 2011.

(51) Int. Cl.

| C07K 7/08  | (2006.01) |
| A61K 38/00 | (2006.01) |
| A61K 38/17 | (2006.01) |
| A61K 38/22 | (2006.01) |
| C07K 14/47 | (2006.01) |
| C07K 14/58 | (2006.01) |

(52) U.S. Cl.
CPC .............. *C07K 14/58* (2013.01); *A61K 38/00* (2013.01); *A61K 38/1709* (2013.01); *A61K 38/2242* (2013.01); *C07K 7/08* (2013.01); *C07K 14/47* (2013.01)

(58) Field of Classification Search
None
See application file for complete search history.

(56) References Cited

U.S. PATENT DOCUMENTS

| 3,842,067 A | 10/1974 | Sarantakis |
| 3,862,925 A | 1/1975 | Sarantakis et al. |
| 3,972,859 A | 8/1976 | Fujino et al. |
| 4,034,074 A | 7/1977 | Miles |
| 4,051,842 A | 10/1977 | Hazel et al. |
| 4,098,876 A | 7/1978 | Piasio et al. |
| 4,105,602 A | 8/1978 | Colescott et al. |
| 4,140,122 A | 2/1979 | Kuhl et al. |
| 4,161,521 A | 7/1979 | Veber et al. |
| 4,233,402 A | 11/1980 | Maggio et al. |
| 4,383,529 A | 5/1983 | Webster |
| 4,496,544 A | 1/1985 | Needleman |
| 4,683,195 A | 7/1987 | Mullis et al. |
| 4,728,721 A | 3/1988 | Yamamoto et al. |
| 4,749,688 A | 6/1988 | Haslanger et al. |
| 4,757,048 A | 7/1988 | Lewicki et al. |
| 4,804,650 A | 2/1989 | Lewicki et al. |
| 4,935,492 A | 6/1990 | Lewicki et al. |
| 4,938,763 A | 7/1990 | Dunn et al. |
| 4,996,143 A | 2/1991 | Heller et al. |
| 5,047,397 A | 9/1991 | Scarborough et al. |
| 5,114,923 A | 5/1992 | Seilhamer et al. |
| 5,202,239 A | 4/1993 | Tarnowski et al. |
| 5,212,286 A | 5/1993 | Lewicki et al. |
| 5,226,325 A | 7/1993 | Komurasaki et al. |
| 5,278,201 A | 1/1994 | Dunn et al. |
| 5,278,202 A | 1/1994 | Dunn et al. |
| 5,296,347 A | 3/1994 | Lamotte, III |
| 5,322,930 A | 6/1994 | Tarnowski et al. |
| 5,410,016 A | 4/1995 | Hubbell et al. |
| 5,434,133 A | 7/1995 | Tanaka et al. |
| 5,449,662 A | 9/1995 | Scarborough |
| 5,449,751 A | 9/1995 | Forssmann et al. |
| 5,501,863 A | 3/1996 | Rossling et al. |
| 5,529,914 A | 6/1996 | Hubbell et al. |
| 5,560,922 A | 10/1996 | Chien et al. |
| 5,565,322 A | 10/1996 | Heller |
| 5,580,859 A | 12/1996 | Felgner et al. |
| 5,583,108 A | 12/1996 | Wei et al. |

(Continued)

FOREIGN PATENT DOCUMENTS

| EP | 0045665 | 9/1985 |
| EP | 0533084 | 3/1993 |

(Continued)

OTHER PUBLICATIONS

US 6,884,780 B2, 04/2005, Drummond et al. (withdrawn)

(Continued)

*Primary Examiner* — James H Alstrum-Acevedo
*Assistant Examiner* — Tara L Martinez
(74) *Attorney, Agent, or Firm* — Fish & Richardson P.C.

(57) ABSTRACT

This document provides methods and materials related to natriuretic polypeptides and the use of natriuretic polypeptides to treat cardiovascular and/or renal conditions. For example, chimeric polypeptides having at least one amino acid segment (e.g., N-terminus tail, ring structure, C-terminus tail, or a combination thereof) of a natriuretic peptide (e.g., ANP, BNP, CNP, URO, or DNP) and an amino acid segment of an angiotensin polypeptide (e.g., Ang-(1-7)) are provided.

13 Claims, 26 Drawing Sheets

Specification includes a Sequence Listing.

(56) References Cited

U.S. PATENT DOCUMENTS

| | | |
|---|---|---|
| 5,589,466 A | 12/1996 | Feigner et al. |
| 5,665,704 A | 9/1997 | Lowe et al. |
| 5,674,710 A | 10/1997 | Seilhamer et al. |
| 5,691,310 A | 11/1997 | Vesely |
| 5,698,213 A | 12/1997 | Jamiolkowski et al. |
| 5,846,932 A | 12/1998 | Lowe et al. |
| 5,848,956 A | 12/1998 | Grettner |
| 5,849,489 A | 12/1998 | Heller |
| 5,948,761 A | 9/1999 | Seilhamer et al. |
| 6,013,630 A | 1/2000 | Shimkets |
| 6,124,430 A | 9/2000 | Mischak et al. |
| 6,162,603 A | 12/2000 | Heller |
| 6,162,902 A | 12/2000 | Mischak et al. |
| 6,165,458 A | 12/2000 | Foldvari et al. |
| 6,312,679 B1 | 11/2001 | Tomalia et al. |
| 6,376,207 B1 | 4/2002 | Mischak et al. |
| 6,407,211 B1 | 6/2002 | Burnett, Jr. et al. |
| 6,410,044 B1 | 6/2002 | Chudzik et al. |
| 6,551,795 B1 | 4/2003 | Rubenfield et al. |
| 6,586,396 B1 | 7/2003 | Seilhamer et al. |
| 6,613,332 B1 | 9/2003 | Michael et al. |
| 6,812,339 B1 | 11/2004 | Venter et al. |
| 6,818,619 B2 | 11/2004 | Burnett, Jr. et al. |
| 6,828,107 B2 | 12/2004 | Asada et al. |
| 6,833,447 B1 | 12/2004 | Goldman et al. |
| 6,849,714 B1 | 2/2005 | Bridon et al. |
| 6,887,470 B1 | 5/2005 | Bridon et al. |
| 6,887,481 B1 | 5/2005 | Chan et al. |
| 6,897,030 B2 | 5/2005 | Seilhamer et al. |
| 6,974,861 B2 | 12/2005 | Seilhamer et al. |
| 7,026,293 B2 | 4/2006 | Kitakaze |
| 7,179,790 B2 | 2/2007 | Seilhamer et al. |
| 7,214,786 B2 | 5/2007 | Kovalic et al. |
| 7,276,481 B2 | 10/2007 | Golembo et al. |
| 7,332,569 B2 | 2/2008 | Cojocaru et al. |
| 7,345,142 B2 | 3/2008 | Cohen et al. |
| 7,384,917 B2 | 6/2008 | Burnett, Jr. et al. |
| 7,754,852 B2 | 7/2010 | Burnett, Jr. et al. |
| 7,795,221 B2 | 9/2010 | Sharma et al. |
| 7,803,901 B2 | 9/2010 | Burnett, Jr. et al. |
| 7,964,564 B2 | 6/2011 | Burnett, Jr. et al. |
| 8,063,191 B2 | 11/2011 | Burnett, Jr. et al. |
| 8,076,288 B2 | 12/2011 | Levy et al. |
| 8,283,318 B2 | 10/2012 | Chen et al. |
| 8,324,162 B2 | 12/2012 | Simari et al. |
| 8,354,496 B2 | 1/2013 | Pan et al. |
| 8,357,656 B2 | 1/2013 | Simari et al. |
| 8,455,438 B2 | 6/2013 | Burnett, Jr. et al. |
| 8,530,422 B2 | 9/2013 | Chen et al. |
| 8,642,550 B2 | 2/2014 | Dickey et al. |
| 8,741,842 B2 | 6/2014 | Burnett, Jr. et al. |
| 8,835,601 B2 | 9/2014 | Chen et al. |
| 9,102,707 B2 | 8/2015 | Lee et al. |
| 9,441,027 B2 | 9/2016 | Lee et al. |
| 9,587,004 B2 | 3/2017 | Lee et al. |
| 2002/0082219 A1 | 6/2002 | Burnett et al. |
| 2004/0086976 A1 | 5/2004 | Fleer et al. |
| 2004/0123343 A1 | 6/2004 | Rosa et al. |
| 2005/0059600 A1 | 3/2005 | Burnett, Jr. et al. |
| 2006/0019890 A1 | 1/2006 | Kapoun et al. |
| 2006/0025367 A1 | 2/2006 | Simari |
| 2006/0172933 A1 | 8/2006 | James et al. |
| 2006/0183154 A1 | 8/2006 | Shih et al. |
| 2006/0293232 A1 | 12/2006 | Levy et al. |
| 2007/0042957 A1 | 2/2007 | Burnett, Jr. et al. |
| 2007/0281887 A1 | 12/2007 | Pan |
| 2008/0032933 A1 | 2/2008 | Burnett, Jr. et al. |
| 2009/0022729 A1 | 1/2009 | Mackman et al. |
| 2009/0054337 A1 | 2/2009 | Burnett et al. |
| 2009/0069243 A1 | 3/2009 | Burnett et al. |
| 2010/0041612 A1 | 2/2010 | Beinborn |
| 2010/0048468 A1 | 2/2010 | Gegg et al. |
| 2010/0204094 A1 | 8/2010 | Simari et al. |
| 2010/0266704 A1 | 10/2010 | Ahlheim et al. |
| 2011/0053787 A1 | 3/2011 | Brulliard et al. |
| 2011/0152191 A1 | 6/2011 | Burnett, Jr. et al. |
| 2011/0152194 A1 | 6/2011 | Burnett, Jr. et al. |
| 2011/0223230 A1 | 9/2011 | Hersel et al. |
| 2011/0269684 A1 | 11/2011 | Burnett, Jr. et al. |
| 2011/0282030 A1 | 11/2011 | Dickey et al. |
| 2012/0010142 A1 | 1/2012 | Burnett, Jr. et al. |
| 2012/0053123 A1 | 3/2012 | Burnett, Jr. et al. |
| 2012/0108514 A1 | 5/2012 | Burnett, Jr. et al. |
| 2012/0277155 A1 | 11/2012 | VanAntwerp et al. |
| 2013/0143816 A1 | 6/2013 | Pan et al. |
| 2013/0143820 A1 | 6/2013 | Simari et al. |
| 2013/0281375 A1 | 10/2013 | Burnett, Jr. et al. |
| 2013/0296241 A1 | 11/2013 | Chen et al. |
| 2013/0303454 A1 | 11/2013 | Burnett, Jr. et al. |
| 2014/0066367 A1 | 3/2014 | Chen et al. |
| 2014/0179605 A1 | 6/2014 | Chen et al. |
| 2014/0228294 A1 | 8/2014 | Burnett, Jr. et al. |
| 2014/0274901 A1 | 9/2014 | Ichiki et al. |
| 2014/0357561 A1 | 12/2014 | Chen et al. |

FOREIGN PATENT DOCUMENTS

| | | |
|---|---|---|
| WO | WO1984003285 | 8/1984 |
| WO | WO1984003825 | 10/1984 |
| WO | WO1989009611 | 10/1989 |
| WO | WO1993002556 | 2/1993 |
| WO | WO1993016687 | 9/1993 |
| WO | WO1995024419 | 9/1995 |
| WO | WO1998020165 | 5/1998 |
| WO | WO1998045329 | 10/1998 |
| WO | WO1999012576 | 3/1999 |
| WO | WO1999057318 | 11/1999 |
| WO | WO2000071576 | 11/2000 |
| WO | WO2001044284 | 6/2001 |
| WO | WO2002024895 | 3/2002 |
| WO | WO2004047871 | 6/2004 |
| WO | WO2004071736 | 8/2004 |
| WO | WO2005000095 | 1/2005 |
| WO | WO2005072055 | 8/2005 |
| WO | WO2006017852 | 2/2006 |
| WO | WO2006110743 | 10/2006 |
| WO | WO2007034498 | 3/2007 |
| WO | WO2007035600 | 3/2007 |
| WO | WO2008061355 | 5/2008 |
| WO | WO2008089532 | 7/2008 |
| WO | WO2009086126 | 7/2009 |
| WO | WO2012058585 | 5/2012 |
| WO | WO2014127120 | 8/2014 |

OTHER PUBLICATIONS

U.S. Appl. No. 61/116,024, filed Nov. 19, 2008, Burnett, Jr. et al.

Abbey and Potter, "Vasopressin-dependent inhibition of the C-type natriuretic peptide receptor, NPR-B/GC-B, requires elevated intracellular calcium concentrations," *J Biol Chem.*, 277(45):42423-42430, Epub Aug. 23, 2002.

Abdallah et al., "Mechanism of cGMP-mediated protection in a cellular model of myocardial reperfusion injury," *Cardiovasc Res.* Apr. 1, 2005; 66(1):123-131.

Abdallah et al., "Non-viral gene transfer: applications in developmental biology and gene therapy," *Biol Cell.*, 85(1):1-7, 1995.

Abdelhafiz, "Heart failure in older people: causes, diagnosis and treatment," *Age Ageing.*, 31(1):29-36, Jan. 2002.

Adelman et al., "In vitro deletional mutagenesis for bacterial production of the 20,000-dalton form of human pituitary growth hormone," *DNA*, 2(3):183-193, 1983.

Agullo et al., "Effect of ischemia on soluble and particulate guanylyl cyclase-mediated cGMP synthesis in cardiomyocytes," *Am J Physiol Heart Circ Physiol.*, 284(6):H2170-H2176, Epub Feb. 13, 2003.

Ahluwalia et al., "Vascular actions of natriuretic peptides. Cyclic GMP-dependent and -independent mechanisms," *Basic Res Cardiol.* Mar. 2004; 99(2):83-89. Epub Jan. 23, 2004.

Allen and O'Connor, "Management of acute decompensated heart failure," *Can Med Assoc J*, 176(6):797-805, Mar. 13, 2007.

Almquist et al., "Synthesis and biological activity of a ketomethylene analog of a tripeptide inhibitor of angiotensin converting enzyme," *J Med. Chem.* 1980; 23:1392-1398.

(56) References Cited

OTHER PUBLICATIONS

Anand-Srivastava, "Natriuretic peptide receptor-C signaling and regulation," *Peptides*, 26(6):1044-1059, Epub Apr. 8, 2005.
Anyadike et al., "Brain natriuretic peptide reverses the effects of myocardial stunning in rabbit myocardium," *Pharmacology.* 2007; 80(1):40-48. Epub May 21, 2007.
Arora et al., "Atrial natriuretic peptide is negatively regulated by microRNA-425," *J Clin Invest.*, 123(8):3378-3382, Epub Jul. 15, 2013.
Atlas and Laragh, "Physiological Actions of Atrial Natriuretic Factor," Atrial Hormones and Other Natriuretic Factors, 1987, Mulrow et al. (eds.), Am. Physiol. Soc., Bethesda, MD, pp. 53-76.
Ausubel et al., Ed., "Immunology," Short Protocols in Molecular Biology, Unit 11, Green Publishing Associates and John Wiley & Sons, 56 pages, 1992.
Ausubel et al., Ed., "Mutagenesis of Cloned DNA," Short Protocols in Molecular Biology, Unit 8, Green Publishing Associates and John Wiley & Sons, 26 pages, 1992.
Averill et al., "Cardiac angiotensin-(1-7) in ischemic cardiomyopathy," *Circulation.* Oct. 28, 2003; 108(17):2141-2146. Epub Sep. 29, 2003.
Banga, "Theme section: transdermal delivery of proteins," *Pharm Res.*, 24(7):1357-1359, Epub May 11, 2007.
Barber et al, "Atrial natriuretic peptide preserves endothelial function during intimal hyperplasia," *J Vasc Res.*, 42(2):101-110, Epub Jan. 19, 2005.
Barker and Dayhoff, "Detecting Distant Relationships: Computer Methods and Results," Atlas of Protein Sequence and Structure, 1972, vol. 5, National Biomedical Research Foundation, pp. 101-110.
Batlle et al., "New aspects of the renin-angiotensin system: angiotensin-converting enzyme 2—a potential target for treatment of hypertension and diabetic nephropathy," *Curr Opin Nephrol Hypertens.* May 2008; 17(3):250-257.
Baxter, "Natriuretic peptides and myocardial ischaemia," *Basic Res Cardiol.*, Mar. 2004; 99(2):90-93. Epub Jan. 23, 2004.
Benter et al., "Angiotensin-(1-7) prevents diabetes-induced cardiovascular dysfunction," *Am J Physiol Heart Circ Physiol.* Jan. 2007; 292(1):H666-H672.
Best et al., "Dendroaspis natriuretic peptide relaxes isolated human arteries and veins," *Cardiovasc Res.*, Aug. 1, 2002; 55(2):375-384.
Bestle et al., "Cardiovascular, endocrine, and renal effects of urodilatin in normal humans," *Am J Physiol.*, 276(3 Pt 2):R684-R695, Mar. 1999.
Betancourt et al., "Doxorubicin-loaded PLGA nanoparticles by nanoprecipitation: preparation, characterization and in vitro evaluation," Nanomedicine (Lond)., 2(2):219-232, Apr. 2007.
Blood Pressure UK, "Diuretics—blood pressure medication," Blood Pressure UK [online], 2008, [retrieved on Nov. 6, 2013]. Retrieved from the Internet: <URL: http://www.bloodpressureuk.org/BloodPressureandyou/Medicines/Medicinetypes/Diuretics>, 4 pages.
Boerrigter and Burnett, "Cardiorenal syndrome in decompensated heart failure: prognostic and therapeutic implications," Curr Heart Fail Rep. Sep. 2004; 1(3):113-120.
Boerrigter et al., "Targeting heme-oxidized soluble guanylate cyclase in experimental heart failure," *Hypertension*, 49(5):1128-1133. Epub Feb. 26, 2007.
Boerrigter et al., "Abstract 3478: Evidence for Differential Modulation of the Cardiorenal Actions of B-Type Natriuretic Peptide by the Peptidases Dipeptidyl Peptidase IV and Meprin A," Circulation, 118:S_432, 2008.
Bowie et al, "Deciphering the message in protein sequences: tolerance to amino acid substitutions," *Science*, 247(4948):1306-1310, Mar. 16, 1990.
Braunwald, "Shattuck lecture—cardiovascular medicine at the turn of the millennium: triumphs, concerns, and opportunities," *N Engl J Med.*, 337(19):1360-1369, Nov. 6, 1997.
Brenner et al., "Diverse biological actions of atrial natriuretic peptide," *Physiol Rev.*, 70(3):665-699, Jul. 1990.

Brosnihan et al., "Angiotensin-(1-7) dilates canine coronary arteries through kinins and nitric oxide," *Hypertension.* Mar. 1996; 27(3 Pt 2):523-528.
Brosnihan et al., "Angiotensin-(1-7): a novel vasodilator of the coronary circulation," *Biol Res.*, 1998; 31(3):227-234.
Brosnihan, "Effect of the angiotensin-(1-7) peptide on nitric oxide release," *Am J Cardiol.* Nov. 19, 1998; 82(10A):17S-19S.
Brugada et al., "Identification of a Genetic Locus for Familial Atrial Fibrillation," *N. Engl. J. Med.*, 336:905-911, 1997.
Bruneau et al., "BNP gene expression is specifically modulated by stretch and ET-1 in a new model of isolated rat atria," Am. J. Physiol., 1997, 273:H2678-H2686.
Bryan and Potter, "The atrial natriuretic peptide receptor (NPR-A/GC-A) is dephosphorylated by distinct microcystin-sensitive and magnesium-dependent protein phosphatases," J. Biol. Chem. 2002, 277:16041-16047.
Bryan et al., "Renal hyporesponsiveness to atrial natriuretic peptide in congestive heart failure results from reduced atrial natriuretic peptide receptor concentrations," Am. J. Physiol. Renal Physiol., 2007, 292:F1636-F1644.
Burchill et al., "Acute kidney injury in the rat causes cardiac remodelling and increases angiotensin-converting enzyme 2 expression," *Exp Physiol.* ,May 2008; 93(5):622-630. Epub Jan. 25, 2008.
Burger and Burger, BNP in decompensated heart failure: heart failure: Diagnostic, prognostic and therapeutic potential, Curr. Opin. Investig. Drugs, 2001, 2(7):929-35.
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol., 1990, 111:2129-2138.
Burley and Baxter, "B-type natriuretic peptide limits reperfusion injury via opening of ATP-sensitive potassium channels," *J Mol Cell Cardiol*, 40(6):967-968, Jun. 2006.
Burley et al., "Cardioprotective actions of peptide hormones in myocardial ischemia," *Heart Fail Rev.* Dec. 2007; 12(3-4):279-291.
Burley et al., "Cyclic GMP and protein kinase-G in myocardial ischaemia-reperfusion: opportunities and obstacles for survival signaling," *Br J Pharmacol.* Nov. 2007; 152(6):855-869. Epub Aug. 13, 2007.
Burnett et al., "Alterations in the kidney in heart failure: the cardiorenal axis in the regulation of sodium homeostasis." Heart failure: a companion to Braunwald's heart disease. Elsevier Inc, Philadelphia (2004): 279-289.
Burnett et al., "Atrial Natriuretic Peptide Elevation in Congestive Heart Failure in the Human", Science, 231, pp. 1145-1147, (Mar. 7, 1986).
Burnett et al., "Effects of synthetic atrial natriuretic factor on renal function and renin release," *Am J Physiol.*, 247(5 Pt 2):F863-F866, Nov. 1984.
Burns, "The emerging role of angiotensin-converting enzyme-2 in the kidney," *Curr Opin Nephrol Hypertens.* Mar. 2007; 16(2):116-121.
Cannone et al., "A genetic variant of the atrial natriuretic peptide gene is associated with cardiometabolic protection in the general community," J Am Coll Cardiol., 58(6):629-636, Aug. 2, 2011.
Cannone et al., "The atrial natriuretic peptide genetic variant rs5068 is associated with a favorable cardiometabolic phenotype in a Mediterranean population," Diabetes Care., 36(9):2850-2856, Epub May 1, 2013.
Carpino and Han, "The 9-Fluorenylmethoxycarbonyl Amino-Protecting Group," J. Org. Chem., 1972, 37(22):3404-3409.
Carstens et al., "Metabolism and action of urodilatin infusion in healthy volunteers," Clin. Pharmacol. Ther., 1998, 64:73-86.
Cataliotti et al., "Abstract 6278: Burden of Chronic Renal Insufficiency in the General Population and Added Predictive Power of GFR to BNP and NT-proBNP in Detection of Altered Ventricular Structure and Function," Circulation, 118:S_1173, 2008.
Cataliotti et al., "Brain natriuretic peptide enhances renal actions of furosemide and suppresses furosemide-induced aldosterone activation in experimental heart failure," *Circulation*, 109:1680-1685, 2004.

(56) References Cited

OTHER PUBLICATIONS

Cataliotti et al., "Chronic actions of a novel oral B-type natriuretic peptide conjugate in normal dogs and acute actions in angiontensin II mediated hypertension," Circulation, 118:1729-1736, 2008.

Cataliotti et al., "CNP production in the kidney and effects of protein intake restriction in nephrotic syndrome ," Am. J. Physiol., 283(3):F464-472, Sep. 2002.

Cataliotti et at., "Oral Brain Natriuretic Peptide: a Novel Strategy for Chronic Protein Therapy for Cardiovascular Disease," Trends Cardiovasc. Med., Jan. 2007, 17:10-14.

Cavero et al., "Cardiorenal Actions of Neutral Endopeptidase Inhibition in Experimental Congestive Heart Failure," Circulation, 1990, 82:196-201.

Chan et al., "Phosphodiesterase v inhibition has favorable effects on LV remodeling and potentiates the renal actions of subcutaneously administered BNP without adverse hemodynamic effects in experimental overt congestive heart failure," Circulation, vol. 110 No. 17, Suppl. S, pp. 22, Meeting Info.: 77th Scientific Meeting of the American-Heart-Association, Oct. 26, 2004.

Chang and Meienhofer, "Solid-Phase Peptide Synthesis Using Mild Base Cleavage of N.alpha.-Fluorenymethyloxycarbonylamino Acids, Exemplified by a Synthesisof Dihydrosomastatin," Int. J. Peptide Protein Res., 1978, 11:246-249.

Chappell et al., "Pathways of angiotensin-(1-7) metabolism in the kidney," Nephrol Dial Transplant. 2001; 16 Suppl 1:22-26.

Chappell, "Emerging evidence for a functional angiotensin-converting enzyme 2-angiotensin-(1-7)-MAS receptor axis: more than regulation of blood pressure?" Hypertension. Oct. 2007; 50(4):596-599. Epub Sep. 4, 2007.

Chauhan et al., "Release of C-type natriuretic peptide accounts for the biological activity of endothelium-derived hyperpolarizing factor," Proc Natl Acad Sci U S A. Feb. 4, 2003; 100(3):1426-1431. Epub Jan. 27, 2003.

Chaumet-Riffaud et al., "Altered PGE2 and PGF2 alpha production by glomeruli and papilla of sodium-depleted and sodium-loaded rats," Am. J. Physiol., 241:F517-F524, 1981.

Chaurand et al., "Peptide and protein identification by matrix-assisted laser desorption ionization (MALDI) and MALDI-post-source decay time-of-flight mass spectrometry," J Am Soc Mass Spectrom. Feb. 1999; 10(2):91-103.

Chen and Burnett, "The natriuretic peptides in heart failure: diagnostic and therapeutic potentials," Proc Assoc Am Physicians. Sep.-Oct. 1999; 111(5):406-416.

Chen and Burnett., "Clinical application of the natriuretic peptides in heart failure," European Heart Journal Supplements (2006) 8 (Supplement E), E18-E25.

Chen et al. "A novel designer natriuretic and diuretic peptide based upon an alternatively spliced BNP without vascular vasodilatory actions," Circulation, 2006, 114(18):270 (Abstract 1412).

Chen et al. "Renal Response to Acute Neutral Endopeptidase Inhibition in Mild and Severe Experimental Heart Failure," Circulation, 1999, 100:2443-2448.

Chen et al., "Local renal delivery of a natriuretic peptide a renal-enhancing strategy for B-type natriuretic peptide in overt experimental heart failure," J Am Coll Cardiol., 53(15):1302-1308, Apr. 14, 2009.

Chen et al., "Low dose nesiritide and the preservation of renal function in patients with renal dysfunction undergoing cardiopulmonary-bypass surgery: a double-blind placebo-controlled pilot study," Circulation. Sep. 11, 2007; 116(11 Suppl):I134-I138.

Chen et al., "Natriuretic peptide receptors and neutral endopeptidase in mediating the renal actions of a new therapeutic synthetic natriuretic peptide dendroaspis natriuretic peptide," J Am Coll Cardiol., Sep. 18, 2002; 40(6):1186-1191.

Chen et al., "Subcutaneous administration of brain natriuretic peptide in experimental heart failure," J Am Coll Cardiol., 36(5):1706-1712, Nov. 1, 2000.

Chen et al., "Subcutaneous BNP administration in symptomatic human heart failure: a novel therapeutic strategy for congestive heart failure," J Am Coll Cardiol., 35(2s1):240A, Feb. 1, 2000, 1 page.

Chen et al., "Abstract 1481: Renal Targeted Protein Therapeutics in Experimental Overt Heart Failure With Renal Dysfunction," Circulation, 118:S_334, 2008.

Chen et al., "Equimolar doses of atrial and brain natriuretic peptides and urodilatin have differential renal actions in overt experimental heart failure," Am J Physiol Regul Integr Comp Physiol., 288(5):R1093-R1097, Epub Dec. 30, 2004.

Chen et al., "KCNQ1 Gain-of-function mutation in familial atrial fibrillation," Science, 299:251-254, Jan. 2003.

Chen et al., "Maximizing the renal cyclic 3'-5'-guanosine monophosphate system with type V phosphodiesterase inhibition and exogenous natriuretic peptide: a novel strategy to improve renal function in experimental overt heart failure," J Am Soc Nephrol., 17(10):2742-2747, Epub Aug. 23, 2006.

Chen et al., "Natriuretic peptide receptors and neutral endopeptidase in mediating the renal actions of a new therapeutic synthetic natriuretic peptide dendroaspis natriuretic peptide," J Am Coll Cardiol., 40(6):1186-1191, Sep. 18, 2002.

Clavell et al., "Biological actions of brain natriuretic peptide in thoracic inferior vena caval constriction," Am. J. Physiol., 1993, 265:R1416-R1422.

Cockcroft and Gault, "Prediction of creatinine clearance from serum creatinine," Nephron., 16(1):31-41, 1976.

Cohn et al., "Cardiac remodeling-concepts and clinical implications: a consensus paper from an international forum on cardiac remodeling," J. Am. Coll. Cardiol., 2000, 35(3):569-582.

Cole et al., "The EBV-Hybridoma technique and its application to human lung cancer," Monoclonal Antibodies and Cancer Therapy, Alan R. Liss, Inc., 1983, pp. 77-96.

Costello-Boerrigter et al., "Renal and anti-aldosterone actions of vasopressin-2 receptor antagonism and B-type natriuretic peptide in experimental heart failure," Circ Heart Fail., 3(3):412-419. Epub Feb. 22, 2010.

Costello-Boerrigter et al., "Vasopressin-2-receptor antagonism augments water excretion without changes in renal hemodynamics or sodium and potassium excretion in human heart failure," Am J Physiol Renal Physiol., 2006, 290:F273-F278.

Cote et al. "Generation of human monoclonal antibodies reactive with cellular antigens," Proc. Natl. Acad. Sci. USA, 1983, 80:2026-2030.

Cote et al., "Generation of human monoclonal antibodies reactive with cellular antigens," Proc Natl Acad Sci U S A. Apr. 1983; 80(7):2026-2030.

Cowie and Mendez, "BNP and congestive heart failure," Prog Cardiovasc Dis., 44(4):293-321, Jan.-Feb. 2002.

Crea et al., "Chemical synthesis of genes for human insulin," Proc. Natl. Acad. Sci. USA, 1978, 75(12):5765-5769.

Cullen et al., "Crystal and Molecular Structure of a 4,5-Dimethyoxbilindione derived from Etiobiliverdin-IV.gamma.. a Possible Model Compound for the Phytochrome Chromophore," J.Chem. Soc. Perkin Trans., 1982, 1:307-312.

Cunningham et al., "Production of an atrial natriuretic peptide variant that is specific for type A receptor," Embo J, 1994, 13(11):2508-2515.

Currie et al., "Purification and sequence analysis of bioactive atrial peptides," Science, 223(4631):67-69., 1984.

Da Costa Gonsalves et al., "Evidence that the vasodilator angiotensin-(1-7)-Mas axis plays an important role in erectile function," Am J Physiol Heart Circ Physiol. Oct. 2007; 293(4):H2588-H2596. Epub Jul. 6, 2007.

Danhier et al., "PLGA-based nanoparticles: an overview of biomedical applications," J Control Release., 161(2):505-522, Epub Feb. 4, 2012.

Darbar et al., "Familial atrial fibrillation is a genetically heterogeneous disorder," J. Am. Coll. Cardiol., 41(12):2185-2192, 2003.

Davidson and Sackner, "Simplification of the anthrone method for the determination of inulin in clearance studies," J. Lab. & Clin. Med., 1963, 62:351-356.

(56) References Cited

OTHER PUBLICATIONS

De Bold et al., "A rapid and potent natriuretic response to intravenous injection of atrial myocardial extract in rats," *Life Sci.*, Jan. 5, 1981; 28(1):89-94.
De Mello, "Angiotensin (1-7) re-establishes impulse conduction in cardiac muscle during ischaemia-reperfusion. The role of the sodium pump," *J Renin Angiotensin Aldosterone Syst.* Dec. 2004; 5(4):203-208.
Deckard and Ebright, "Therapeutic hypothermia after cardiac arrest: What, why, who, and how" American Nurse Today., 6(7):23-28, Jul. 2011.
Del Ry et al., "C-type natriuretic peptide and heart failure," *Pharmacol Res.* Nov. 2006; 54(5):326-333. Epub Jul. 8, 2006.
Del Ry, "Radioimmunoassay for plasma C-type natriuretic peptide determination: a methodological evaluation," *Clinical Chemistry and Laboratory Medicine*, 43(6):641-645, Jun. 2005.
DelliPizzi et al., "Natriuretic action of angiotensin(1-7)," *Br J Pharmacol.* Jan. 1994; 111(1):1-3.
Di Nisio et al., "Direct thrombin inhibitors," *N Engl J Med.*, Sep. 8, 2005; 353(10):1028-1040.
Dickey et al., "Differential Regulation of Membrane Guanylyl Cyclases in Congestive Heart Failure: Natriuretic Peptide Receptor (NPR)-B, Not NPR-A, is the Predominant Natriuretic Peptide Receptor in the Failing Heart," Endocrinology, 2007, 148(7):3518-3522.
Dickey et al., "Novel bifunctional natriuretic peptides as potential therapeutics," J. Biol. Chem., 2008, 283(50):35003-35009.
Dickey et al., "A familial mutation renders atrial natriuretic peptide resistant to proteolytic degradation," J. Biol. Chem., 284: 19196-19202, 2009.
Dietz et al., "Evidence supporting a physiological role for proANP-(1-30) in the regulation of renal excretion," Am J Physiol Regul Integr Comp Physiol., 280(5):R1510-R1517, May 2001.
Dietz, "Mechanisms of atrial natriuretic peptide secretion from the atrium," *Cardiovasc Res.*, 68(1):8-17, Oct. 1, 2005.
Doi et al., "C-type natriuretic peptide induces redifferentiation of vascular smooth muscle cells with accelerated reendothelialization," Arterioscler. Thromb. Vasc. Biol., 2001, 21(6):930-936.
Dong et al., "Overexpression of ACE2 enhances plaque stability in a rabbit model of atherosclerosis," *Arterioscler Thromb Vasc Biol.* Jul. 2008; 28(7):1270-1276. Epub Apr. 10, 2008.
Donnelly et al., "Protective Efficacy of Intramuscular Immunization with Naked DNA," Ann. N.Y. Acad. Sci., 1995, 772:40-46.
Dorner et al., "Hemodynamic effects of continuous urodilatin infusion: A dose finding study," Clin. Pharmacol. Ther., 1998, 64:322-330.
D'Souza et al., "B-type natriuretic peptide limits infarct size in rat isolated hearts via KATP channel opening," *Am J Physiol Heart Circ Physiol.* May 2003; 284(5):H1592-H1600. Epub Jan. 9, 2003.
Edwards et al., "Atrial Stretch, Not Pressure, Is the Principal Determinant Controlling the Acute Release of Atrial Natriuretic Factor," Circ. Res., 1988, 62:191-195.
Espiner et al., "ABCs of natriuretic peptides: growth," *Horm Res*, Feb. 2007; 67(Suppl 1):81-90.
Fan et al., "Down-regulation does not mediate natriuretic peptide-dependent desensitization of natriuretic peptide receptor (NPR)-A or NPR-B: guanylyl cyclase-linked natriuretic peptide receptors do not internalize," Mol. Pharmacol., 2005, 67:174-183.
Fenelon et al., "Examination of the in vivo cardiac electrophysiological effects of nesiritide (human brain natriuretic peptide) in conscious dogs," J. Cardiac Failure, 8:320-325, 2002.
Ferrario and Iyer, "Angiotensin-(1-7): a bioactive fragment of the renin-angiotensin system," *Regul Pept.* Nov. 30, 1998; 78(1-3):13-18.
Ferreira et al., "Angiotensin-(1-7) improves the post-ischemic function in isolated perfused rat hearts," *Braz J Med Biol Res.* Sep. 2002; 35(9):1083-1090. Epub Aug. 30, 2002.
Ferreira et al., "Angiotensin-(1-7): cardioprotective effect in myocardial ischemia/reperfusion," *Hypertension.* Sep. 2001; 38(3 Pt 2):665-668.

Flynn et al., "The amino acid sequence of an atrial peptide with potent diuretic and natriuretic properties," Biochem. Biophys. Res. Commun., 1983, 117(3):859-865.
Fonarow et al., "Factors identified as precipitating hospital admissions for heart failure and clinical outcomes: findings from OPTIMIZE-HF," Arch Intern Med., 168(8):847-854, Apr. 28, 2008.
Fonarow, "B-type natriuretic peptide: spectrum of application. Nesiritide (recombinant BNP) for heart failure," *Heart Failure Reviews*, 8:321-325, Oct. 2003.
Forfia et al., "Acute phosphodiesterase 5 inhibition mimics hemodynamic effects of B-type natriuretic peptide and potentiates B-type natriuretic peptide effects in failing but not normal canine heart," *J Am Coll Cardiol.*, 49(10):1079-1088. Epub Feb. 26, 2007.
Forssmann et al., "The renal urodilatin system: clinical implications," Cardiovasc Res., 51(3):450-462, Aug. 15, 2001.
Fox et al., "Parental atrial fibrillation as a risk factor for atrial fibrillation in offspring," JAMA, 291:2851-2855, 2004.
Fraga-Silva et al., "The antithrombotic effect of angiotensin-(1-7) involves mas-mediated NO release from platelets," *Mol Med.* Jan.-Feb. 2008; 14(1-2):28-35.
Funder and Reincke, "Aldosterone: a cardiovascular risk factor?" Biochim Biophys Acta., 1802(12):1188-1192, Epub Aug. 13, 2010.
Furuya et al., "C-type natriuretic peptide is a growth inhibitor of rat vascular smooth muscle cells," *Biochem Biophys Res Commun.* Jun. 28, 1991; 177(3):927-931.
Furuya et al., "Structural requirements of C-type natriuretic peptide for elevation of cyclic GMP in cultured vascular smooth muscle cells," *Biochem Biophys Res Commun.*, Mar. 31, 1992; 183(3):964-969.
Gaddam et al., "Aldosterone and cardiovascular disease," Curr Probl Cardiol., 34(2):51-84, Feb. 2009.
Gagelmann et al., "Urodilatin (CDD/ANP-95-126) is not biologically inactivated by a peptidase from dog kidney cortex membranes in contrast to atrial natriuretic peptide/cardiodilatin (.alpha.-hANP/CDD-99-126)," FEBS Lett., 1988, 233(2):249-254.
Gallagher and Tallant, "Inhibition of human lung cancer cell growth by angiotensin-(1-7)," *Carcinogenesis.* Nov. 2004; 25(11):2045-2052. Epub Jul. 29, 2004.
Genbank Accession No. ADW08083, "Human brain natriuretic polypeptide (BNP)2 mature protein SeqID36," dated Mar. 24, 2005, 1 page.
Genbank Accession No. AEB63460, "HUMNATPEP_PEA_1_P2 residues 103-162," dated Oct. 20, 2005, 1 page.
GenBank Accession No. AJ712145 CMPD01 *Homo sapiens* cDNA clone CMPD10397, mRNA sequence-database entry date Jun. 30, 2004, 1 page.
GenBank Accession No. AJ712145, "AJ712145 CMPD01 *Homo sapiens* cDNA clone CMPD10397, mRNA sequence," database entry date Jun. 30, 2004, 1 page.
GenBank Accession No. BC005893, dated Jul. 15, 2006, 3 pages.
GenBank Accession No. BQ130005, "ij83b04.x1 Human insulinoma *Homo sapiens* cDNA clone IMAGE:5777983 3-, mRNA sequence," dated Jul. 15, 2003, 2 pages.
GenBank Accession No. BQ130258, "ij83b04.y1 Human insulinoma *Homo sapiens* cDNA clone IMAGE:5777983 5' similar to SW:ANFB_HUMAN P16860 Brain Natriuretic Peptide Precursor ;, mRNA sequence," dated Jul. 15, 2003, 2 pages.
GenBank Accession No. M25296, "Human natriuretic peptide precursor mRNA, complete cds," dated Apr. 27, 1993, 1 page.
Gevaert et al., "Protein identification based on matrix assisted laser desorption/ionization-post source decay-mass spectrometry," *Electrophoresis.* May 2001; 22(9):1645-1651.
Gheorghiade et al., "Navigating the Crossroads of Coronary Artery Disease and Heart Failure," Circulation, 2006,114:1202-1213.
Girbes et al., "Renal Function Is the Most Important Determinant of Survival in Patients With Severe Congestive Heart Failure," J. Am. Coll. Cardiol., 1998, 31:154A.
Goebel and Neubert, "Dermal peptide delivery using colloidal carrier systems," Skin Pharmacol Physiol., 21(1):3-9, Epub Oct. 2, 2007.
Goeddel et al., "Synthesis of human fibroblast interferon by *E. coli*," Nucl. Acids Res., 1980, 8(18):4057-4074.

(56) References Cited

OTHER PUBLICATIONS

Goetz et al., "Evidence that Urodilatin, Rather Than ANP, Regulates Renal Sodium Excretion," J. Am. Soc. Nephrol.,1990, 1:867-874.
Gollob et al., "Somatic Mutations in the Connexin 40 Gene (GJA5) in Atrial Fibrillation," N. Engl. J. Med., 354:2677-2688, 2006.
Gorelik et al., "Angiotensin 1-7 induces bradykinin-mediated relaxation in porcine coronary artery," *J Pharmacol Exp Ther*. Jul. 1998; 286(1):403-410.
Grantham and Burnett, "Natriuretic Peptides in Cardiovascular Disease," Natriuretic Peptides in Health and Disease, 1997, Samson and Levin (eds.), Humana Press, pp. 309-326.
Grobe et al, "Chronic angiotensin-(1-7) prevents cardiac fibrosis in DOCA-salt model of hypertension," *Am J Physiol Heart Circ Physiol*. Jun. 2006; 290(6):H2417-H2423. Epub Jan. 13, 2006.
Guatelli et al., "Isothermal, in vitro amplification of nucleic acids by a multienzyme reaction modeled after retroviral replication," *Proc Natl Acad Sci U S A*. Mar. 1990; 87(5):1874-1878.
Gudbjartsson et al., "Variants conferring risk of atrial fibrillation on chromosome 4q25 ," Nature, 448:353-357, 2007.
Guo et al., "Protein tolerance to random amino acid change," Proc. Natl. Acad. Sci. USA, 2004, 101(25):9205-9210.
Ha et al., "Dendroaspis natriuretic peptide protects the post-ischemic myocardial injury," *Regul Pept*. Jan. 15, 2006; 133(1-3):13-19. Epub Nov. 11, 2005.
Haber et al. "Application of a radioimmunoassay for angiotensin I to the physiologic measurements of plasma renin activity in normal human subjects," J Clin Endocrinol, 1969, 29:1349-1355.
Haller et al., "Safety issues specific to clinical development of protein therapeutics," *Clin Pharmacol Ther*. Nov. 2008; 84(5):624-627. Epub Aug. 13, 2008.
Hann, "On the double bond isostere of the peptide bond: preparation of an enkephalin analogue," *J Chem. Soc. Perkin Trans.*, 1982, 1:307-314.
Hata et al., "Effects of carperitide on the long-term prognosis of patients with acute decompensated chronic heart failure: the PROTECT multicenter randomized controlled study," Circ J., 72(11):1787-1793, Epub Sep. 24, 2008.
Hauptmann and Stürzebecher, "Synthetic inhibitors of thrombin and factor Xa: from bench to bedside," *Thromb Res*. Mar. 1, 1999; 93(5):203-241.
Hawkridge et al., "Quantitative mass spectral evidence for the absence of circulating brain natriuretic peptide (BNP-32) in severe human heart failure," Proc Natl Acad Sci U S A., 102(48):17442-17447, Epub Nov. 17, 2005.
Heller et al., "Effect of intrarenal infusion of angiotensin-(1-7) in the dog," *Kidney Blood Press Res*. 2000; 23(2):89-94.
Heublein et al., "Immunoreactivity and guanosine 3',5'-cyclic monophosphate activating actions of various molecular forms of human B-type natriuretic peptide," Hypertension, 49(5):1114-1119, Epub Mar. 19, 2007.
Hillock et al., "B-type natriuretic peptide infusions in acute myocardial infarction," *Heart*. May 2008; 94(5):617-622. Epub Jul. 16, 2007.
Hirsch et al., "ANP and Urodilatin. Who Is Who in the Kidney," Eur. J. Med. Res., 2006, 11:447-454.
Hobbs et al., "Natriuretic peptide receptor-C regulates coronary blood flow and prevents myocardial ischemia/reperfusion injury: novel cardioprotective role for endothelium-derived C-type natriuretic peptide," *Circulation*. Sep. 7, 2004; 110(10):1231-1235. Epub Aug. 30, 2004.
Hodgson-Zingman, "Atrial natriuretic peptide frameshift mutation in familial fibrillation," N. Engl. J. Med., 359(2):158-165, 2008.
Holladay et al., "Synthesis of hydroxyethylene and ketomethylene dipeptide isosteres," *Tetrahedron Lett.*, 1983, 24:4401-4404.
Horio et al., "Gene expression, secretion and autocrine action of c-type natriuretic peptide in cultured adult rat cardiac fibroblasts," 2003, Endocrinology, 144(6):2279-2284.
Hruby, "Conformational restrictions of biologically active peptides via amino acid side chain groups," *Life Sci.*, Jul. 1982, 31:189-199.
Hudson et al., "Methionine enkephalin and isosteric analogues. I. Synthesis on a phenolic resin support," *Int J Pept Protein Res.*, 1979; 14(3):177-185.
Hunt et al., "Bioactivity and metabolism of C-type natriuretic peptide in normal man," *J Clin Endocrinol Metab.*, Jun. 1994; 78(6):1428-1435.
Hunt et al., "Hypotension and bradycardia during caloric restriction in mice are independent of salt balance and do not require ANP receptor," Am. J. Physiol. Heart Circ. Physiol., 287(4):H1446-H1451, 2004.
Huntley et al., "BNP-induced activation of cGMP in human cardiac fibroblasts: interactions with fibronectin and natriuretic peptide receptors," *J Cell Physiol.*, Dec. 2006; 209(3):943-949.
Huse et al., "Generation of a large combinatorial library of the immunoglobulin repertoire in phage lambda," *Science*. Dec. 8, 1989; 246(4935):1275-1281.
Hyrup and Nielsen, "Peptide nucleic acids (PNA): synthesis, properties and potential applications," Bioorgan. Med. Chem., 4(1):5-23, Jan. 1996.
Ibebuogu et al., "Decompensated heart failure is associated with reduced corn levels and decreased cleavage of pro-atrial natriuretic peptide," Circ Heart Fail., 4(2):114-120, Epub Jan. 7, 2011.
Ichiki and Burnett, "Protein therapeutics for cardiovascular disease: it is all about delivery," J Am Coll Cardiol., 60(24):2558-2560, Epub Nov. 24, 2012.
Ichiki et al., "Abstract 11349: The natriuretic peptide prohormones are processed into active peptides in the normal human circulation and the processing is preserved in heart failure," Circulation, 126: A11349, 2012.
Ichiki et al., "All three NP pre/prohormones are processed in human blood into biologically active mature peptides," 16th Annual Scientific Meeting of Heart Failure Society of America, Sep. 10, 2012 [slideshow].
Ichiki et al., "Corin is present in the normal human heart, kidney, and blood, with pro-B-type natriuretic peptide processing in the circulation," Clin Chem., 57(1):40-47, Epub Nov. 12, 2010.
Ichiki et al., "Differential expression of the pro-natriuretic peptide convertases corin and furin in experimental heart failure and atrial fibrosis," Am J Physiol Regul Integr Comp Physiol., 304(2): R102—R109, Nov. 14, 2012.
Ichiki et al., "Pro-atrial natriuretic peptide in vitro and in vivo normal canines: A selective renal enhancing therapeutic," 17th Annual Scientific Meeting of the Heart Failure Society of America, Orland FL, USA, Sep. 23, 2013, 1 page [abstract].
Ichiki et al., "Pro-atrial natriuretic peptidel-126 is processed in the human circulation to a mature GC-A activating peptide with therapeutic potential in heart failure," ESC Congress 2013, Amsterdam, Netherland, Aug. 31, 2013.
Ichiki et al., "Pro-atrial natriuretic peptidel-126 is processed in the human circulation to a mature GC-A activating peptide with therapeutic potential in heart failure," Eur Heart J., 34 (suppl 1): doi: 10.1093/eurheartj/eht307.66, Aug. 31, 2013 [abstract].
Ichiki et al., "The natriuretic peptide prohormones are processed into active peptides in the normal human circulation and the processing is preserved in heart failure," American Heart Association Scientific meeting, Nov. 7, 2012, [poster], 1 page.
Ichiki et al., "The processing and degradation of preproANP in the circulation in normal human and patients with heart failure," The 77th Annual Scientific Meeting of Japanese Circulation Society (JCS 2013), Yokohama, Japan, Mar. 16, 2013, 1 page.
Igaki et al., "Effects of intravenously administered c-type natriuretic peptide in humans: comparison with atrial natriuretic peptide," *Hypertens Res.*, 1998, 21(1):7-13, 1998.
Inserte et al., "Urodilatin limits acute reperfusion injury in the isolated rat heart," *Cardiovasc Res*. Jan. 14, 2000; 45(2):351-359.
Iusuf et al., "Angiotensin-(1-7): pharmacological properties and pharmacotherapeutic perspectives," *Eur J Pharmacol.*, 585(2-3):303-312. Epub Mar. 15, 2008.
Iwata et al., "Angiotensin-(1-7) binds to specific receptors on cardiac fibroblasts to initiate antifibrotic and antitrophic effects," *Am J Physiol Heart Circ Physiol*. Dec. 2005; 289(6):H2356-H2363. Epub Jul. 15, 2005.

(56) References Cited

OTHER PUBLICATIONS

Jain et al., "Controlled release of drugs from injectable in situ formed biodegradable PLGA microspheres: effect of various formulation variables," *Eur J Pharm Biopharm.*, 50(2):257-262, Sep. 2000.
Jennings-White et al., "Synthesis of ketomethylene analogs of dipeptides," *Tetrahedron Lett.*, 23:2533-2534, 1982.
Ji et al., "Role of angiotensin-converting enzyme 2 and angiotensin(1-7) in 17beta-oestradiol regulation of renal pathology in renal wrap hypertension in rats," *Exp Physiol.*, May 2008; 93(5):648-657. Epub Feb. 22, 2008.
Jiang et al., "Ectodomain shedding and autocleavage of the cardiac membrane protease corin," *J Biol Chem.*, 286(12):10066-10072. Epub Feb. 2, 2011.
Jin et al. "Novel Analog of Atrial Natriuretic Peptide Selective for Receptor-A Produces Increased Diuresis and Natriuresis in Rats," *J Clin Invest*, 98(4):969-976, 1996.
Johns et al., "Dendroaspis natriuretic peptide binds to the natriuretic peptide clearance receptor," *Biochem. Biophys. Res. Comm.*, 358(1):145-149, 2007.
Jougasaki et al., "Augmented cardiac cardiotrophin-1 in experimental congestive heart failure," *Circulation*, 2000, 101:14-17.
Kalra et al., "Cardiorenal disease: a clinical intersection," *International Urol. And Nephrol.*, 37(1):175-184, 2005.
Kambayashi et al., "Isolation and sequence determination of human brain natriuretic peptide in human atrium," *FEBS Lett.*, 1990, 259(2):341-345.
Kasama et al., "Effects of intravenous atrial natriuretic peptide on cardiac sympathetic nerve activity and left ventricular remodeling in patients with first anterior acute myocardial infarction," *J Am Coll Cardiol.* Feb. 13, 2007; 49(6):667-674. Epub Jan. 26, 2007.
Kato et al., "Atrial natriuretic peptide promotes cardiomyocyte survival by cGMP-dependent nuclear accumulation of zyxin and Akt," *J Clin Invest.*, Oct. 2005; 115(10):2716-2730.
Keidar et al., "ACE2 of the heart: From angiotensin I to angiotensin (1-7)," *Cardiovasc Res.* Feb. 1, 2007; 73(3):463-469. Epub Sep. 19, 2006.
Kenny and Stephenson, "Role of endopeptidase-24.11 in the activation of atrial natriuretic peptide," *FEBS Lett.*, 232(1):1-8, 1998.
Kenny et al., "Hydrolysis of human and pig brain natriuretic peptides, urodilatin, C-type natriuretic peptide and some C-receptor ligands by endopeptidase-24.11," Biochem J., 291 ( Pt 1):83-88, Apr. 1, 1993.
Kim and Burgess, "Pharmacokinetic characterization of 14C-vascular endothelial growth factor controlled release microspheres using a rat model," J. Pharm. Pharmacol., 54(7):897-905, Jul. 2002.
Kitakaze et al. Large-scale trial using atrial natriuretic peptide or nicorandil as an adjunct to percutaneous coronary intervention for ST-segment elevation acute myocardial infarction [abst]. *Circulation* 2006; 114:2425-2426.
Kitakaze et al., "Human atrial natriuretic peptide and nicorandil as adjuncts to reperfusion treatment for acute myocardial infarction (J-WIND): two randomised trials," *Lancet.* Oct. 27, 2007; 370(9597):1483-1493.
Kjems et al., "The influence of GLP-1 on glucose-stimulated insulin secretion: effects on beta-cell sensitivity in type 2 and nondiabetic subjects," *Diabetes*, 52(2):380-386, Feb. 2003.
Köhler and Milstein, "Continuous cultures of fused cells secreting antibody of predefined specificity," *Nature.* Aug. 7, 1975; 256(5517):495-497.
Koitka et al., "Angiotensin converting enzyme 2 in the kidney," *Clin Exp Pharmacol Physiol.*, Apr. 2008; 35(4):420-425.
Koller et al., "Selective Activation of the B Natriuretic Peptide Receptor by C-Type Natriuretic Peptide (CNP)," *Science*, 1991, 252:120-123.
Komatsu et al., "C-type natriuretic peptide (CNP) in rats and humans," *Endocrinol.*, Aug. 1991,129:1104-1106.
Kosbor and Roder, "The production of monoclonal antibodies from human lymphocytes," *Immunology Today*, 4(3):72-79, Mar. 1983.

Kuhn, "Structure, Regulation, and Function of Mammalian Membrane Guanylyl Cyclase Receptors, With a Focus on Guanylyl Cyclase-A," *Circ Res.* Oct. 17, 2003; 93(8):700-9.
Kumar et al., "Expression of Guanylyl Cyclase-A/Atrial Natriuretic Peptide Receptor Blocks the Activation of Protein Kinase C in Vascular Smooth Muscle Cells: Role of cGMP and GMP-Dependent Protein Kinase," *Hypertension*; 1997, 29 (1 Pt 2):414-21.
La Villa et al., "Different effects of atrial and c-type natriuretic peptide on the urinary excretion of endothelin-1 in man," Clin. Sci. (Lond), 1998, 95(5):595-602.
Lambert et al., "Angiotensin-converting enzyme 2 and new insights into the renin-angiotensin system," *Biochem Pharmacol.* Feb. 15, 2008; 75(4):781-786. Epub Aug. 17, 2007.
Lambert et al., "Development of an in situ forming biodegradable poly-lactide-co-glycolide system for the controlled release of proteins," J. Controlled Release, 33:189-195 (1995).
Langenickel et al., "Cardiac hypertrophy in transgenic rats expressing a dominant-negative mutant of the natriuretic peptide receptor B," Proc Natl Acad Sci USA, 2006, 103(12):4735-4740.
Lawn et al., "The sequence of human serum albumin cDNA and its expression in *E. coli*," Nucl. Acids Res., 1981, 9(22):6103-6114.
Le Tran and Forster, "Angiotensin-(1-7) and the rat aorta: modulation by the endothelium," *J Cardiovasc Pharmacol.*, Nov. 1997; 30(5):676-682.
Leader et al., "Protein therapeutics: a summary and pharmacological classification," *Nat Rev Drug Discov.* Jan. 2008; 7(1):21-39.
Lebl and Hruby, "Synthesis of cyclic peptides by solid phase methodology," *Tetrahedron Lett.*, 1984, 25:2067-2068.
Lee and Burnett, "Natriuretic peptides and therapeutic applications," Heart Fail Rev., 12(2):131-142, Jun. 2007.
Lee and Burnett, "Design, synthesis and in vivo actions of a novel designer natriuretic peptide, BUA-NP," J Clin Pharmacol., 48(9):1133, Abstract 147. [presented as a poster] Thirty-Seventh Annual Meeting of the American College of Clinical Pharmacology in Philadelphia, PA on Sep. 15, 2008.
Lee and Burnett, "Design, synthesis, and cardiorenal actions of a novel peptide, CDD-NP," J Clin Pharmacol, 48( 9):1132, Abstract 143, Sep. 2008.
Lee and Burnett, "Design, synthesis, and in vivo pharmacologic actions of a novel designer natriuretic peptide fusing human atrial natriuretic peptide and human B-type natriuretic peptide," *Can J Cardiol.*, vol. 24 Suppl E, p. 85E, abstract 0179, [presented as a poster] presented at The Canadian Cardiovascular Congress in Toronto, Canada on Oct. 26, 2008.
Lee and Burnett, "Engineered mutation of human B-type natriuretic peptide to preserve renal perfusion pressure," J Card Fail., 14(6) Suppl: S3-S4, Abstract 009, Aug. 2008. Presented as an oral presentation at The 12th Annual Scientific Meeting of the Heart Failure Society of America in Toronto, Canada on Sep. 22, 2008.
Lee and Burnett, "Pharmacodynamics of a novel designer natriuretic peptide, BUA-NP, in normal anesthetized dogs," Abstract 851, Pulsus [online] 2009 [retrieved on Dec. 11, 2013]. Retrieved from the Internet: < URL: http://www.pulsus.com/ccc2009/abs/701.htm>, 1 page, Canadian Cardiovascular Congress, 62nd Annual Meeting of the Canadian Cardiovascular Society, 2009.
Lee et al., "A first-in-human clinical trial of a novel chimeric natriuretic peptide, CD-NP, in healthy subjects," Eur Heart J, 29(Abstract Supplement):299, Abstract P1949, 2008.
Lee et al., "Abstract 2495: Pharmacodynamic Profile of a Novel Chimeric Natriuretic Peptide, CD-NP, as Compared to C-Type Natriuretic Peptide," *Circulation.* 2007; 116:II_550.
Lee et al., "Cyclic GMP stimulating actions of two novel peptides, CU-NP and CNP-C, as assessed in isolated canine glomeruli," J Clin Pharmacol, 48(9):1133, Abstract 145, Sep. 2008.
Lee et al., "Design, synthesis and cardiorenal actions of two novel peptides derived from human B-type natriuretic peptide" ICRH's Young Investigators Forum, May 21-23, 2009, p. 8, Retrieved from the Internet: <URL: http://www.f2fe.com/yiforum/2009/fwyi09/5a%20Poster%20Abstracts%-20Day%201.pdf>, 1 page.
Lee et al., "Evaluation of a novel designer peptide, CU-NP, in human aortic endothelial cells and in vivo" J Clin Pharmacol, 48(9):1132, Abstract 144, Sep. 2008.

(56) References Cited

OTHER PUBLICATIONS

Lee et al., "Hemoconcentrating effects of two novel designer natriuretic peptides, CU-NP and CBB-NP," J Clin Pharmacol, 48(9):1133, Abstract 146, Sep. 2008.

Lee et al., "Renal and Neurohumoral Actions of a Novel Chimeric Natriuretic Peptide, CD-NP," 2007, Late-breaking abstract accepted for the Annual Meeting of the American Society for Clinical Pharmacology and Therapeutics Meeting, Abstract LBII-A-I, 1 page, Mar. 21-24, 2007.

Lee et al., "Abstract 1485: Tissue Specific Activation of cGMP by an Alternatively Spliced Form of BNP," Circulation, 118:S_335, 2008.

Lee et al., "Abstract 1497: A Novel Designer Natriuretic Peptide, CAA-NP, As Assessed in Human Aortic Endothelial Cells: Evidence for Involvement of Natriuretic Peptide Receptor-A (NPR-A) and NPR-B in Cyclic GMP Response," Circulation, 118:S_337-S_338, 2008.

Lee et al., "Abstract 371: Cardiorenal and Neurohumoral Actions of a Novel Designer Natriuretic Peptide, CU-NP, in Canine Experimental Heart Failure," Circulation. 2008;118:S_293, 2008.

Lee et al., "Abstract 5432: Mutation of Three Amino Acids in the Disulfide-Ring of a CNP Based Chimeric Natriuretic Peptide Alters its Vascular Properties," Circulation, 118:S_549, 2008.

Lee et al., "Abstract P140: A Novel New Generation Designer Natriuretic Peptide, CBB-NP, Exerts Favorable Cardiorenal and Neurohumoral Actions," Circulation, 118:S_1475, 2008.

Lee et al., "Designer natriuretic peptides," Jan. 2009, *J Invest Med.*, 57(1):18-21.

Lee et al., "Neurohormonal profile of a novel chimeric natriuretic peptide, CD-NP, as compared to C-type natriuretic peptide, in the normal dog," *J. Cardiac. Failure*, 13(6Suppl):S144 (Abstract 239), 2007.

Lee et al., "Pharmacodynamics of a novel designer natriuretic peptide, CD-NP, in a first-in-human clinical trial in healthy subjects," J Clin Pharmacol., 49(6):668-673, Epub Apr. 2009.

Lee et al., "Renal actions of a novel designer natriuretic peptide, CU-NP, as compared to C-type natriuretic peptide," *Clin Pharmacol Ther*,. Mar. 2008; vol. 83 Suppl 1 :S11, Abstract PI-08.

Lee et al., "Renal Cyclic GMP Stimulating Actions of a Novel Chimeric Natriuretic Peptide CD-NP in Isolated Glomeruli: Evidence for NPR-A Activation," Journal of Cardiac Failure, 14(6): S11, Abstract 028, Aug. 2008, 12th Annual Scientific Meeting, Heart Failure Society of America, (HFSA), Sep. 21-24, 2008, Toronto, Ontario, Canada, 1 page.

Lee, "Engineered Mutation of Human B-Type Natriuretic Peptide to Preserve Renal Perfusion Pressure," [oral presentation slides] Jay N. Cohn New Investigator Clinical/Integrative Physiology Award Competition, the Annual Scientific Meeting of the Heart Failure Society of America, Sep. 22, 2008, 24 pages.

Levey et al., "A more accurate method to estimate glomerular filtration rate from serum creatinine: a new prediction equation. Modification of Diet in Renal Disease Study Group," *Ann Intern Med.*, 130(6):461-70, Mar. 16, 1999.

Levey, "Nondiabetic Kidney Disease," N. Engl. J. Med., 2002, 347(19):1505-1511.

Levin et al., "Natriuretic peptides," N. Engl. J. Med., 339(5):321-328, 1998.

Lewis, "Oncogenes Can Work Together to Increase Pathogenic Effects," Genetic Engineering News, 1992, 12(9):1.

Lewis, "PCR's Competitors Are Alive and Well and Moving Rapidly Towards Commercialization," Genetic Engineering News, 1992, vol. 12, 3 pages.

Li et al., "Angiotensin-(1-7) augments bradykinin-induced vasodilation by competing with ACE and releasing nitric oxide," *Hypertension*. Jan. 1997; 29(1 Pt 2):394-400.

Lim et al., "In-Vivo Evaluation of an in Situ Polymer Precipitation Delivery System for a Novel Natriuretic Peptide," PLoS One 8(2): e52484, Feb. 2013.

Lim et al., "Sustained delivery of a novel natriuretic peptide for three weeks with in situ polymer precipitation delivery system," *J Card Fail.*, 18(8):563, Aug. 2012 [abstract].

Lin et al., "Human Atrial Natriuretic Peptide Gene Delivery Reduces Blood Pressure in Hypertensive Rats," Hypertension, 1995, 26:847-853.

Lisy and Burnett, "The Design, Synthesis and Cardiorenal Actions of a New Chimeric Natriuretic Peptide CD-NP," *J. Am. Coll. Cardiol.*, 41(6 Suppl 1):312A, Abstract 860-1, 1 page, 2003.

Lisy et al., "A new natriuretic peptide present in canine plasma and heart," *Journal of Cardiac Failure*, 4 (3) Suppl. 1, Abstract No. Y3, p. 1, 1998.

Lisy et al., "Design, synthesis, and actions of a novel chimeric natriuretic peptide: CD-NP. ," J. Am. College Card., 52(1):60-68, Jul. 2008.

Lisy et al., "Renal actions of synthetic dendroaspis natriuretic peptide," *Kidney Int.*, Aug. 1999; 56(2):502-508.

Lisy et al., "Therapeutic Action of a New Natriuretic and Vasoactive Peptide DNP in Experimental Severe Congestive Heart Failure", Circulation, V. 100 (18) Supplement 1, Abstract No. 3354,(Nov. 2, 1999),pp. 1-636.

Lisy et al., "Therapeutic actions of a new synthetic vasoactive and natriuretic peptide, dendroaspis natriuretic peptide, in experimental severe congestive heart failure," Congestive Heart Failure, Hypertension, 37, Obtained from Chemical Abstracts, 135(2):130 Abstract 14664, Jul. 9, 2001, 3 pages.

Lisy et al., "Therapeutic actions of a new synthetic vasoactive and natriuretic peptide, dendroaspis natriuretic peptide, in experimental severe congestive heart failure," Hypertension., Apr. 2001; 37(4):1089-1094.

Lisy et al., "Unique Renal and Systemic Hemadynamic Action of a New Natriuretic Peptide in Experimental Heart Failure," JACC, Abstract No. 1199-17, p. 202A, Feb. 1999.

Lisy et al., "Design, synthesis and unique biological actions of CD-NP: A novel CNP-like chimeric natriuretic peptide," *Circulation*, 114(18)Suppl. S: 440, 2006.

Lisy et al., "Design, synthesis, and cardiorenal actions of a novel small natriuretic peptide: CT-DNP," *J Am Coll Cardiol.*, Feb. 1, 2005; 45(3):419A, Abstract 1128-120.

Lisy et al., "Renal actions of synthetic dendroaspis natriuretic peptide," Kidney Int., 1999, 56:502-508.

Lisy et al., "Therapeutic actions of a new synthetic vasoactive and natriuretic peptide, dendroaspis natriuretic peptide, in experimental severe congestive heart failure," Hypertension, 2001, 37:1089-1094.

Lloyd-Jones et al., "Lifetime risk for development of atrial fibrillation: The framingham heart study," Circulation, 110:1042-1046, 2004.

Longenecker et al., "Validation of comorbid conditions on the end-stage renal disease medical evidence report: the CHOICE study. Choices for Healthy Outcomes in Caring for ESRD," J. Am. Soc. Nephrol., 2000, 11:520-529.

Loot et al., "Angiotensin-(1-7) attenuates the development of heart failure after myocardial infarction in rats," *Circulation*. Apr. 2, 2002; 105(13):1548-1550.

Luchner et al., "Angiotensin II in the evolution of experimental heart failure," Hypertension, 28(3):472-477, Sep. 1996.

Lula et al., "Study of angiotensin-(1-7) vasoactive peptide and its beta-cyclodextrin inclusion complexes: complete sequence-specific NMR assignments and structural studies," *Peptides*, 28:2199-2210, Aug. 19, 2007.

Malik et al., "Recent advances in protein and peptide drug delivery systems," Curr Drug Deliv., 4(2):141-151, Apr. 2007.

Mangiafico et al., "Neutral endopeptidase inhibition and the natriuretic peptide system: an evolving strategy in cardiovascular therapeutics," Eur Heart J., 34(12):886-893c, Epub Aug. 31, 2012.

Mann, "Cardiac remodeling as therapeutic target: treating heart failure with Cardiac Support Devices," *Heart Failure Reviews*, 10(2):93-94, 2005.

Margulies and Burnett, "Inhibition of cyclic GMP phosphodiesterases augments renal responses to atrial natriuretic factor in congestive heart failure," *J. Cardiac Failure*, 1:71-80, 1994.

(56) References Cited

OTHER PUBLICATIONS

Margulies et al., "Angiotensin inhibition potentiates the renal responses to neutral endopeptidase inhibition in dogs with congestive heart failure," J. Clin. Invest., 88(5):1636-1642, Nov. 1991.

Margulies et al., "Induction and prevention of radiocontrast-induced nephropathy in dogs with heart failure," Kidney International, 1990, 38(6):1101-1108.

Marques et al., "An oral formulation of angiotensin-(1-7) produces cardioprotective effects in infarcted and isoproterenol-treated rats," *Hypertension*, 2011; 57:477-483.

Martin et al., "CD-NP: a novel engineered dual guanylyl cyclase activator with anti-fibrotic actions in the heart," PLoS One, 2012;7(12):e52422. Epub Dec. 18, 2012.

Martin et al., "Abstract 1484: New Insights into the Kidney-Heart Connection: Mild Renal Insufficiency Induces Cardiac Fibrosis and Diastolic Dysfunction Followed by Late Systolic Impairment," Circulation, 118:S_334-S_335, 2008.

Mathur et al., "Nesiritide—A new agent for acute decompensated heart failure," *Medical Journal of Armed Forces India*, 61(4): 375-376, 2005.

McCurley et al., "Furosemide and the progression of left ventricular dysfunction in experimental heart failure," J. Am. Coll. Cardiol., 2004, 44(6):1301-1307.

McDonagh et al., "Biochemical detection of left-ventricular systolic dysfunction," Lancet, 1998, 351:9-13.

McKie et al., "A human atrial natriuretic peptide gene mutation reveals a novel peptide with enhanced blood pressure-lowering, renal-enhancing, and aldosterone-suppressing actions," J Am Coll Cardiol., 54(11):1024-1032, Sep. 8, 2009.

McKie et al., "A novel atrial natriuretic peptide based therapeutic in experimental angiotensin II mediated acute hypertension," Hypertension, 56:1152-1159, 2010.

Mckie et al., "CD-NP: An innovative designer natriuretic peptide activator of particulate guanylyl cyclase receptors for cardiorenal disease," Curr. Heart Fail. Reports, 7(3):93-99, 2010.

Meienhofer, "Peptide Synthesis: a Review of the Solid-Phase Method," *Hormonal Proteins and Peptides*, vol. 2, Li (ed.), Academic Press, pp. 45-267, 1973.

Menon et al., "Angiotensin-(1-7) inhibits growth of human lung adenocarcinoma xenografts in nude mice through a reduction in cyclooxygenase-2," *Cancer Res*. Mar. 15, 2007; 67(6):2809-2815.

Mentzer, "Effects of perioperative nesiritide in patients with left ventricular dysfunction undergoing cardiac surgery:the NAPA Trial," J Am Coll Cardiol., Feb. 13, 2007; 49(6):716-726. Epub Dec. 11, 2006.

Merrifield, "Solid Phase Peptide Synthesis. I. The Synthesis of a Tetrapeptide," J. Am. Chem. Soc., 1963, 85:2149-2154.

Miller et al., "Amphiphilic Conjugates of Human Brain Natriuretic Peptide Designed for Oral Delivery: In Vitro Activity Screening," *Bioconjugate Chem*., 2006, 17:267-274.

Misono et al., "Rat atrial natriuretic factor: isolation, structure and biological activities of four major peptides," Biochem. Biophys. Res. Comm., 123(2):444-451, Sep. 1984.

Mitrovic et al., "Effects of the renal natriuretic peptide urodilatin (ularitide) in patients with decompensated chronic heart failure: a double-blind, placebo-controlled, ascending-dose trial," *Am. Heart J*., 150(6):1239, 2005.

Mitrovic et al., "Haemodynamic and clinical effects of ularitide in decompensated heart failure," Eur Heart J., 27(23):2823-2832, Epub Oct. 30, 2006.

Mizuiri et al., "Expression of ACE and ACE2 in individuals with diabetic kidney disease and healthy controls," *Am J Kidney Dis*., Apr. 2008; 51(4):613-623. Epub Mar. 4, 2008.

Moalem et al., "Atrial natriuretic peptide reverses the negative functional effects of stunning in rabbit myocardium," Regul Pept. Dec. 15, 2005; 132(1-3):47-52. Epub Oct. 11, 2005.

Molling, "Naked DNA for vaccine or therapy," J. Mol. Med., 1997, 75:242-246.

Morley, "Modulation of the action of regulatory peptides by structural modification," *Trends Pharm. Sci*., 1980, 463-468.

Mukoyama et al., "Brain natriuretic peptide as a novel cardiac hormone in humans Evidence for an exquisite dual natriuretic peptide system, atrial natriuretic peptide and brain natriuretic peptide," *J Clin Invest*. Apr. 1991; 87(4):1402-1412.

Mullis et al., "Specific Enzymatic Amplification of DNA In Vitro: The Polymerase Chain Reaction," Cold Spring Harbor Symp. Quant. Biol., 1986, 51:263-273.

Myakishev et al., "High-Throughput SNP Genotyping by Allele-Specific PCR with Universal Energy-Transfer-Labeled Primers," Genome Res., 11:163-169, 2001.

Naruko et al. "C-type natriuretic peptide and natriuretic peptide receptors are expressed by smooth muscle cells in the neointima after percutaneous coronary intervention," *Atherosclerosis*, 181(2):241-250, 2005.

Needleman and Wunsch, "A General Method Applicable to the Search for Similarities in the Amino Acid Sequence of Two Proteins," J. Mol. Biol., 1970, 48:443-453.

Newton-Cheh et al., "Association of common variants in NPPA and NPPB with circulating natriuretic peptides and blood pressure," Nat Genet., 41(3):348-353, Epub Feb. 15, 2009.

Ngo et al., "Computational Complexity, Protein Structure Prediction, and the Levinthal Paradox," The Protein Folding Problem and Tertiary Structure Prediction, Merz and Grand, Eds, Birkhauser, Boston, pp. 433-506, 1994.

Nicholls, "The natriuretic peptides in heart failure," J. Int. Med., 1994, 235:515-526.

Niederkofler et al., "Detection of endogenous b-type natriuretic peptide at very low concentrations in patients with heart failure," Circ Heart Fail., 1(4):258-264, Epub Oct. 14, 2008.

Nieminen et al., "Executive summary of the guidelines on the diagnosis and treatment of acute heart failure: the Task Force on Acute Heart Failure of the European Society of Cardiology," Eur Heart J., 26(4):384-416, Epub Jan. 28, 2005.

Nir et al., "CNP is present in canine renal tubular cells and secreted by cultured opossum kidney cells," *Am J Physiol*. Dec. 1994; 267(6 Pt 2):R1653-R1657.

Nishida et al., "Effects of brain natriuretic peptide on hemodynamics and renal function in dogs," Jpn J Physiol., 40(4):531-540, 1990.

Nomura et al., "Multicenter prospective investigation on efficacy and safety of carperitide as a first-line drug for acute heart failure syndrome with preserved blood pressure: COMPASS: Carperitide Effects Observed Through Monitoring Dyspnea in Acute Decompensated Heart Failure Study," Circ J., 72(11):1777-1786, Epub Oct. 3, 2008.

O'Connor et al., "Effect of nesiritide in patients with acute decompensated heart failure," N Engl J Med., 365(1):32-43, Jul. 7, 2011.

Ogawa et al., "Crystal Structure of Hormone-bound Atrial Natriuretic Peptide Receptor Extracellular Domain," J Biol Chem, 2004, 279(27):28625-28631.

Ogawa et al., "Molecular cloning of the complementary DNA and gene that encode mouse brain natriuretic peptide and generation of transgenic mice that overexpress the brain natriuretic peptide gene," J. Clin. Invest., 1994, 93(5):1911-1921.

Ogawa et al., "Human c-type natriuretic peptide, characterization of the gene and peptide," Hypertension, 1992, 19:809-813.

Okawa et al., "Preischemic infusion of alpha-human atrial natriuretic peptide elicits myoprotective effects against ischemia reperfusion in isolated rat hearts," *Mol Cell Biochem*. Jun. 2003; 248(1-2):171-177.

Okolicany et al. "Clearance receptor and neutral endopeptidase-mediated metabolism of atrial natriuretic factor," Am J Physiol Renal Physiol, 1992, 263:F546-F553.

Olson et al., "Kv1.5 channelopathy due to KCNA5 loss-of-function mutation causes human atrial fibrillation," Hum. Mol. Genet., 15:2185-2191, 2006.

Olson et al., "Sodium channel mutations and susceptibility to heart failure and atrial fibrillation," JAMA, 293:447-454, 2005.

Osman et al., "Molecular identification and immunohistochemical localization of atrial natriuretic peptide in the heart of the dromedary camel (*Camelus dromedarius*)" *Comp Biochem Physiol a Mol Integr Physiol*., 139(4):417-424, Dec. 2004.

(56) References Cited

OTHER PUBLICATIONS

Owan et al., "The effects of nesiritide on renal function and diuretic responsiveness in acutely decompensated heart failure patients with renal dysfunction," *J Card Fail.*, May 2008; 14(4):267-275.
Padilla et al., "Intravenous administration of the natriuretic peptide urodilatin at low doses during coronary reperfusion limits infarct size in anesthetized pigs," *Cardiovasc Res.* Aug. 15, 2001; 51(3):592-600.
Pagel-Langenickel et al., "Natriuretic peptide receptor B signaling in the cardiovascular system: protection from cardiac hypertrophy," *J Mol Med* (Berl). Aug. 2007; 85(8):797-810. Epub Apr. 12, 2007.
Pan et al., "Biodesign of a renal-protective peptide based on alternative splicing of B-type natriuretic peptide," *Proc Natl Acad Sci U S A.*, 106(27):11282-11287, Epub Jun. 18, 2009.
Pan et al., "Interplay of angiotensin II and angiotensin(1-7) in the regulation of matrix metalloproteinases of human cardiocytes," *Exp Physiol.* May 2008; 93(5):599-612. Epub Feb. 2008.
Pan et al., "Alternatively spliced forms of human BNP: Discovery, localization, and function," *Circulation*, vol. 110, No. 17, Suppl. III, p. III-96, Abstract 452, Oct. 26, 2004.
Pardoll and Beckerleg, "Exposing the Immunology of Naked DNA Vaccines," *Immunity*, 1995, 3:165-169.
Park et al., "Therapeutic potential of atrial natriuretic peptide administration on peripheral arterial diseases," *Endocrinology.* Feb. 2008; 149(2):483-491. Epub Nov. 8, 2007.
Pawson et al., "Assembly of cell regulatory systems through protein interaction domains," Science, 2003, 300:445-452.
Peacock, "The B-type natriuretic peptide assay: a rapid test for heart failure," Cleve. Clin. J. Med., 2002, 69(3):243-251.
Pearson and Lipman, "Improved tools for biological sequence comparison," Proc. Natl. Acad. Sci, USA, 1988, 85:2444-2448.
Peiró et al., "Endothelial dysfunction through genetic deletion or inhibition of the G protein-coupled receptor Mas: a new target to improve endothelial function," *J Hypertens.* Dec. 2007; 25(12):2421-2425.
Pörsti et al., "Release of nitric oxide by angiotensin-(1-7) from porcine coronary endothelium: implications for a novel angiotensin receptor," *Br J Pharmacol.* Mar. 1994; 111(3):652-654.
Potter et al., "Natriuretic peptides, their receptors, and cyclic guanosine monophosphate-dependent signaling functions," *Endocr Rev.*, Feb. 2006; 27(1):47-72. Epub Nov. 16, 2005.
Potter, "Natriuretic peptide metabolism, clearance and degradation," FEBS J., 278(11):1808-1817, Epub Apr. 7, 2011.
Prausnitz, "A peptide chaperone for transdermal drug delivery," Nat Biotechnol., 24(4):416-417, Apr. 2006.
Preston et al., "Synergistic effects of ANP and sildenafil on cGMP levels and amelioration of acute hypoxic pulmonary hypertension," *Exp. Bio. Med.*, 229:920-925, 2004.
Prince et al., "Robust and accurate single nucleotide polymorphism genotyping by dynamic allele-specific hybridization (DASH): design criteria and assay validation," Genome Res., 11:152-162, 2001.
Publication Committee for the VMAC Investigators, "Intravenous nesiritide vs nitroglycerin for treatment of decompensated congestive heart failure: a randomized controlled trial," *JAMA.* Mar. 27, 2002; 287(12):1531-1540; Erratum in *JAMA* Aug. 7, 2002; 288(5):577.
PubMed search for atrial natriuretic peptide; Nov. 24, 2009; 5 pages.
PubMed search for brain natriuretic peptide; Nov. 24, 2009; 3 pages.
PubMed search for C-type natriuretic peptide; Nov. 24, 2009; 4 pages.
PubMed search for DNP; Nov. 24, 2009; 4 pages.
Ralat et al., "Insulin-degrading enzyme modulates the natriuretic peptide-mediated signaling response," J Biol Chem., 286(6):4670-4679. Epub Nov. 22, 2010.
Rastegar et al., "Atrial natriuretic peptide reduces the severe consequences of coronary artery occlusion in anaesthetized dogs," *Cardiovasc Drugs Ther.* Oct. 2000; 14(5):471-479.
Redfield et al., "Cardiorenal and Neurohumoral Function in a Canine Model of Early Left Ventricular Dysfunction," Circulation, 1993, 87:2016-2022.

Remuzzi et al., "Nephropathy in Patients with Type 2 Diabetes," N. Engl. J. Med., 2002, 346(15):1145-1151.
Ren et al., "Brain natriuretic peptide limits myocardial infarct size dependent of nitric oxide synthase in rats," *Clin Chim Acta.* Feb. 2007; 377(1-2):83-87. Epub Oct. 5, 2006.
Ren et al., "Vasodilator action of angiotensin-(1-7) on isolated rabbit afferent arterioles," *Hypertension.* Mar. 1, 2002; 39(3):799-802.
Richards et al., "Atrial natriuretic hormone has biological effects in man at physiological plasma concentrations," *J. Clin. Endo. Metab.*, 67(6):1134-1139, 1988.
Richards et al., "BNP in hormone-guided treatment of heart failure," *Trends Endocrinol. Metab.*, (5):151-155, 2002.
Rose and Giles, "Natriuretic peptide C receptor signaling in the heart and vasculature," J Physiol, 2008, 586(2):353-366.
Rose et al., "C-type natriuretic peptide activates a non-selective cation current in acutely isolated rat cardiac fibroblasts via natriuretic peptide C receptor-mediated signaling," J. Physiol., 2007, 580(Pt. 1):255-274.
Rossi et al., "Natriuretic peptide levels in atrial fibrillation: a prospective hormonal and Doppler-echocardiographic study," J. Am. Coll. Cardiol., 35(5):1256-1262, 2000.
Sabbatini et al., "Atrial natriuretic factor stimulates exocrine pancreatic secretion in the rat through NPR-C receptors," Am. J. Physiol. Gastrointest. Liver Physiol., 2003, G929-G937.
Sabbatini et al., "C-type natriuretic peptide stimulates pancreatic exocrine secretion in the rat: Role of vegal afferent and efferent pathways," Eur. J. Pharmacol., 2007, 577:192-202.
Sabrane et al., "Vascular endothelium is critically involved in the hypotensive and hypovolemic actions of atrial natriuretic peptide," J Clin Invest., 115(6):1666-1674, Jun. 2005.
Sackner-Bernstein et al., "Risk of Worsening Renal Function With Nesiritide in Patients With Acutely Decompensated Heart Failure," Circulation, 2005, 111:1487-1491.
Sagnella, "Practical implications of current natriuretic peptide research," J. Renin. Angiotensin Aldosterone Syst., 2000, 1(4):304-315.
Sampaio et al., "Systemic and regional hemodynamic effects of angiotensin-(1-7) in rats," *Am J Physiol Heart Circ Physiol.*, Jun. 2003; 284(6):H1985-H1994. Epub Feb. 6, 2003.
Sancho and Haber, "A direct microassay for aldosterone in plasma extracts," *J. Clin. Endocrinol. Metab.*, 47(2):391-396, Aug. 1978.
Sangawa et al., "Atrial natriuretic peptide protects against ischemia-reperfusion injury in the isolated rat heart," *Ann Thorac Surg.* Jan. 2004; 77(1):233-237.
Santiago et al., "Lifetime overproduction of circulating Angiotensin-(1-7) attenuates deoxycorticosterone acetate-salt hypertension-induced cardiac dysfunction and remodeling," *Hypertension*, 55(4):889-896, Epub Mar. 8, 2010.
Santos et al., "Angiotensin-(1-7) is an endogenous ligand for the G protein-coupled receptor Mas," *Proc Natl Acad Sci U S A.* Jul. 8, 2003; 100(14):8258-8263. Epub Jun. 26, 2003.
Santos et al., "Mas deficiency in FVB/N mice produces marked changes in lipid and glycemic metabolism," *Diabetes.* Feb. 2008; 57(2):340-347. Epub Nov. 19, 2007.
Santos et al., "Recent advances in the angiotensin-converting enzyme 2-angiotensin(1-7)-Mas axis," *Exp Physiol.* May 2008; 93(5):519-527. Epub Feb. 29, 2008.
Sarzani et al., "Renin-angiotensin system, natriuretic peptides, obesity, metabolic syndrome, and hypertension: an integrated view in humans," *J Hypertens.* May 2008; 26(5):831-843.
Sato et al., "Continuous low-dose human atrial natriuretic peptide promotes diuresis in oliguric patients after living donor liver transplantation," *Transplant Proc.*, Dec. 2006; 38(10):3591-3593.
Scarborough et al., "Truncated atrial natriuretic peptide analogs. Comparison between receptor binding and stimulation of cyclic GMP accumulation in cultured vascular smooth muscle cells," J Biol Chem, 1986, 261(28):12960-12964.
Schafer and Hawkins, "DNA variation and the future of human genetics," Nat. Biotechnol., 16:33-39, 1998.
Schiavone et al., "Release of vasopressin from the rat hypothalamo-neurohypophysial system by angiotensin-(1-7) heptapeptide," *Proc Natl Acad Sci U S A.* Jun. 1988; 85(11):4095-4098.

(56) References Cited

OTHER PUBLICATIONS

Schiller et al., "Synthesis of side-chain to side-chain cyclized peptide analogs on solid supports," *Int J Pept Protein Res*, 25:171-177, 1985.
Schiller et al., "A novel cyclic opioid peptide analog showing high preference for μ-receptors," *Biochem. Biophy. Res. Comm.*, Mar. 1985, 127:558-564.
Schirger et al., "Presence of Dendroaspis Natriuretic Peptide-Like Immunoreactivity in Human Plasma and Its Increase During Human Heart Failure," *Mayo Clin. Proc.*, 1999, 74:126-130.
Schirger et al., "Vascular actions of brain natriuretic peptide: modulation by atherosclerosis and neutral endopeptidase inhibition," *J. Am. Coll. Cardiol.*, 2000, 35:796-801.
Schoenfeld et al., "Agonist selectivity for three species of natriuretic peptide receptor-A," *Mol Pharmacol*, 47(1):172-180, 1995.
Schulz-Knappe et al., "Isolation and structural analysis of "urodilatin", a new peptide of the cardiodilatin-(ANP)-family, extracted from human urine," *Klin Wochenschr*. Sep. 1, 1988;.66(17):752-759.
Schweitz et al., "A new member of the natriuretic peptide family is present in the venom of the green mamba (Dendroaspis angusticeps)." *J Biol Chem*. Jul. 15, 1992; 267(20):13928-13932.
Scotland et al., "C-type natriuretic peptide inhibits leukocyte recruitment and platelet-leukocyte interactions via suppression of P-selectin expression," *Proc Natl Acad Sci USA*. Oct. 4, 2005; 102(40):14452-14457. Epub Sep. 22, 2005.
Sezai et al., "Efficacy of continuous low-dose hANP administration in patients undergoing emergent coronary artery bypass grafting for acute coronary syndrome," *Circ J.*, Sep. 2007; 71(9):1401-1407.
Sezai et al., "Efficacy of continuous low-dose human atrial natriuretic peptide given from the beginning of cardiopulmonary bypass for thoracic aortic surgery," *Surg Today*. 2006; 36(6):508-514.
Sezai et al., "Low-dose continuous infusion of human atrial natriuretic peptide during and after cardiac surgery," *Ann Thorac Surg*. Mar. 2000; 69(3):732-738.
Short Protocols in Molecular Biology, Chapter 11, Green Publishing Associates and John Wiley & Sons, Ed. Ausubel et al., 1992.
Short Protocols in Molecular Biology, Chapter 8, Green Publishing Associates and John Wiley & Sons, edited by Ausubel et al., 1992.
Silver, "The natriuretic peptide system: kidney and cardiovascular effects," *Curr Opin Nephrol Hypertens*. Jan. 2006; 15(1):14-21.
Singh et al., "Novel snake venom ligand dendroaspis natriuretic peptide is selective for natriuretic peptide receptor-A in human heart: downregulation of natriuretic peptide receptor-A in heart failure," *Circ Res*. Jul. 21, 2006; 99(2):183-90. Epub Jun. 15, 2006.
Skrzypiec-Spring et al., "Isolated heart perfusion according to Langendorff—still viable in the new millennium," *J Pharmacol Toxicol Methods*. Mar.-Apr. 2007; 55(2):113-26. Epub May 26, 2006.
Smith and Waterman, "Comparison of Biosequences," *Adv. Appl. Math.*, 1981, 2:482-489.
Soeki et al., "C-type natriuretic peptide, a novel antifibrotic and antihypertrophic agent, prevents cardiac remodeling after myocardial infarction," *J Am Coll Cardiol.*, Feb. 15, 2005; 45(4):608-616.
Spatola et al., "Structure-activity relationships of enkephalins containing serially replaced thiomethylene amide bond surrogates," *Life Sci.*, Apr. 1986, 38:1243-1249.
Spatola, "Peptide backbone modifications: a structure-activity analysis of peptides containing amino bond surrogates, conformational constraints, and related backbone replacements," *Chemistry and Biochemistry of Amino Acid Peptides and Proteins*, B. Weinstein, ed., Marcel Dekker, New York, 1983, Chapt. 5, p. 267 [Table of Contents].
Spatola, Vega Data vol. 1, No. 3, pp. 267-268, 1983.
Stein and Levin, "Natriuretic peptides: physiology, therapeutic potential, and risk stratification in ischemic heart disease," *Am Heart J.*, 135(5 Pt 1):914-923, May 1998.
Steiner et al., "Pulmonary hypertension: inhaled nitric oxide, sildenafil and natriuretic peptides," *Curr Opin Pharmacol.*, 5(3):245-250, Jun. 2005.
Steiner et al., "Radioimmunoassay for cyclic nucleotides. I. Preparation of antibodies and iodinated cyclic nucleotides," *J Biol Chem.*, Feb. 25, 1972; 247(4):1106-1113.
Steiner et al., "The measurement of cyclic nucleotides by radioimmunoassay," Adv. Biochem. Psychopharmacol., 3:89-111, 1970.
Stevens et al., "A Functional Role for Endogenous Atrial Natriuretic Peptide in a Canine Model of Early Left Ventricular Dysfunction," J. Clin. Invest., 1995, 95:1101-1108.
Stevens et al., "A Modified Model of Tachycardia-Induced Cardiomyopathy: Insights into Humoral and Renal Adaptations," Pathophysiology of Tachycardia-Induced Heart Failure, 1996, Futura Publishing Co., Inc. NY, pp. 133-151.
Stevenson et al., "Idiotypic DNA Vaccines Against B-cell Lymphoma," Immunol. Rev., 1995, 145:211-228.
Stingo et al., "Cardiovascular and renal actions of C-type natriuretic peptide," *Am J Physiol.*, Jan. 1992; 262(1 Pt 2):H308-H312.
Stingo et al., "Presence of C-type natriuretic peptide in cultured human endothelial cells and plasma," *Am J Physiol*. Oct. 1992; 263(4 Pt 2):H1318-H1321.
Stoneking et al., "Population variation of human mtDNA control region sequences detected by enzymatic amplification and sequence-specific oligonucleotide probes," Am. J. Hum. Genet., 48:370-382, 1991.
Su et al., "Angiotensin-(1-7) inhibits angiotensin II-stimulated phosphorylation of MAP kinases in proximal tubular cells," *Kidney Int.* Jun. 2006; 69(12):2212-2218. Epub May 3, 2006.
Sudoh et al., "A new natriuretic peptide in porcine brain," *Nature*. Mar. 3, 1988; 332(6159):78-81.
Sudoh et al., "C-type natriuretic peptide (CNP): a new member of natriuretic peptide family identified in porcine brain," *Biochem Biophys Res Commun*. Apr. 30, 1990; 168(2):863-870.
Suga et al., "Endothelial production of C-type natriuretic peptide and its marked augmentation by transforming growth factor-beta. Possible existence of vascular natriuretic peptide system," *J Clin Invest*. Sep. 1992; 90(3):1145-1149.
Suga et al., "Receptor selectivity of natriuretic peptide family, atrial natriuretic peptide, brain natriuretic peptide, and C-type natriuretic peptide," *Endocrinology*. Jan. 1992; 130(1):229-239.
Summerton and Weller, "Morpholino antisense oligomers: design, preparation, and properties," Antisense Nucleic Acid Drug Dev., 1997, 7:187-195.
Supaporn et al., "Blunted cGMP response to agonists and enhanced glomerular cyclic 3',5'-nucleotide phosphodiesterase activities in experimental congestive heart failure," *Kidney Int.*, 50(5):1718-1725, Nov. 1996.
Suwa et al., "Multicenter prospective investigation on efficacy and safety of carperitide for acute heart failure in the 'real world' of therapy," *Circ J.*, Mar. 2005; 69(3):283-290.
Suzuki et al., "The role of the natriuretic peptides in the cardiovascular system," Cardiovascular Res., 2001, 51:489-494.
Takagi et al., "Alpha-human atrial natriuretic peptide, carperitide, reduces infarct size but not arrhythmias after coronary occlusion/reperfusion in dogs," *J Cardiovasc Pharmacol*. Jul. 2000; 36(1):22-30.
Takata et al., "The beneficial effect of atrial natriuretic peptide on arrhythmias and myocardial high-energy phosphates after reperfusion," Cardiovascular Res., 32:286-293, 1996.
Tallant et al., "Angiotensin-(1-7) inhibits growth of cardiac myocytes through activation of the mas receptor," *Am J Physiol Heart Circ Physiol*. Oct. 2005; 289(4):H1560-H1566. Epub Jun. 10, 2005.
Talwar et al., "Plasma cardiotrophin-1 following acute myocardial infarction: relationship with left ventricular systolic dysfunction," *Clin Sci (Lond).*, 102(1):9-14, Jan. 2002.
Tawaragi et al., "Gene and precursor structures of human C-type natriuretic peptide," *Biochem Biophys Res Commun.*, Mar. 15, 1991; 175(2):645-651.
Teixeira et al., "Differential effects of the phosphodiesterase type 5 inhibitors sildenafil, vardenafil, and tadalafil in rat aorta," *J Pharmacol Exp Ther.*, 316(2):654-661. Epub Oct. 4, 2005.
Trask and Ferrario, "Angiotensin-(1-7): pharmacology and new perspectives in cardiovascular treatments," *Cardiovasc Drug Rev*. 2007 Summer; 25(2):162-174.

(56) References Cited

OTHER PUBLICATIONS

Tremblay et al., "Biochemistry and physiology of the natriuretic peptide receptor guanylyl cyclases," *Mol Cell Biochem.*, 230(1-2):31-47, Jan. 2002.
Tripathy et al, "Immune responses to transgene-encoded proteins limit the stability of gene expression after injection of replication-defective adenovirus vectors," Nature Med., 1996, 2:545-550.
Tripathy et al., "Long-term expression of erythropoietin in the systemic circulation of mice after intramuscular injection of a plasmid DNA vector," Proc. Natl. Acad. Sci. USA, 1996, 93:10876-10880.
Tripathy et al., "Stable delivery of physiologic levels of recombinant erythropoietin to the systemic circulation by intramuscular injection of replication-defective adenovirus," Proc. Natl. Acad. Sci. USA, 1994, 91:11557-11561.
Tsuruda et al., "Cardiotrophin-1 Stimulation of Cardiac Fibroblast Growth : Roles for Glycoprotein 130/Leukemia Inhibitory Factor Receptor and the Endothelin Type A Receptor," Circ. Res., 2002, 90:128-134.
Tsuruda et al., "Brain Natriuretic Peptide Is Produced in Cardiac Fibroblasts and Induces Matrix Metalloproteinases," *Circ. Res.* 2002; 91:1127-1134.
Tsurumi et al., "Direct Intramuscular Gene Transfer of Naked DNA Encoding Vascular Endothelial Growth Factor Augments Collateral Development and Tissue Perfusion," Circulation, 1996, 94:3281-3290.
Ueda et al., "Angiotensin(1-7) potentiates bradykinin-induced vasodilatation in man," *J Hypertens.*, 19(11):2001-2009, Nov. 2001.
Underhill et al., "Detection of numerous Y chromosome biallelic polymorphisms by denaturing high-performance liquid chromatography," Genome Res., 7:996-1005, 1997.
Valli et al., "Review of 10 years of the clinical use of brain natriuretic peptide in cardiology," *J. Lab. Clin. Med.*, 134(5):437-444, 1999.
Van den Berg et al., "Depletion of atrial natriuretic peptide during longstanding atrial fibrillation," Europace, 6(5):433-437, 2004.
Veronese and Mero, "The impact of PEGylation on biological therapies," *BioDrugs.*, 2008; 22(5):315-329.
Veronese and Pasut, "PEGylation, successful approach to drug delivery," *Drug Discov. Today*, Nov. 1, 2005; 10(21):1451-1458.
Vesely et al, "Elimination of up to 80% of human pancreatic adenocarcinomas in athymic mice by cardiac hormones," *In Vivo.* May-Jun. 2007; 21(3):445-451.
Vesely et al., "Five cardiac hormones decrease the number of human small-cell lung cancer cells," *Eur J Clin Invest.* Jun. 2005; 35(6):388-398.
Vesely et al., "Four cardiac hormones cause cell death of melanoma cells and inhibit their DNA synthesis.," *Am J Med Sci.* Nov. 2007; 334(5):342-349.
Vesely et al., "Four cardiac hormones eliminate up to two-thirds of human breast cancers in athymic mice," In Vivo. Nov.-Dec. 2007; 21(6):973-978.
Vesely et al., "Four peptide hormones decrease the number of human breast adenocarcinoma cells," *Eur J Clin Invest.* Jan. 2005; 35(1):60-69.
Vesely et al., "Urodilatin and four cardiac hormones decrease human renal carcinoma cell numbers," *Eur J Clin Invest.* Nov. 2006; 36(11):810-819.
Vesely, "Natriuretic peptides and acute renal failure," Am. J. Physiol. Renal. Physiol. 2003, 285: F137-F177.
Vesely, "Atrial natriuretic peptides in pathophysiological diseases," Cardiovascular research, 51: 647-658, 2001.
Vieira and Messing, "Production of Single-Stranded Plasmid DNA," Meth. Enzymol., 1987, 153:3-11.
Villar et al., "Definitive role for natriuretic peptide receptor-C in mediating the vasorelaxant activity of C-type natriuretic peptide and endothelium-derived hyperpolarising factor," *Cardiovasc Res.* Jun. 1, 2007; 74(3):515-25. Epub Mar. 3, 2007.

Von Geldern et al., "Small Atrial Natriuretic Peptide Analogues: Design, Synthesis, and Structural Requirements for Guanylate Cyclase Activation," *J. Med. Chem.*, 35:808-816, 1992.
Wakui, "Experimental study on myocardial protection by adjunct use of carperitide (hANP) in cardiac surgery," *Ann Thorac Cardiovasc Surg.* Feb. 2005; 11(1):12-20.
Walther et al., "Natriuretic peptide system in fetal heart and circulation," *J. Hypertens.*, 20(5):786-791, 2002.
Wang et al, "A single amino acid determines lysophospholipid specificity of the S1P1 (EDG1) and LPA1 (EDG2) phospholipid growth factor receptors," J. Biol Chem., 276(52):49213-49220, Epub Oct. 16, 2001.
Wang et al., "AlbuBNP, a recombinant B-type natriuretic peptide and human serum albumin fusion hormone, as a long-term therapy of congestive heart failure," Phare Res., 21(11):2105-2111, Nov. 2, 2004.
Wang et al., "Chronic administration of angiotensin-(1-7) attenuates pressure-overload left ventricular hypertrophy and fibrosis in rats," *Di Yi Jun Yi Da Xue Xue Bao.* May 2005; 25(5):481-487.
Wang et al., "AlbuBNP, a recombinant B-type natriuretic peptide and human serum albumin fusion hormone, as a long-term therapy of congestive heart failure," *Pharm Res.*, Nov. 2004; 21(11):2105-2111.
Wei et al. "Atrial and pulmonary endothelin mRNA is increased in a canine model of chronic low cardiac output," *Am. J. Physiol.*, 273:R838-R844, 1997.
Wei et al., "Action of C-type natriuretic peptide in isolated canine arteries and veins," *Am J Physiol.* Jan. 1993; 264(1 Pt 2):H71-H73.
Wei et al., "Angiotensin peptides modulate bradykinin levels in the interstitium of the dog heart in vivo," *J Pharmacol Exp Ther.* Jan. 2002; 300(1):324-329.
Wei et al., "Natriuretic Peptide System in Human Heart Failure," *Circulation*, 88:1004-1009, 1993.
Wei et al., "Vasonatrin peptide: a unique synthetic natriuretic and vasorelaxing peptide," *J Clin Invest.*, Oct. 1993; 92(4):2048-2052.
Wei et al., "Action of c-type natriuretic peptide in isolated canine arteries and veins," *Am. J. Physiol.*, 264:H71-H73, 1993.
Weiss, "Hot prospect for new gene amplifier," *Science.* Nov. 29, 1991; 254(5036):1292-1293.
Wells, "Additivity of mutational effects in proteins," Biochemistry, 29(37):8509-8517, Sep. 18, 1990.
Wennberg et al., "Inhibition of Nitric Oxide (NO), but not Neutral Endopeptidase (NEP), Augments , CNP-mediated Coronary Relaxation in CHF," Am. Coll. Cardiol., 1997, 29:305A.
Wermeling et al. "Microneedles permit transdermal delivery of a skin-impermeant medication to humans," Proc. Natl. Acad. Sci. USA, 2008, 105:2058-2063.
Wolff et al., "Direct Gene Transfer into Mouse Muscle in Vivo," Science, 1990, 247:1465-1468.
Wozakowska-Kaplon. "ANP and B-type peptide: Twins or kins? A different predictive value in atrial fibrillation Natriuretic peptides: Useful biomarkers in predicting the possibility of restoration and maintenance of sinus rhythm in patients with atrial fibrillation undergoing cardioversion," J Cardiology, 145 (2):234-235, 2010.
Xu et al., "Endothelial dysfunction and elevated blood pressure in MAS gene-deleted mice," *Hypertension.* Feb. 2008; 51(2):574-580, Epub Jan. 7, 2008.
Yamamoto et al., "Effect of endogenous natriuretic peptide system on ventricular and coronary function in failing heart," Am. J. Physiol., 1997, 273:H2406-H2414.
Yamamoto et al., "Ventricular remodeling during development and recovery from modified tachycardia-induced cardiomyopathy model," Am. J. Physiol., 1996, 271:R1529-R1532.
Yan et al., "Corin, a mosaic transmembrane serine protease encoded by a novel cDNA from human heart," J Biol Chem., 274(21):14926-14935, May 21, 1999.
Yan et al., "Corin, a transmembrane cardiac serine protease, acts as a pro-atrial natriuretic peptide-converting enzyme," Proc Natl Acad Sci U S A., 97(15):8525-8529, Jul. 18, 2000.
Yang et al., "Atrial natriuretic peptide administered just prior to reperfusion limits infarction in rabbit hearts," *Basic Res Cardiol.* Jul. 2006; 101(4):311-318. Epub Apr. 8, 2006.

(56) References Cited

OTHER PUBLICATIONS

Yang et al., "Developing particle-mediated gene-transfer technology for research into gene therapy of cancer," Mol. Med. Today, 1996, 2:476-481.
Yellon and Hausenloy, "Myocardial reperfusion injury," *N Engl J Med.* Sep. 13, 2007; 357(11):1121-1135.
Zhao et al., "Beneficial Effects of Phosphodiesterase 5 Inhibition in Pulmonary Hypertension are Influenced by Natriuretic Peptide Activity," Circulation, 2003, 107:234-237.
Zierer et al., "Potential renal protective benefits of intra-operative BNP infusion during cardiac transplantation," *Transplant Proc.* Dec. 2006; 38(10):3680-3684.
European Search Report for Application No. 12828994.9 dated Jan. 26, 2015, 8 pages.
Extended European Search Report for Application No. 12828994.9, dated Jun. 8, 2015, 11 pages.
International Preliminary Report on Patentability for PCT/US2012/051734, dated Mar. 13, 2014, 9 pages.
International Search Report and Written Opinion in International Application No. PCT/US2012/051734, dated Oct. 25, 2012, 16 pages.

```
                        SEQUENCE LISTING

<160> NUMBER OF SEQ ID NOS: 61

<210> SEQ ID NO 1
    <211> LENGTH: 7
    <212> TYPE: PRT
    <213> ORGANISM: Homo sapiens

<400> SEQUENCE: 1

Asp Arg Val Tyr Ile His Pro
    1               5

<210> SEQ ID NO 2
    <211> LENGTH: 6
    <212> TYPE: PRT
    <213> ORGANISM: Homo sapiens

<400> SEQUENCE: 2

Ser Leu Arg Arg Ser Ser
    1               5

<210> SEQ ID NO 3
    <211> LENGTH: 17
    <212> TYPE: PRT
    <213> ORGANISM: Homo sapiens

<400> SEQUENCE: 3

Cys Phe Gly Gly Arg Met Asp Arg Ile Gly Ala Gln Ser Gly Leu Gly
    1               5                   10                  15

Cys

<210> SEQ ID NO 4
    <211> LENGTH: 9
    <212> TYPE: PRT
    <213> ORGANISM: Homo sapiens

<400> SEQUENCE: 4

Ser Pro Lys Met Val Gln Gly Ser Gly
    1               5

<210> SEQ ID NO 5
    <211> LENGTH: 17
    <212> TYPE: PRT
    <213> ORGANISM: Homo sapiens

<400> SEQUENCE: 5

Cys Phe Gly Arg Lys Met Asp Arg Ile Ser Ser Ser Ser Gly Leu Gly
    1               5                   10                  15
```

Cys

<210> SEQ ID NO 6
<211> LENGTH: 5
<212> TYPE: PRT
<213> ORGANISM: Homo sapiens

<400> SEQUENCE: 6

Gly Leu Ser Lys Gly
1               5

<210> SEQ ID NO 7
<211> LENGTH: 17
<212> TYPE: PRT
<213> ORGANISM: Homo sapiens

<400> SEQUENCE: 7

Cys Phe Gly Leu Lys Leu Asp Arg Ile Gly Ser Met Ser Gly Leu Gly
1               5                   10                  15

Cys

<210> SEQ ID NO 8
<211> LENGTH: 6
<212> TYPE: PRT
<213> ORGANISM: Dendroaspis angusticeps

<400> SEQUENCE: 8

Glu Val Lys Tyr Asp Pro
1               5

<210> SEQ ID NO 9
<211> LENGTH: 17
<212> TYPE: PRT
<213> ORGANISM: Dendroaspis angusticeps

<400> SEQUENCE: 9

Cys Phe Gly His Lys Ile Asp Arg Ile Asn His Val Ser Asn Leu Gly
1               5                   10                  15

Cys

<210> SEQ ID NO 10
<211> LENGTH: 10
<212> TYPE: PRT
<213> ORGANISM: Homo sapiens

<400> SEQUENCE: 10

Thr Ala Pro Arg Ser Leu Arg Arg Ser Ser
1               5                   10

<210> SEQ ID NO 11
<211> LENGTH: 17
<212> TYPE: PRT
<213> ORGANISM: Homo sapiens

<400> SEQUENCE: 11

Cys Phe Gly Gly Arg Met Asp Arg Ile Gly Ala Gln Ser Gly Leu Gly
1               5                   10                  15

Cys

<210> SEQ ID NO 12
<211> LENGTH: 5
<212> TYPE: PRT
<213> ORGANISM: Homo sapiens

```
<400> SEQUENCE: 12

Asn Ser Phe Arg Tyr
1               5

<210> SEQ ID NO 13
<211> LENGTH: 6
<212> TYPE: PRT
<213> ORGANISM: Homo sapiens

<400> SEQUENCE: 13

Lys Val Leu Arg Arg His
1               5

<210> SEQ ID NO 14
<211> LENGTH: 10
<212> TYPE: PRT
<213> ORGANISM: Homo sapiens

<400> SEQUENCE: 14

Asp Arg Val Tyr Ile His Pro Phe His Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic peptide

<400> SEQUENCE: 15

Ser Ala Pro Arg Ser Leu Arg Arg Ser Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic peptide

<400> SEQUENCE: 16

Thr Val Pro Arg Ser Leu Arg Arg Ser Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic peptide

<400> SEQUENCE: 17

Thr Ala Gly Arg Ser Leu Arg Arg Ser Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic peptide

<400> SEQUENCE: 18

Thr Ala Pro Lys Ser Leu Arg Arg Ser Ser
1               5                   10
```

```
<210> SEQ ID NO 19
<211> LENGTH: 6
<212> TYPE: PRT
<213> ORGANISM: Artificial Sequence
<220> FEATURE:
<223> OTHER INFORMATION: synthetic peptide

<400> SEQUENCE: 19

Thr Leu Arg Arg Ser Ser
1               5

<210> SEQ ID NO 20
<211> LENGTH: 6
<212> TYPE: PRT
<213> ORGANISM: Artificial Sequence
<220> FEATURE:
<223> OTHER INFORMATION: synthetic peptide

<400> SEQUENCE: 20

Ser Ile Arg Arg Ser Ser
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic peptide

<400> SEQUENCE: 21

Ser Leu Lys Arg Ser Ser
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide

<400> SEQUENCE: 22

Ser Leu Arg Lys Ser Ser
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic peptide

<400> SEQUENCE: 23

Lys Val Leu Arg Arg Arg
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic peptide

<400> SEQUENCE: 24

Lys Val Leu Arg Lys His
1               5
```

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25

Lys Val Leu Lys Arg His
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic peptide

<400> SEQUENCE: 26

Lys Val Ile Arg Arg His
1               5

<210> SEQ ID NO 27
<211> LENGTH: 12
<212> TYPE: PRT
<213> ORGANISM: Artificial Sequence
<220> FEATURE:
<223> OTHER INFORMATION: synthetic peptide

<400> SEQUENCE: 27

Asp Arg Val Tyr Ile His Pro Asn Ser Phe Arg Tyr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: synthetic peptide

<400> SEQUENCE: 28

Asp Arg Val Tyr Ile His Pro Lys Val Leu Arg Arg His
1               5                   10

<210> SEQ ID NO 29
<211> LENGTH: 22
<212> TYPE: PRT
<213> ORGANISM: Artificial Sequence
<220> FEATURE:
<223> OTHER INFORMATION: synthetic peptide

<400> SEQUENCE: 29

Asp Arg Val Tyr Ile His Pro Pro Ser Leu Arg Asp Pro Arg Pro Asn
1               5                   10                  15

Ala Pro Ser Thr Ser Ala
            20

<210> SEQ ID NO 30
<211> LENGTH: 15
<212> TYPE: PRT
<213> ORGANISM: Dendroaspis angusticeps

<400> SEQUENCE: 30

Pro Ser Leu Arg Asp Pro Arg Pro Asn Ala Pro Ser Thr Ser Ala
1               5                   10                  15

```
<210> SEQ ID NO 31
<211> LENGTH: 12
<212> TYPE: PRT
<213> ORGANISM: Artificial Sequence
<220> FEATURE:
<223> OTHER INFORMATION: synthetic peptide

<400> SEQUENCE: 31

Asn Ser Phe Arg Tyr Asp Arg Val Tyr Ile His Pro
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic peptide

<400> SEQUENCE: 32

Lys Val Leu Arg Arg His Asp Arg Val Tyr Ile His Pro
1               5                   10

<210> SEQ ID NO 33
<211> LENGTH: 22
<212> TYPE: PRT
<213> ORGANISM: Artificial Sequence
<220> FEATURE:
<223> OTHER INFORMATION: synthetic peptide

<400> SEQUENCE: 33

Pro Ser Leu Arg Asp Pro Arg Pro Asn Ala Pro Ser Thr Ser Ala Asp
1               5                   10                  15

Arg Val Tyr Ile His Pro
            20

<210> SEQ ID NO 34
<211> LENGTH: 24
<212> TYPE: PRT
<213> ORGANISM: Artificial Sequence
<220> FEATURE:
<223> OTHER INFORMATION: synthetic peptide

<400> SEQUENCE: 34

Asp Arg Val Tyr Ile His Pro Cys Phe Gly Leu Lys Leu Asp Arg Ile
1               5                   10                  15

Gly Ser Met Ser Gly Leu Gly Cys
            20

<210> SEQ ID NO 35
<211> LENGTH: 24
<212> TYPE: PRT
<213> ORGANISM: Artificial Sequence
<220> FEATURE:
<223> OTHER INFORMATION: synthetic peptide

<400> SEQUENCE: 35

Pro His Ile Tyr Val Arg Asp Cys Phe Gly Leu Lys Leu Asp Arg Ile
1               5                   10                  15

Gly Ser Met Ser Gly Leu Gly Cys
            20

<210> SEQ ID NO 36
<211> LENGTH: 17
<212> TYPE: PRT
<213> ORGANISM: Artificial Sequence
```

<220> FEATURE:
<223> OTHER INFORMATION: synthetic peptide

<400> SEQUENCE: 36

Cys Gly Leu Gly Ser Met Ser Gly Ile Arg Asp Leu Lys Leu Gly Phe
1               5                   10                  15

Cys

<210> SEQ ID NO 37
<211> LENGTH: 24
<212> TYPE: PRT
<213> ORGANISM: Artificial Sequence
<220> FEATURE:
<223> OTHER INFORMATION: synthetic peptide

<400> SEQUENCE: 37

Cys Phe Gly Leu Lys Leu Asp Arg Ile Gly Ser Met Ser Gly Leu Gly
1               5                   10                  15

Cys Pro His Ile Tyr Val Arg Asp
            20

<210> SEQ ID NO 38
<211> LENGTH: 24
<212> TYPE: PRT
<213> ORGANISM: Artificial Sequence
<220> FEATURE:
<223> OTHER INFORMATION: synthetic peptide

<400> SEQUENCE: 38

Cys Phe Gly Leu Lys Leu Asp Arg Ile Gly Ser Met Ser Gly Leu Gly
1               5                   10                  15

Cys Asp Arg Val Tyr Ile His Pro
            20

<210> SEQ ID NO 39
<211> LENGTH: 17
<212> TYPE: PRT
<213> ORGANISM: Artificial Sequence
<220> FEATURE:
<223> OTHER INFORMATION: synthetic peptide

<400> SEQUENCE: 39

Cys Gly Leu Gly Ser Gln Ala Gly Ile Arg Asp Met Arg Gly Gly Phe
1               5                   10                  15

Cys

<210> SEQ ID NO 40
<211> LENGTH: 17
<212> TYPE: PRT
<213> ORGANISM: Artificial Sequence
<220> FEATURE:
<223> OTHER INFORMATION: synthetic peptide

<400> SEQUENCE: 40

Cys Gly Leu Gly Ser Ser Ser Ser Ile Arg Asp Met Lys Arg Gly Phe
1               5                   10                  15

Cys

<210> SEQ ID NO 41
<211> LENGTH: 17
<212> TYPE: PRT
<213> ORGANISM: Artificial Sequence
<220> FEATURE:
<223> OTHER INFORMATION: synthetic peptide -continued

<400> SEQUENCE: 41

Cys Gly Leu Asn Ser Val His Asn Ile Arg Asp Ile Lys His Gly Phe
1               5                   10                  15

Cys

<210> SEQ ID NO 42
<211> LENGTH: 17
<212> TYPE: PRT
<213> ORGANISM: Artificial Sequence
<220> FEATURE:
<223> OTHER INFORMATION: synthetic peptide

<400> SEQUENCE: 42

Cys Gly Leu Gly Ser Gln Ala Gly Ile Arg Asp Met Arg Gly Gly Phe
1               5                   10                  15

Cys

<210> SEQ ID NO 43
<211> LENGTH: 30
<212> TYPE: PRT
<213> ORGANISM: Artificial Sequence
<220> FEATURE:
<223> OTHER INFORMATION: synthetic peptide

<400> SEQUENCE: 43

Ser Leu Arg Arg Ser Ser Cys Phe Gly Gly Arg Met Asp Arg Ile Gly
1               5                   10                  15

Ala Gln Ser Gly Leu Gly Cys Asp Arg Val Tyr Ile His Pro
            20                  25                  30

<210> SEQ ID NO 44
<211> LENGTH: 33
<212> TYPE: PRT
<213> ORGANISM: Artificial Sequence
<220> FEATURE:
<223> OTHER INFORMATION: synthetic peptide

<400> SEQUENCE: 44

Ser Pro Lys Met Val Gln Gly Ser Gly Cys Phe Gly Arg Lys Met Asp
1               5                   10                  15

Arg Ile Ser Ser Ser Ser Gly Leu Gly Cys Asp Arg Val Tyr Ile His
            20                  25                  30

Pro

<210> SEQ ID NO 45
<211> LENGTH: 29
<212> TYPE: PRT
<213> ORGANISM: Artificial Sequence
<220> FEATURE:
<223> OTHER INFORMATION: synthetic peptide

<400> SEQUENCE: 45

Gly Leu Ser Lys Gly Cys Phe Gly Leu Lys Leu Asp Arg Ile Gly Ser
1               5                   10                  15

Met Ser Gly Leu Gly Cys Asp Arg Val Tyr Ile His Pro
            20                  25

<210> SEQ ID NO 46
<211> LENGTH: 30
<212> TYPE: PRT
<213> ORGANISM: Artificial Sequence
<220> FEATURE:

<223> OTHER INFORMATION: synthetic peptide

<400> SEQUENCE: 46

Glu Val Lys Tyr Asp Pro Cys Phe Gly His Lys Ile Asp Arg Ile Asn
1               5                   10                  15

His Val Ser Asn Leu Gly Cys Asp Arg Val Tyr Ile His Pro
            20                  25                  30

<210> SEQ ID NO 47
<211> LENGTH: 34
<212> TYPE: PRT
<213> ORGANISM: Artificial Sequence
<220> FEATURE:
<223> OTHER INFORMATION: synthetic peptide

<400> SEQUENCE: 47

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asp Arg Val Tyr Ile
            20                  25                  30

His Pro

<210> SEQ ID NO 48
<211> LENGTH: 33
<212> TYPE: PRT
<213> ORGANISM: Artificial Sequence
<220> FEATURE:
<223> OTHER INFORMATION: synthetic peptide

<400> SEQUENCE: 48

Ser Pro Lys Met Val Gln Gly Ser Gly Cys Phe Gly Gly Arg Met Asp
1               5                   10                  15

Arg Ile Gly Ala Gln Ser Gly Leu Gly Cys Asp Arg Val Tyr Ile His
            20                  25                  30

Pro

<210> SEQ ID NO 49
<211> LENGTH: 29
<212> TYPE: PRT
<213> ORGANISM: Artificial Sequence
<220> FEATURE:
<223> OTHER INFORMATION: synthetic peptide

<400> SEQUENCE: 49

Gly Leu Ser Lys Gly Cys Phe Gly Gly Arg Met Asp Arg Ile Gly Ala
1               5                   10                  15

Gln Ser Gly Leu Gly Cys Asp Arg Val Tyr Ile His Pro
            20                  25

<210> SEQ ID NO 50
<211> LENGTH: 30
<212> TYPE: PRT
<213> ORGANISM: Artificial Sequence
<220> FEATURE:
<223> OTHER INFORMATION: synthetic peptide

<400> SEQUENCE: 50

Glu Val Lys Tyr Asp Pro Cys Phe Gly Gly Arg Met Asp Arg Ile Gly
1               5                   10                  15

Ala Gln Ser Gly Leu Gly Cys Asp Arg Val Tyr Ile His Pro
            20                  25                  30

```
<210> SEQ ID NO 51
<211> LENGTH: 34
<212> TYPE: PRT
<213> ORGANISM: Artificial Sequence
<220> FEATURE:
<223> OTHER INFORMATION: synthetic peptide

<400> SEQUENCE: 51

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asp Arg Val Tyr Ile
            20                  25                  30

His Pro

<210> SEQ ID NO 52
<211> LENGTH: 30
<212> TYPE: PRT
<213> ORGANISM: Artificial Sequence
<220> FEATURE:
<223> OTHER INFORMATION: synthetic peptide

<400> SEQUENCE: 52

Ser Leu Arg Arg Ser Ser Cys Phe Gly Arg Lys Met Asp Arg Ile Ser
1               5                   10                  15

Ser Ser Ser Gly Leu Gly Cys Asp Arg Val Tyr Ile His Pro
            20                  25                  30

<210> SEQ ID NO 53
<211> LENGTH: 29
<212> TYPE: PRT
<213> ORGANISM: Artificial Sequence
<220> FEATURE:
<223> OTHER INFORMATION: synthetic peptide

<400> SEQUENCE: 53

Gly Leu Ser Lys Gly Cys Phe Gly Arg Lys Met Asp Arg Ile Ser Ser
1               5                   10                  15

Ser Ser Gly Leu Gly Cys Asp Arg Val Tyr Ile His Pro
            20                  25

<210> SEQ ID NO 54
<211> LENGTH: 30
<212> TYPE: PRT
<213> ORGANISM: Artificial Sequence
<220> FEATURE:
<223> OTHER INFORMATION: synthetic peptide

<400> SEQUENCE: 54

Glu Val Lys Tyr Asp Pro Cys Phe Gly Arg Lys Met Asp Arg Ile Ser
1               5                   10                  15

Ser Ser Ser Gly Leu Gly Cys Asp Arg Val Tyr Ile His Pro
            20                  25                  30

<210> SEQ ID NO 55
<211> LENGTH: 34
<212> TYPE: PRT
<213> ORGANISM: Artificial Sequence
<220> FEATURE:
<223> OTHER INFORMATION: synthetic peptide

<400> SEQUENCE: 55

Thr Ala Pro Arg Ser Leu Arg Arg Ser Ser Cys Phe Gly Arg Lys Met
1               5                   10                  15

Asp Arg Ile Ser Ser Ser Ser Gly Leu Gly Cys Asp Arg Val Tyr Ile
```

His Pro

```
<210> SEQ ID NO 56
<211> LENGTH: 30
<212> TYPE: PRT
<213> ORGANISM: Artificial Sequence
<220> FEATURE:
<223> OTHER INFORMATION: synthetic peptide

<400> SEQUENCE: 56
```

Ser Leu Arg Arg Ser Ser Cys Phe Gly Leu Lys Leu Asp Arg Ile Gly
1               5                   10                  15

Ser Met Ser Gly Leu Gly Cys Asp Arg Val Tyr Ile His Pro
            20                  25                  30

```
<210> SEQ ID NO 57
<211> LENGTH: 33
<212> TYPE: PRT
<213> ORGANISM: Artificial Sequence
<220> FEATURE:
<223> OTHER INFORMATION: synthetic peptide

<400> SEQUENCE: 57
```

Ser Pro Lys Met Val Gln Gly Ser Gly Cys Phe Gly Leu Lys Leu Asp
1               5                   10                  15

Arg Ile Gly Ser Met Ser Gly Leu Gly Cys Asp Arg Val Tyr Ile His
            20                  25                  30

Pro

```
<210> SEQ ID NO 58
<211> LENGTH: 30
<212> TYPE: PRT
<213> ORGANISM: Artificial Sequence
<220> FEATURE:
<223> OTHER INFORMATION: synthetic peptide

<400> SEQUENCE: 58
```

Glu Val Lys Tyr Asp Pro Cys Phe Gly Leu Lys Leu Asp Arg Ile Gly
1               5                   10                  15

Ser Met Ser Gly Leu Gly Cys Asp Arg Val Tyr Ile His Pro
            20                  25                  30

```
<210> SEQ ID NO 59
<211> LENGTH: 33
<212> TYPE: PRT
<213> ORGANISM: Artificial Sequence
<220> FEATURE:
<223> OTHER INFORMATION: synthetic peptide

<400> SEQUENCE: 59
```

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asp Arg Val Tyr Ile
            20                  25                  30

Pro

```
<210> SEQ ID NO 60
<211> LENGTH: 29
<212> TYPE: PRT
<213> ORGANISM: Artificial Sequence
<220> FEATURE:
<223> OTHER INFORMATION: synthetic peptide
```

```
<400> SEQUENCE: 60

Asp Arg Val Tyr Ile His Pro Cys Phe Gly Gly Arg Met Asp Arg Ile
1               5                   10                  15

Gly Ala Gln Ser Gly Leu Gly Cys Asn Ser Phe Arg Tyr
            20                  25

<210> SEQ ID NO 61
<211> LENGTH: 30
<212> TYPE: PRT
<213> ORGANISM: Artificial Sequence
<220> FEATURE:
<223> OTHER INFORMATION: synthetic peptide

<400> SEQUENCE: 61

Asp Arg Val Tyr Ile His Pro Cys Phe Gly Arg Lys Met Asp Arg Ile
1               5                   10                  15

Ser Ser Ser Ser Gly Leu Gly Cys Lys Tyr Leu Arg Arg His
            20                  25                  30
```

NATRIURETIC POLYPEPTIDES

CROSS-REFERENCE TO RELATED APPLICATIONS

This application is a continuation of U.S. application Ser. No. 15/232,429, filed Aug. 9, 2016 (now U.S. Pat. No. 9,587,004), which is a continuation of U.S. application Ser. No. 14/791,047, filed Jul. 2, 2015 (now U.S. Pat. No. 9,441,027), which is a continuation of U.S. application Ser. No. 14/003,481, filed Sep. 6, 2013 (now U.S. Pat. No. 9,102,707), which is a National Stage application under 35 U.S.C. § 371 of International Application No. PCT/US2012/051734, filed Aug. 21, 2012, which claims the benefit of U.S. Provisional Application Ser. No. 61/648,718, filed May 18, 2012 and U.S. Provisional Application Ser. No. 61/529,113, filed Aug. 30, 2011. The disclosures of the prior applications are considered part of (and are incorporated by reference in) the disclosure of this application.

STATEMENT AS TO FEDERALLY SPONSORED RESEARCH

This invention was made with government support under HL036634 and HL076611, awarded by National Institutes of Health. The government has certain rights in the invention.

BACKGROUND

1. Technical Field

This document relates to natriuretic polypeptides. For example, this document provides methods and materials related to natriuretic polypeptides and the use of natriuretic polypeptides to treat cardiovascular and renal conditions.

2. Background Information

Natriuretic polypeptides are polypeptides that can cause natriuresis (increased sodium excretion in the urine). Such polypeptides can be produced by brain, heart, kidney, and/or vascular tissue. The natriuretic peptide family in humans includes the cardiac hormones atrial natriuretic peptide (ANP), B-type natriuretic peptide (BNP), C-type natriuretic peptide (CNP), and urodilatin (URO). Natriuretic polypeptides function via guanylyl cyclase receptors (i.e., NPR-A for ANP, BNP, and URO; and NPR-B for CNP) and the second messenger cyclic 3'5' guanosine monophosphate (cGMP) (Kuhn, *Circ. Res.*, 93:700-709 (2003); Tawaragi et al., *Biochem. Biophys. Res. Commun.*, 175:645-651 (1991); and Komatsu et al., *Endocrinol.*, 129:1104-1106 (1991)).

SUMMARY

This document provides methods and materials related to natriuretic polypeptides and the use of natriuretic polypeptides to treat cardiovascular and/or renal conditions. For example, this document provides chimeric polypeptides having at least one amino acid segment (e.g., N-terminus tail, ring structure, C-terminus tail, or a combination thereof) of a natriuretic peptide (e.g., ANP, BNP, CNP, URO, or Dendroaspis natriuretic peptide (DNP)) and an amino acid segment of an angiotensin polypeptide (e.g., Ang-(1-7)).

As described herein, a chimeric polypeptide can be designed to include the Ang-(1-7) amino acid sequence attached as the C terminus of the ring structure of CNP in a manner that results in a chimeric polypeptide having the ability to stimulate human cardiac fibroblasts to produce cGMP. These results demonstrate that chimeric polypeptides can be designed to include an amino acid segment of an angiotensin polypeptide (e.g., Ang-(1-7)) and at least one amino acid segment (e.g., N-terminus tail, C-terminus tail, or a combination thereof) of a natriuretic peptide (e.g., ANP, BNP, CNP, URO, or Dendroaspis natriuretic peptide (DNP)) in a manner that allows the chimeric polypeptide to exhibit an activity such as the ability to activate cGMP production. In some cases, a chimeric polypeptide provided herein can exhibit a diuretic activity, a natriuretic activity, the ability to activate cGMP, the ability to increase glomerular filtration rate, the ability to reduce renin production, the ability to reduce angiotensin production, the ability to reduce aldosterone production, the ability to reduce abnormally elevated cardiac filling pressures, the ability to optimize renal blood flow, or a combination thereof. In some cases, a chimeric polypeptide provided herein can be a chimeric natriuretic polypeptide.

In general, one aspect of this document features a polypeptide from 17 to 50 amino acid residues in length. The polypeptide comprises, or consists essentially of, in an order from amino terminus to carboxy terminus, (a) the sequence set forth in SEQ ID NO:2 or the sequence set forth in SEQ ID NO:2 with no more than three additions, subtractions, or substitutions, (b) the sequence set forth in SEQ ID NO:3 or the sequence set forth in SEQ ID NO:3 with no more than five additions, subtractions, or substitutions, and (c) the sequence set forth in SEQ ID NO:1 or the sequence set forth in SEQ ID NO:1 with no more than two additions, subtractions, or substitutions. The polypeptide can have a cGMP-activating property. The polypeptide can comprise the sequence set forth in SEQ ID NO:2. The polypeptide can comprise the sequence set forth in SEQ ID NO:3. The polypeptide can comprise the sequence set forth in SEQ ID NO:1.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:4 or the sequence set forth in SEQ ID NO:4 with no more than three additions, subtractions, or substitutions, (b) the sequence set forth in SEQ ID NO:5 or the sequence set forth in SEQ ID NO:5 with no more than five additions, subtractions, or substitutions, and (c) the sequence set forth in SEQ ID NO:1 or the sequence set forth in SEQ ID NO:1 with no more than two additions, subtractions, or substitutions. The polypeptide can have a cGMP-activating property. The polypeptide can comprise the sequence set forth in SEQ ID NO:4. The polypeptide can comprise the sequence set forth in SEQ ID NO:5. The polypeptide can comprise the sequence set forth in SEQ ID NO:1.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:6 or the sequence set forth in SEQ ID NO:6 with no more than three additions, subtractions, or substitutions, (b) the sequence set forth in SEQ ID NO:7 or the sequence set forth in SEQ ID NO:7 with no more than five additions, subtractions, or substitutions, and (c) the sequence set forth in SEQ ID NO:1 or the sequence set forth in SEQ ID NO:1 with no more than two additions, subtractions, or substitutions. The polypeptide can have a cGMP-activating property. The polypeptide can comprise the sequence set forth in SEQ ID NO:6. The polypeptide can comprise the sequence set forth in SEQ ID NO:7. The polypeptide can comprise the sequence set forth in SEQ ID NO:1.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:8 or the sequence set forth in SEQ ID NO:8 with no more than three additions, subtractions, or substitutions, (b) the sequence set forth in SEQ ID NO:9 or the sequence set forth in SEQ ID NO:9 with no more than five additions, subtractions, or substitutions, and (c) the sequence set forth in SEQ ID NO:1 or the sequence set forth in SEQ ID NO:1 with no more than two additions, subtractions, or substitutions. The polypeptide can have a cGMP-activating property. The polypeptide can comprise the sequence set forth in SEQ ID NO:8. The polypeptide can comprise the sequence set forth in SEQ ID NO:9. The polypeptide can comprise the sequence set forth in SEQ ID NO:1.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:10 or the sequence set forth in SEQ ID NO:10 with no more than three additions, subtractions, or substitutions, (b) the sequence set forth in SEQ ID NO:11 or the sequence set forth in SEQ ID NO:11 with no more than five additions, subtractions, or substitutions, and (c) the sequence set forth in SEQ ID NO:1 or the sequence set forth in SEQ ID NO:1 with no more than two additions, subtractions, or substitutions. The polypeptide can have a cGMP-activating property. The polypeptide can comprise the sequence set forth in SEQ ID NO:10. The polypeptide can comprise the sequence set forth in SEQ ID NO:11. The polypeptide can comprise the sequence set forth in SEQ ID NO:1.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:1 or the sequence set forth in SEQ ID NO:1 with no more than two additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:12 or the sequence set forth in SEQ ID NO:12 with no more than two additions, subtractions, or substitutions. The polypeptide can have a cGMP-activating property. The polypeptide can comprise the sequence set forth in SEQ ID NO:1. The polypeptide can comprise the sequence set forth in SEQ ID NO:2. The polypeptide can comprise the sequence set forth in SEQ ID NO:12.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:1 or the sequence set forth in SEQ ID NO:1 with no more than two additions, subtractions, or substitutions, (b) the sequence set forth in SEQ ID NO:5 or the sequence set forth in SEQ ID NO:5 with no more than five additions, subtractions, or substitutions, and (c) the sequence set forth in SEQ ID NO:13 or the sequence set forth in SEQ ID NO:13 with no more than two additions, subtractions, or substitutions. The polypeptide can have a cGMP-activating property. The polypeptide can comprise the sequence set forth in SEQ ID NO:1. The polypeptide can comprise the sequence set forth in SEQ ID NO:5. The polypeptide can comprise the sequence set forth in SEQ ID NO:13.

In another aspect, this document features a polypeptide from 10 to 14 amino acid residues in length. The polypeptide comprises, or consists essentially of, in an order from amino terminus to carboxy terminus, (a) the sequence set forth in SEQ ID NO:1 or the sequence set forth in SEQ ID NO:1 with no more than two additions, subtractions, or substitutions, and (b) the sequence set forth in SEQ ID NO:12 or the sequence set forth in SEQ ID NO:12 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:12. The polypeptide can lack a ring structure.

In another aspect, this document features a polypeptide from 10 to 16 amino acid residues in length. The polypeptide comprises, or consists essentially of, in an order from amino terminus to carboxy terminus, (a) the sequence set forth in SEQ ID NO:1 or the sequence set forth in SEQ ID NO:1 with no more than two additions, subtractions, or substitutions, and (b) the sequence set forth in SEQ ID NO:13 or the sequence set forth in SEQ ID NO:13 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:13. The polypeptide can lack a ring structure.

In another aspect, this document features a polypeptide from 19 to 25 amino acid residues in length. The polypeptide comprises, or consists essentially of, in an order from amino terminus to carboxy terminus, (a) the sequence set forth in SEQ ID NO:1 or the sequence set forth in SEQ ID NO:1 with no more than two additions, subtractions, or substitutions, and (b) the sequence set forth in SEQ ID NO:30 or the sequence set forth in SEQ ID NO:30 with no more than five additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:30. The polypeptide can lack a ring structure.

In another aspect, this document features a polypeptide from 10 to 14 amino acid residues in length. The polypeptide comprises, or consists essentially of, in an order from amino terminus to carboxy terminus, (a) the sequence set forth in SEQ ID NO:12 or the sequence set forth in SEQ ID NO:12 with no more than two additions, subtractions, or substitutions, and (b) the sequence set forth in SEQ ID NO:1 or the sequence set forth in SEQ ID NO:1 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:12. The polypeptide can lack a ring structure.

In another aspect, this document features a polypeptide from 10 to 16 amino acid residues in length. The polypeptide comprises, or consists essentially of, in an order from amino terminus to carboxy terminus, (a) the sequence set forth in SEQ ID NO:13 or the sequence set forth in SEQ ID NO:13 with no more than two additions, subtractions, or substitutions, and (b) the sequence set forth in SEQ ID NO:1 or the sequence set forth in SEQ ID NO:1 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:13. The polypeptide can lack a ring structure.

In another aspect, this document features a polypeptide from 19 to 25 amino acid residues in length. The polypeptide comprises, or consists essentially of, in an order from amino terminus to carboxy terminus, (a) the sequence set forth in SEQ ID NO:30 or the sequence set forth in SEQ ID NO:30 with no more than five additions, subtractions, or substitutions, and (b) the sequence set forth in SEQ ID NO:1 or the sequence set forth in SEQ ID NO:1 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:30. The polypeptide can lack a ring structure.

In another aspect, this document features a polypeptide from 20 to 28 amino acid residues in length. The polypeptide comprises, in an order from amino terminus to carboxy terminus (a) the sequence set forth in SEQ ID NO:1 or the sequence set forth in SEQ ID NO:1 with no more than two additions, subtractions, or substitutions, and (b) the sequence set forth in SEQ ID NO:7 or the sequence set forth in SEQ ID NO:7 with no more than five additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:7. The polypeptide can lack a C-terminal tail attached to a ring structure.

In another aspect, this document features a polypeptide from 20 to 28 amino acid residues in length. The polypeptide comprises, or consists essentially of, in an order from amino terminus to carboxy terminus, (a) the sequence set forth in SEQ ID NO:36 or the sequence set forth in SEQ ID NO:36 with no more than five additions, subtractions, or substitutions, and (b) the sequence set forth in SEQ ID NO:1 or the sequence set forth in SEQ ID NO:1 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:36. The polypeptide can lack a N-terminal tail attached to a ring structure.

In another aspect, this document features a polypeptide from 20 to 28 amino acid residues in length. The polypeptide comprises, or consists essentially of, in an order from amino terminus to carboxy terminus, (a) the sequence set forth in SEQ ID NO:1 or the sequence set forth in SEQ ID NO:1 with no more than two additions, subtractions, or substitutions, and (b) the sequence set forth in SEQ ID NO:36 or the sequence set forth in SEQ ID NO:36 with no more than five additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:36. The polypeptide can lack a C-terminal tail attached to a ring structure.

In another aspect, this document features a polypeptide from 20 to 28 amino acid residues in length. The polypeptide comprises, or consists essentially of, in an order from amino terminus to carboxy terminus, (a) the sequence set forth in SEQ ID NO:7 or the sequence set forth in SEQ ID NO:7 with no more than five additions, subtractions, or substitutions, and (b) the sequence set forth in SEQ ID NO:1 or the sequence set forth in SEQ ID NO:1 with no more than two additions, subtractions, or substitutions. The polypeptide can comprise a cGMP-activating property. The polypeptide can comprise the sequence set forth in SEQ ID NO:1. The polypeptide can comprise the sequence set forth in SEQ ID NO:7. The polypeptide can lack a N-terminal tail attached to a ring structure.

In another aspect, this document features a polypeptide from 17 to 50 amino acid residues in length. The polypeptide comprises, or consists essentially of, in an order from amino terminus to carboxy terminus, (a) the sequence set forth in SEQ ID NO:2, the sequence set forth in SEQ ID NO:4, the sequence set forth in SEQ ID NO:6, the sequence set forth in SEQ ID NO:8, the sequence set forth in SEQ ID NO:10, the sequence set forth in SEQ ID NO:2 with no more than three additions, subtractions, or substitutions, the sequence set forth in SEQ ID NO:4 with no more than three additions, subtractions, or substitutions, the sequence set forth in SEQ ID NO:6 with no more than three additions, subtractions, or substitutions, the sequence set forth in SEQ ID NO:8 with no more than three additions, subtractions, or substitutions, or the sequence set forth in SEQ ID NO:10 with no more than three additions, subtractions, or substitutions, (b) the sequence set forth in SEQ ID NO:3, the sequence set forth in SEQ ID NO:5, the sequence set forth in SEQ ID NO:7, the sequence set forth in SEQ ID NO:9, the sequence set forth in SEQ ID NO:11, the sequence set forth in SEQ ID NO:3 with no more than five additions, subtractions, or substitutions, the sequence set forth in SEQ ID NO:5 with no more than five additions, subtractions, or substitutions, the sequence set forth in SEQ ID NO:7 with no more than five additions, subtractions, or substitutions, the sequence set forth in SEQ ID NO:9 with no more than five additions, subtractions, or substitutions, or the sequence set forth in SEQ ID NO:11 with no more than five additions, subtractions, or substitutions, and (c) the sequence set forth in SEQ ID NO:1 or the sequence set forth in SEQ ID NO:1 with no more than two additions, subtractions, or substitutions. The polypeptide can comprise a cGMP-activating property. The polypeptide can comprise the sequence set forth in SEQ ID NO:2, 4, 6, 8, or 10. The polypeptide can comprise the sequence set forth in SEQ ID NO:3, 5, 7, 9, or 11. The polypeptide can comprise the sequence set forth in SEQ ID NO:1. The polypeptide can comprise the sequence set forth in SEQ ID NO:43, 44, 45, 46, 47, 48, 49, 50, 51, 52, 53, 54, 55, 56, 57, 58, or 59 with no more than five additions, subtractions, or substitutions. The polypeptide can be from 17 to 45 amino acid residues, from 17 to 40 amino acid residues, from 17 to 35 amino acid residues, from 20 to 50 amino acid residues, from 25 to 50 amino acid residues, from 20 to 45 amino acid residues, from 20 to 40 amino acid residues, from 20 to 35 amino acid residues, from 25 to 45 amino acid residues, from 25 to 40 amino acid residues, or from 25 to 35 amino acid residues, in length.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 33A), Ang1-7BNP (FIG. 33B), or BNP-Ang1-7 (FIG. 33C). The HEK 293 cells were stably transfected to express NPR-A (i.e., GC-A).

FIG. 34A), Ang1-7BNP (FIG. 34B), or BNP-Ang1-7 (FIG. 34C). The HEK 293 cells were stably transfected to express NPR-B (i.e., GC-B).

DETAILED DESCRIPTION

Figure 1:
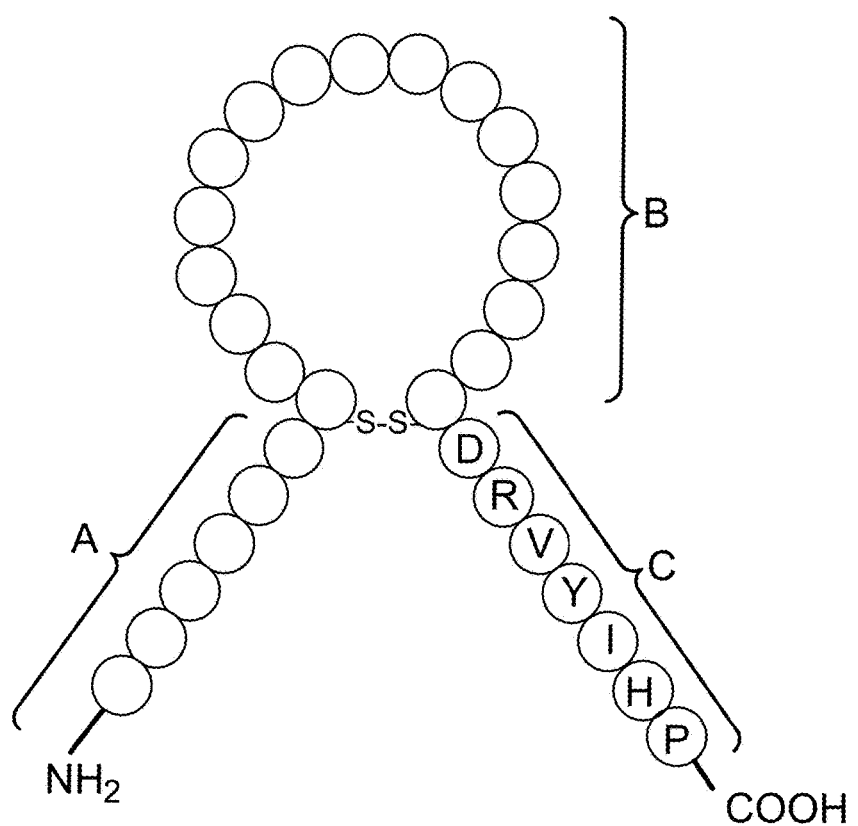
FIG. 1 is a structural schematic of a chimeric polypeptide containing an N-terminus and ring structure of a natriuretic peptide and a C-terminus of a segment of an angiotensin polypeptide in accordance with some embodiments. The amino acid segment of an angiotensin polypeptide shown in FIG. 1 (DRVYIHP; SEQ ID NO:1) can be referred to as angiotensin-(1-7) or Ang-(1-7). The N-terminus and ring structure can have the sequence of any appropriate natriuretic peptide including, without limitation, ANP, BNP, CNP, DNP, and URO. "A" refers to an amino acid sequence from the N-terminus of a natriuretic peptide, "B" refers to an amino acid sequence from the ring structure of a natriuretic peptide, and "C" refers to an amino acid sequence of Ang(1-7), which can form the C-terminus of a chimeric polypeptide.
Figure 2:
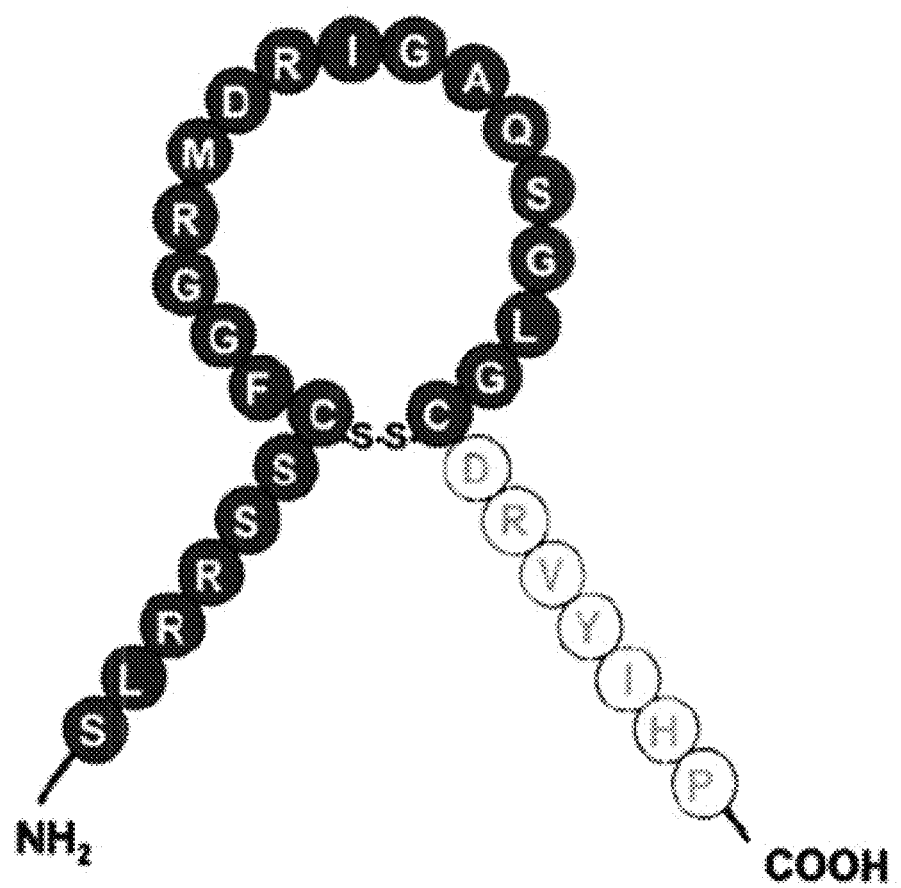
FIG. 2 is a structural schematic of a chimeric polypeptide (SEQ ID NO:43) containing an N-terminus and ring structure of ANP and a C-terminal Ang-(1-7) in accordance with some embodiments. The amino acid sequence of the N-terminal segment of ANP shown in FIG. 2 (SLRRSS; SEQ ID NO:2) can be referred to as $ANP_{N-term}$, while the amino acid sequence of the ring structure segment of ANP shown in FIG. 2 (CFGGRMDRIGAQ-SGLGC; SEQ ID NO:3) can be referred to as $ANP_{ring}$.

This document provides methods and materials related to natriuretic polypeptides and the use of natriuretic polypeptides to treat cardiovascular and/or renal conditions. For example, this document provides chimeric polypeptides having at least one amino acid segment (e.g., N-terminus tail, ring structure, reverse ring structure, C-terminus tail, or a combination thereof) of a natriuretic peptide (e.g., ANP, BNP, CNP, URO, or DNP) and an amino acid segment of an angiotensin polypeptide (e.g., Ang-(1-7), Ang-(1-8), or Ang-(1-9)). In some cases, a chimeric polypeptide provided herein can be used to increase natriuretic activity in a subject in need thereof. In some cases, a chimeric polypeptide provided herein can be used to increase plasma cGMP levels, urinary cGMP excretion, net renal cGMP generation, urine flow, urinary sodium excretion, urinary potassium excretion, hematocrit, plasma BNP immunoreactivity, renal blood flow, and/or plasma ANP immunoreactivity. In some cases, a chimeric polypeptide provided herein can be used to decrease renal vascular resistance, proximal and distal fractional reabsorption of sodium, mean arterial pressure, pulmonary capillary wedge pressure, right atrial pressure, pulmonary arterial pressure, plasma renin activity, plasma angiotensin II levels, plasma aldosterone levels, renal perfusion pressure, and/or systemic vascular resistance. In some cases, a chimeric polypeptide provided herein can be used to treat, inhibit, and/or prevent cardiac remodeling and ischemia-reperfusion injury, particularly after acute myocardial infarction (AMI) and/or acute heart failure (AHF).

For example, a chimeric polypeptide provided herein can be used to increase plasma cGMP, which may be desirable for applications in attenuating myocardial ischemia-reperfusion injury (Padilla et al., *Cardiovasc. Res.*, 51:592-600 (2001)).

As described herein, a chimeric polypeptide can be designed to include at least one amino acid segment (e.g., N-terminus tail, ring structure, reverse ring structure, C-terminus tail, or a combination thereof) of a natriuretic peptide and an amino acid segment of an angiotensin polypeptide. Examples of natriuretic peptides or "NPs" include, without limitation, ANP, BNP, CNP, URO, and DNP. A chimeric polypeptide provided herein can include any appropriate amino acid segment of an angiotensin polypeptide (e.g., human angiotensin polypeptide). For example, a chimeric polypeptide provided herein can include the sequence set forth in SEQ ID NO:1. In some cases, a chimeric polypeptide provided herein can include a full length angiotensin polypeptide (e.g., a full length human angiotensin polypeptide). For example, a chimeric polypeptide provided herein can include the following sequence: DRVYIHPFHL (SEQ ID NO:14).

A chimeric polypeptide provided herein can include a ring structure of a natriuretic peptide. Examples of ring structures include, without limitation, $ANP_{ring}$, $BNP_{ring}$, $CNP_{ring}$, $DNP_{ring}$, and $URO_{ring}$. In some cases, an $ANP_{ring}$, $BNP_{ring}$, $CNP_{ring}$, $DNP_{ring}$, or $URO_{ring}$ having one or more (e.g., one, two, three, four, five, six, or more) amino acid additions, subtractions, or substitutions can be used. For example, an $ANP_{ring}$ or $BNP_{ring}$ having two amino acid substitutions can be used as a ring structure of a chimeric polypeptide provided herein.

In some cases, a chimeric polypeptide provided herein includes a reverse ring structure of a natriuretic peptide. Examples of reverse ring structures include, without limitation, reverse-$ANP_{ring}$ (CGLGSQAGIRDMRGGFC; SEQ ID NO:39), reverse-$BNP_{ring}$ (CGLGSSSSIRDMKRGFC; SEQ ID NO:40), reverse-$CNP_{ring}$, reverse-$DNP_{ring}$ (CGLNSVHNIRDIKHGFC; SEQ ID NO:41), and reverse-$URO_{ring}$ (CGLGSQAGIRDMRGGFC; SEQ ID NO:42). In some cases, a reverse-$ANP_{ring}$, reverse-$BNP_{ring}$, reverse-$CNP_{ring}$, reverse-$DNP_{ring}$, or reverse-$URO_{ring}$ having one or more (e.g., one, two, three, four, five, six, or more) amino acid additions, subtractions, or substitutions can be used. For example, a reverse-$ANP_{ring}$ or reverse-$BNP_{ring}$ having two amino acid substitutions can be used as a ring structure of a chimeric polypeptide provided herein.

In some cases, a chimeric polypeptide provided herein can include any appropriate amino acid segment of an angiotensin polypeptide either as an N-terminal portion or as a C-terminal portion with respect to a ring structure or reverse ring structure for those polypeptides containing such a ring structure or reverse ring structure. For example, a chimeric polypeptide provided herein can include an amino acid segment of an angiotensin polypeptide (e.g., Ang-(1-7)) followed by a ring structure and optionally a C-terminus of a natriuretic peptide (e.g., $ANP_{C-term}$, $BNP_{C-term}$, or $DNP_{C-term}$). In some cases, an optional N-terminus of a natriuretic peptide (e.g., $ANP_{N-term}$ or $BNP_{N-term}$) can be followed by a ring structure of a natriuretic peptide and an amino acid segment of an angiotensin polypeptide (e.g., Ang-(1-7)).

In some cases, a chimeric polypeptide provided herein can include any appropriate amino acid segment of an angiotensin polypeptide either as an N-terminal portion or as a C-terminal portion attached to an N-terminus (e.g., $ANP_{N-term}$, $BNP_{N-term}$, $CNP_{N-term}$, $DNP_{N-term}$, or $URO_{N-term}$) or C-terminus of a natriuretic peptide (e.g., $ANP_{C-term}$, $BNP_{C-term}$, or $DNP_{C-term}$) without a ring or reverse ring structure. For example, a chimeric polypeptide provided herein can include an amino acid segment of an angiotensin polypeptide (e.g., Ang-(1-7)) followed by a C-terminus of a natriuretic peptide (e.g., $ANP_{C-term}$ or $BNP_{C-term}$) without a ring or reverse ring structure. In some cases, a C-terminus of a natriuretic peptide (e.g., $ANP_{C-term}$ or $BNP_{C-term}$) can be followed by an amino acid segment of an angiotensin polypeptide (e.g., Ang-(1-7)) without a ring or reverse ring structure.

Figure 3:
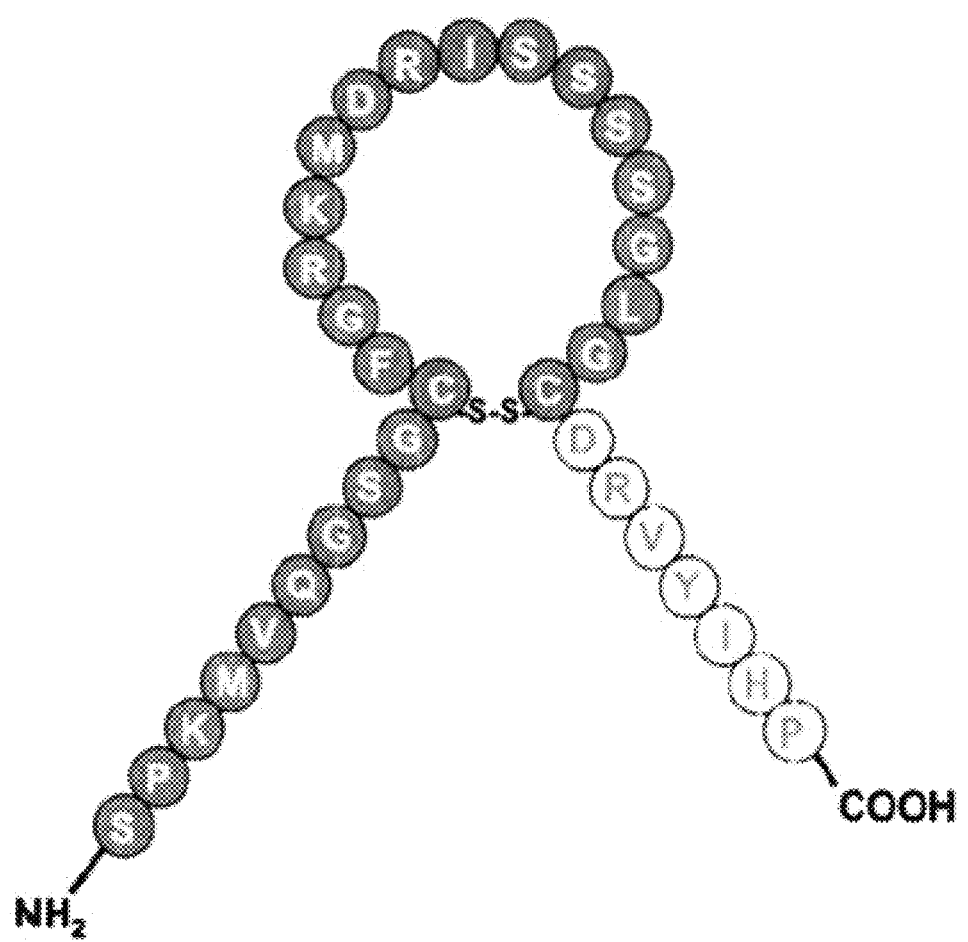
FIG. 3 is a structural schematic of a chimeric polypeptide (SEQ ID NO:44) containing an N-terminus and ring structure of BNP and a C-terminal Ang-(1-7) in accordance with some embodiments. The amino acid sequence of the N-terminal segment of BNP shown in FIG. 3 (SPKMVQGSG; SEQ ID NO:4) can be referred to as $BNP_{N-term}$, while the amino acid sequence of the ring structure segment of BNP shown in FIG. 3 (CFGRKM-DRISSSSGLGC; SEQ ID NO:5) can be referred to as $BNP_{ring}$. The chimeric polypeptide having the amino acid sequence set forth in SEQ ID NO:44 can be referred to as BNP-Ang1-7.
Figure 11:
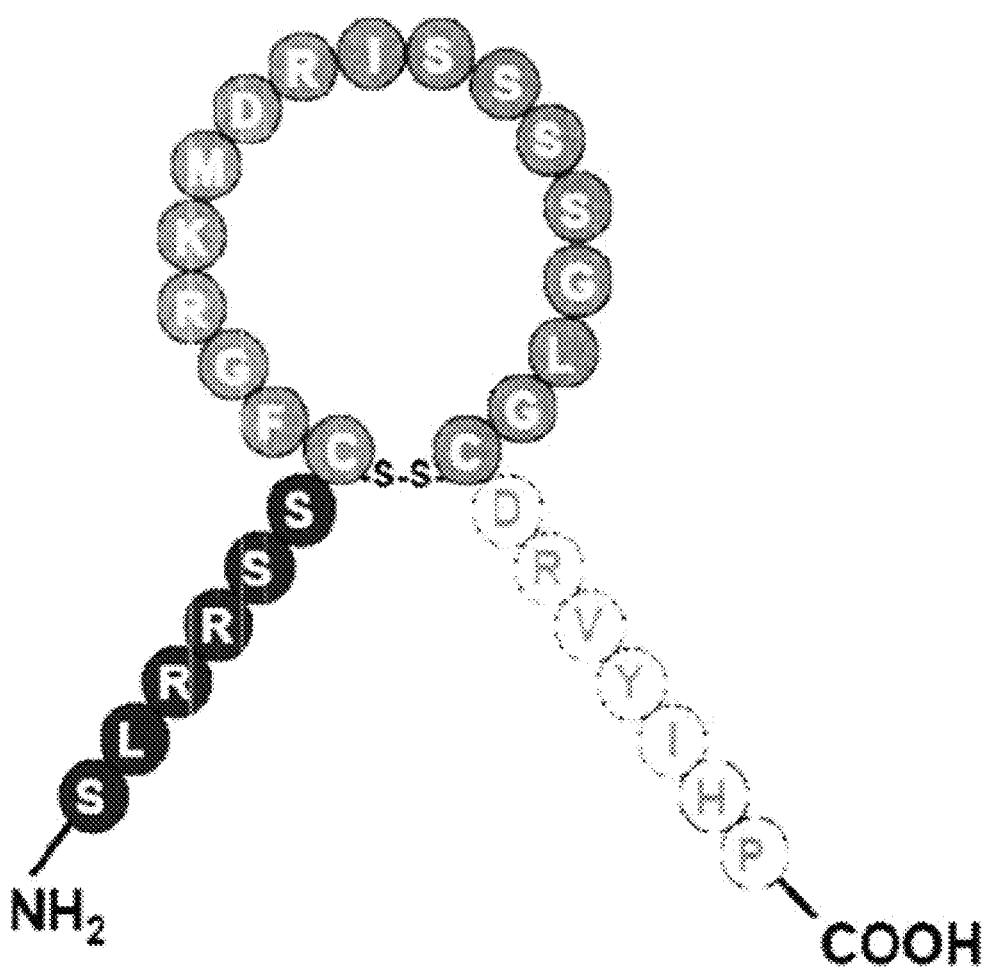
FIG. 11 is a structural schematic of a chimeric polypeptide (SEQ ID NO:52) containing an N-terminus of ANP ($ANP_{N-term}$), a ring structure of BNP ($BNP_{ring}$), and a C-terminal Ang-(1-7) in accordance with some embodiments.
Figure 12:
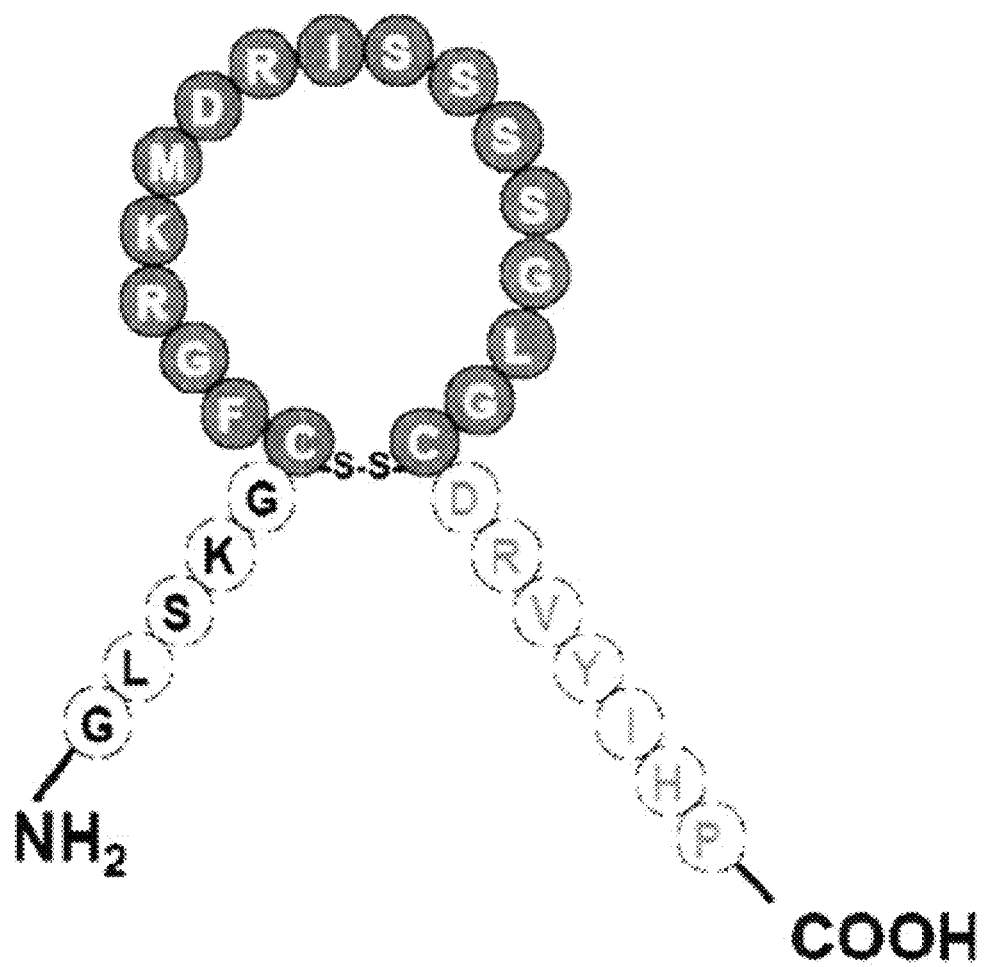
FIG. 12 is a structural schematic of a chimeric polypeptide (SEQ ID NO:53) containing an N-terminus of CNP ($CNP_{N-term}$), a ring structure of BNP ($BNP_{ring}$), and a C-terminal Ang-(1-7) in accordance with some embodiments.
Figure 13:
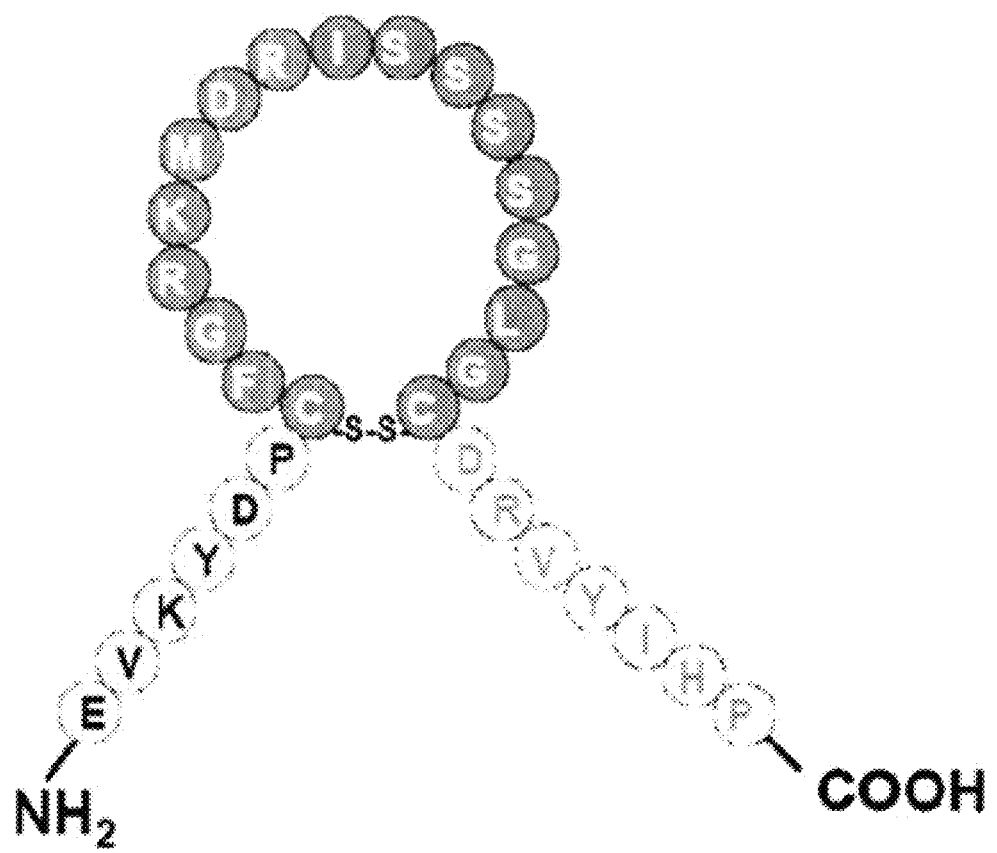
FIG. 13 is a structural schematic of a chimeric polypeptide (SEQ ID NO:54) containing an N-terminus of DNP ($DNP_{N-term}$), a ring structure of BNP ($BNP_{ring}$), and a C-terminal Ang-(1-7) in accordance with some embodiments.
Figure 14:
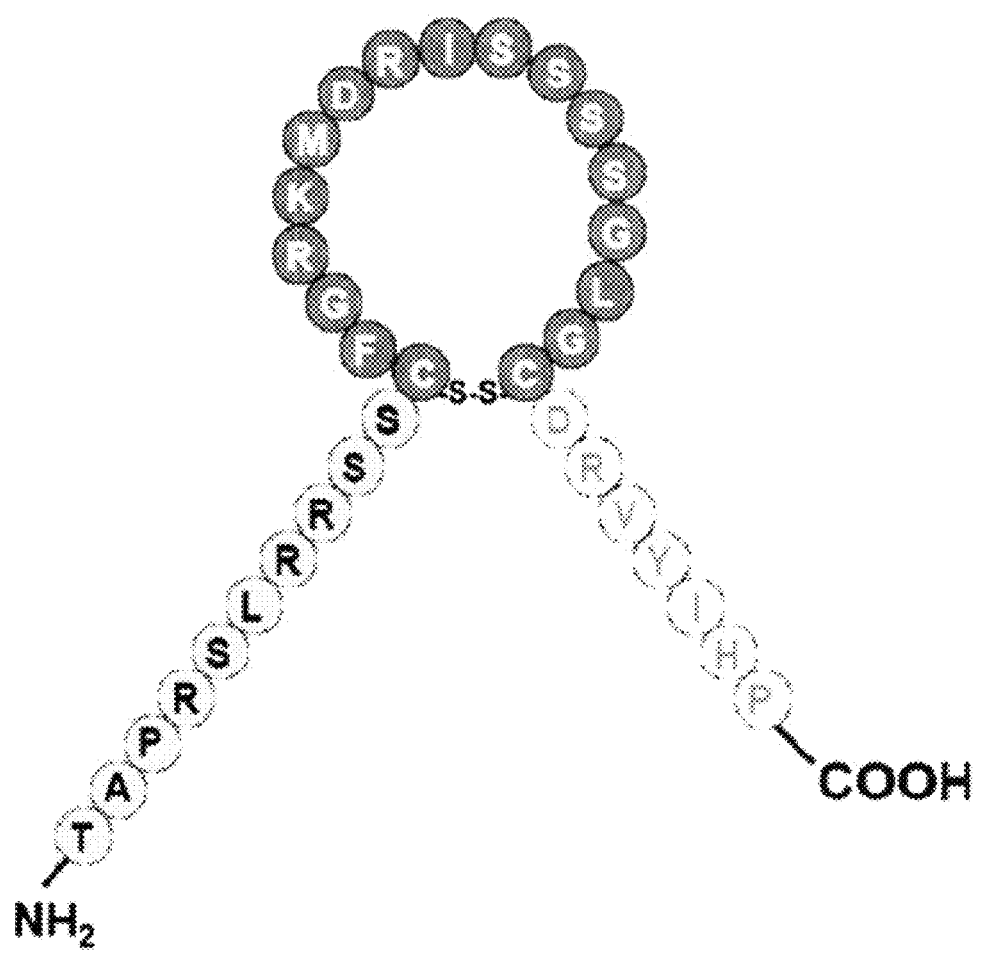
FIG. 14 is a structural schematic of a chimeric polypeptide (SEQ ID NO:55) containing an N-terminus of URO ($URO_{N-term}$), a ring structure of BNP ($BNP_{ring}$), and a C-terminal Ang-(1-7) in accordance with some embodiments.
Figure 15:
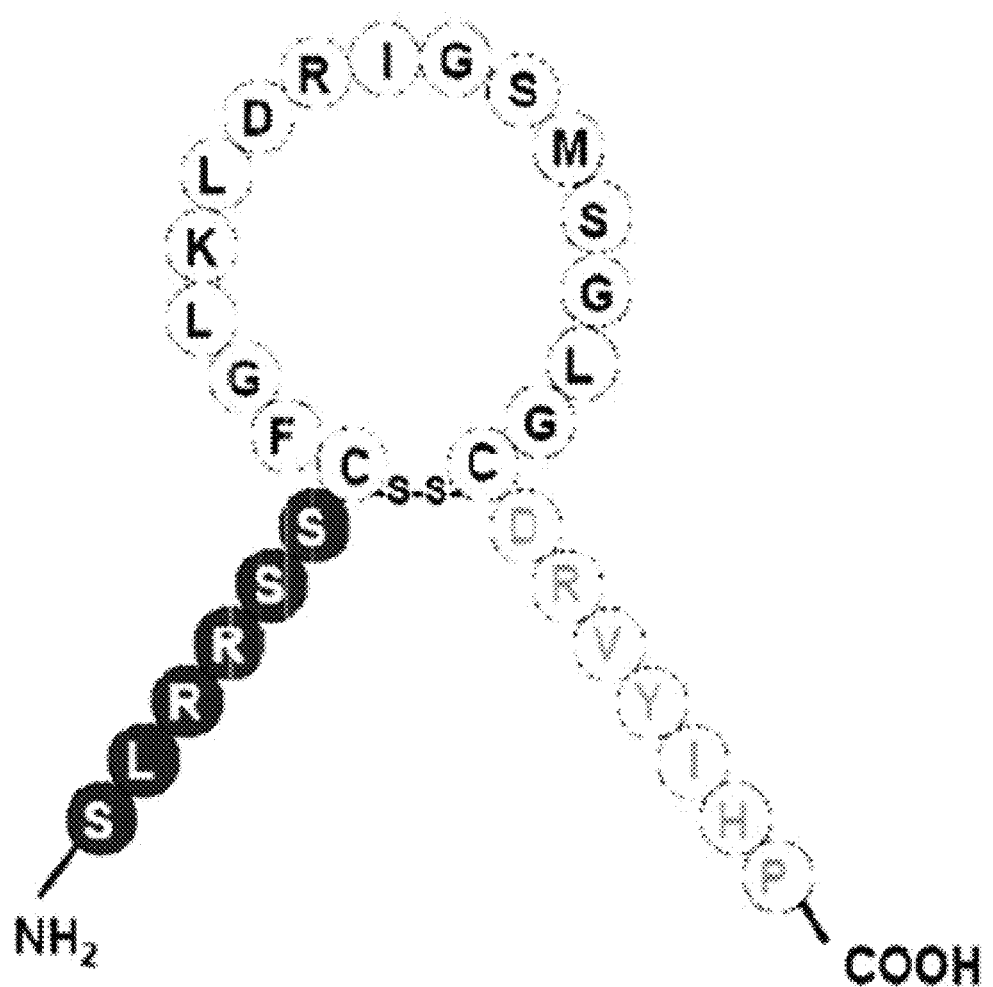
FIG. 15 is a structural schematic of a chimeric polypeptide (SEQ ID NO:56) containing an N-terminus of ANP ($ANP_{N-term}$), a ring structure of CNP ($CNP_{ring}$), and a C-terminal Ang-(1-7) in accordance with some embodiments.
Figure 16:
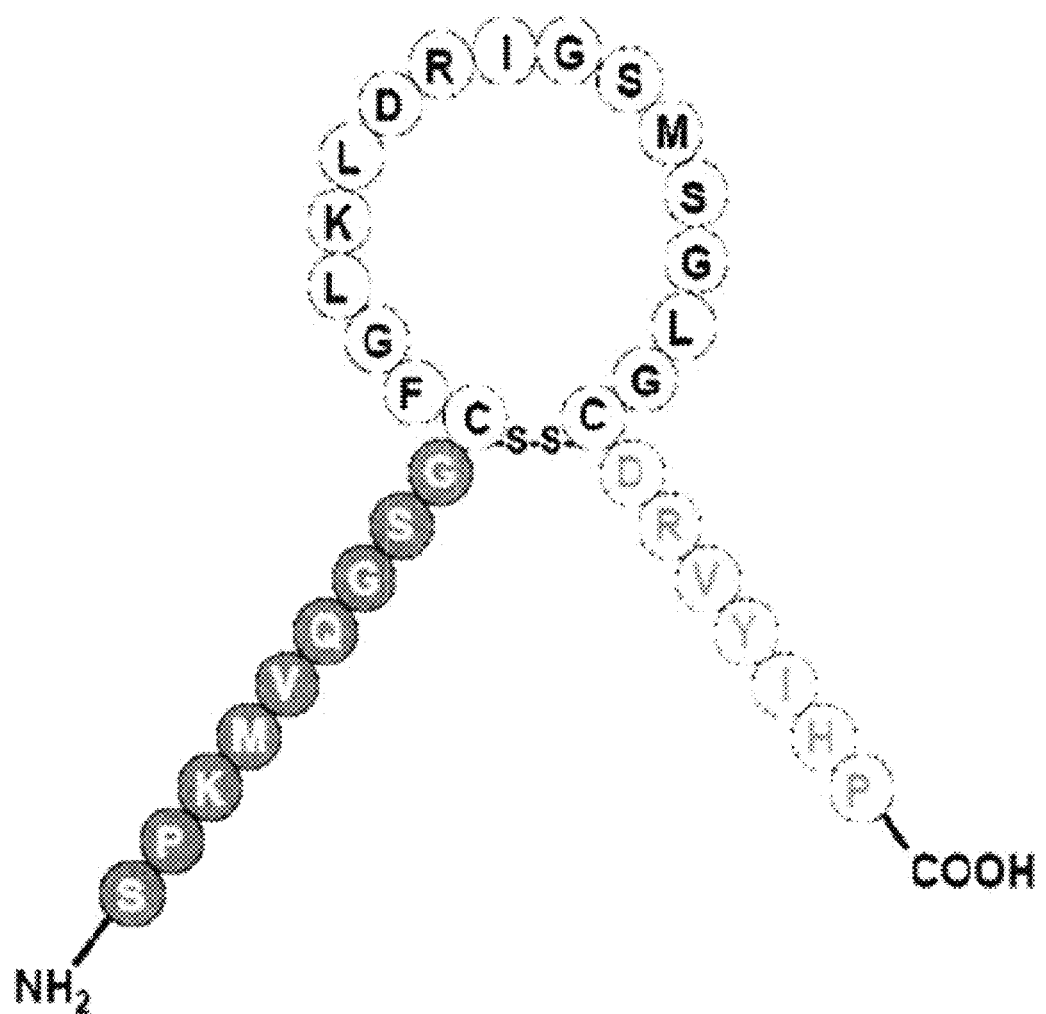
FIG. 16 is a structural schematic of a chimeric polypeptide (SEQ ID NO:57) containing an N-terminus of BNP ($BNP_{N-term}$), a ring structure of CNP ($CNP_{ring}$), and a C-terminal Ang-(1-7) in accordance with some embodiments.
Figure 17:
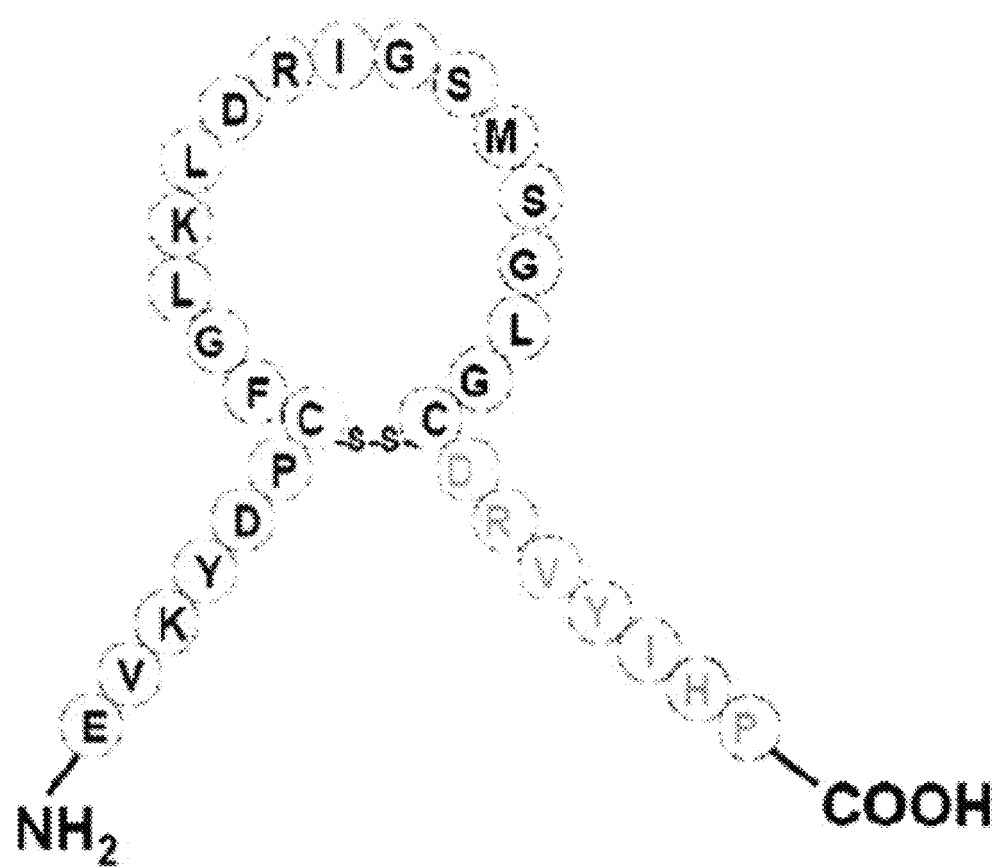
FIG. 17 is a structural schematic of a chimeric polypeptide (SEQ ID NO:58) containing an N-terminus of DNP ($DNP_{N-term}$), a ring structure of CNP ($CNP_{ring}$), and a C-terminal Ang-(1-7) in accordance with some embodiments.
Figure 18:
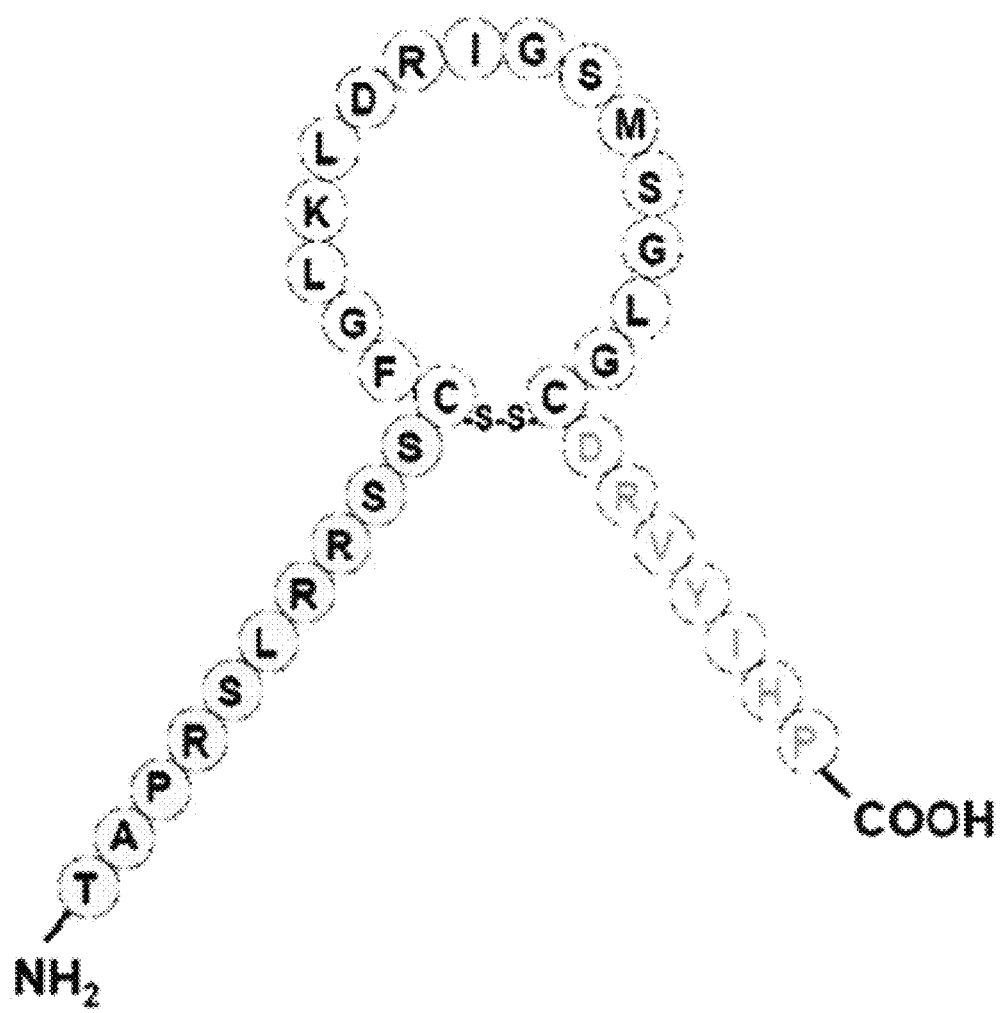
FIG. 18 is a structural schematic of a chimeric polypeptide (SEQ ID NO:59) containing an N-terminus of URO ($URO_{N-term}$), a ring structure of CNP ($CNP_{ring}$), and a C-terminal Ang-(1-7) in accordance with some embodiments.
Figure 19:
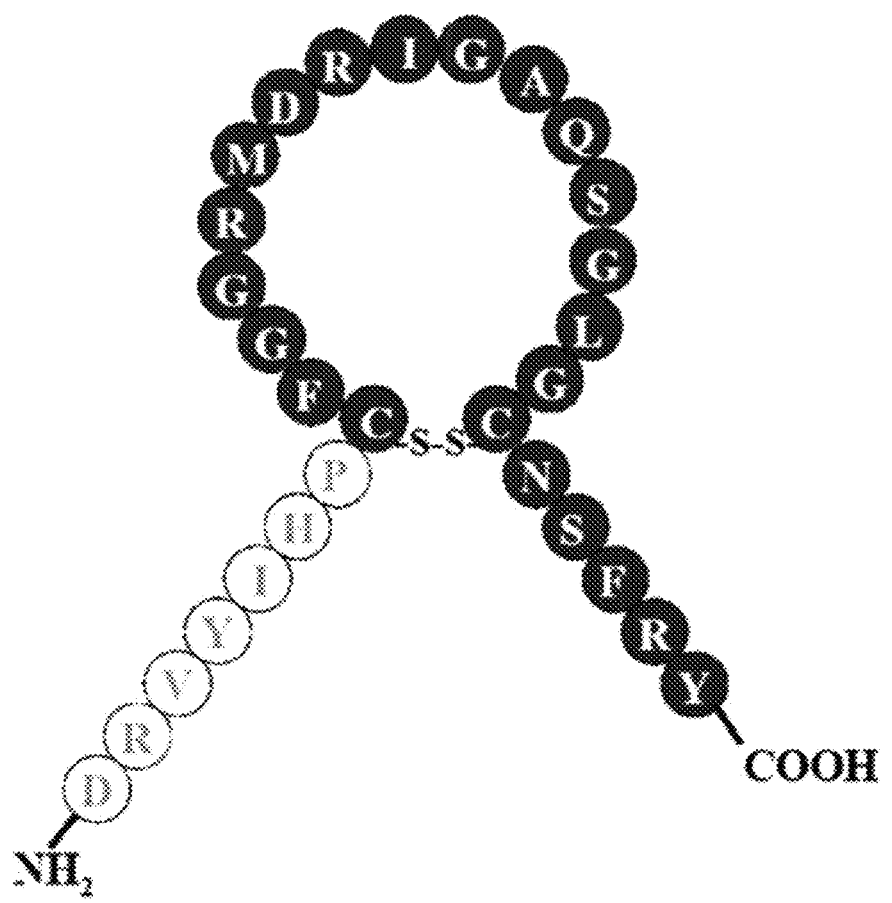
FIG. 19 is a structural schematic of a chimeric polypeptide (SEQ ID NO:60) containing an N-terminal Ang-(1-7) and a ring structure ($ANP_{ring}$) and C-terminus of ANP in accordance with some embodiments. The amino acid sequence of the C-terminal segment of ANP shown in FIG. 19 (NSFRY; SEQ ID NO:12) can be referred to as $ANP_{C-term}$.
Figure 20:
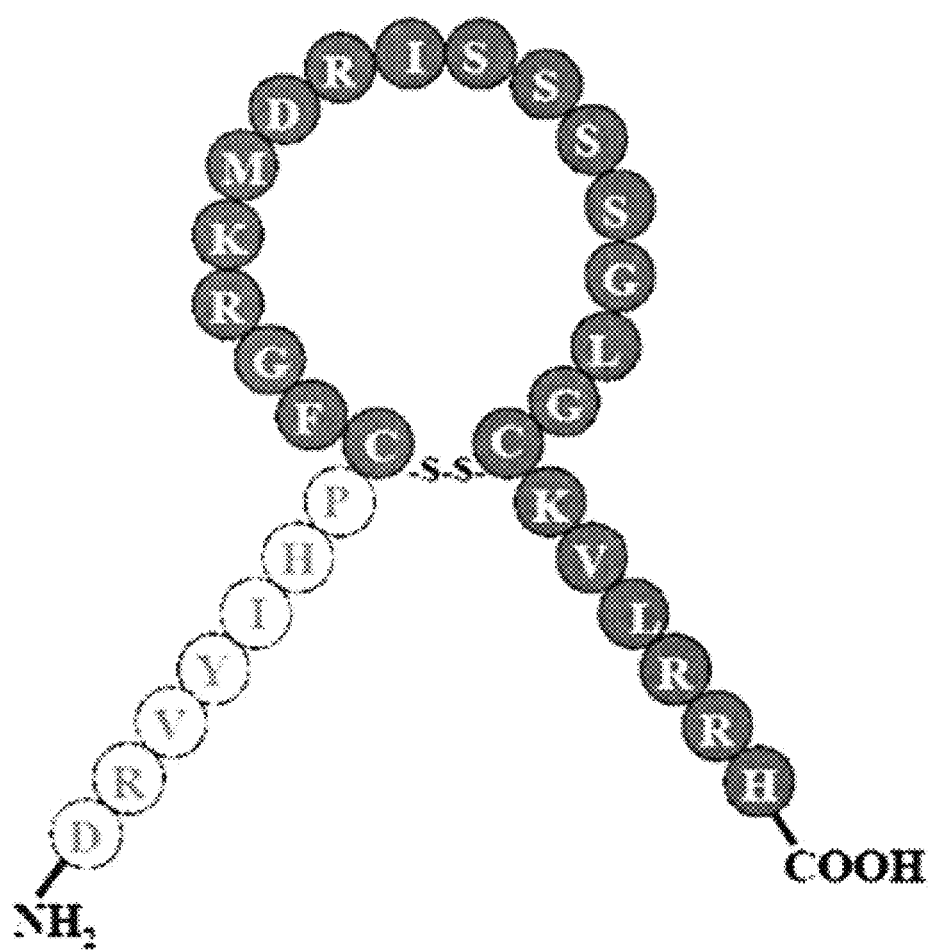
FIG. 20 is a structural schematic of a chimeric polypeptide (SEQ ID NO:61) containing an N-terminal Ang-(1-7) and a ring structure ($BNP_{ring}$) and C-terminus of BNP in accordance with some embodiments. The amino acid sequence of the C-terminal segment of BNP shown in FIG. 20 (KVLRRH; SEQ ID NO:13) can be referred to as $BNP_{C-term}$. The chimeric polypeptide having the amino acid sequence set forth in SEQ ID NO:61 can be referred to as Ang1-7BNP.

With reference to FIG. 1, a chimeric polypeptide provided herein can include an N-terminus and ring structure of a natriuretic peptide and a C-terminal Ang-(1-7). In some cases, the N-terminus and ring structure can be of the same natriuretic peptide (see, e.g., FIGS. 2-6) or of different natriuretic peptides (see, e.g., FIG. 7-18). For example, a chimeric polypeptide provided herein can have $BNP_{N-term}$ followed by $BNP_{ring}$ followed by Ang-(1-7) as shown in FIG. 3 or can have $ANP_{N-term}$ followed by $BNP_{ring}$ followed by Ang-(1-7) as shown in FIG. 11. In some cases, a chimeric polypeptide provided herein can include an N-terminal Ang-(1-7) followed by a ring structure and C-terminus of a natriuretic peptide as shown in FIGS. 19 and 20.

In some cases, an N-terminus, ring structure, reverse ring structure, and/or C-terminus of an NP included in a chimeric polypeptide provided herein can include a variant (e.g., a substitution, addition, or deletion) at one or more positions (e.g., one, two, three, four, five, six, seven, eight, nine, or ten positions). Such variant NP sequences, e.g., those having one or more amino acid substitutions relative to a native NP amino acid sequence, can be prepared and modified as described herein. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenyalanine, glycine for proline, threonine for serine, serine for threonine, tyrosine for tryptophan, phenylalanine for tyrosine, and/or leucine for valine.

Examples of variant N-terminal portions of NP sequences that can be used to make a chimeric polypeptide provided herein include, without limitation, SAPRSLRRSS (SEQ ID NO:15), TVPRSLRRSS (SEQ ID NO:16), TAGRSLRRSS (SEQ ID NO:17), TAPKSLRRSS (SEQ ID NO:18), TLRRSS (SEQ ID NO:19), SIRRSS (SEQ ID NO:20), SLKRSS (SEQ ID NO:21), and SLRKSS (SEQ ID NO:22). Examples of variant C-terminal portions of NP sequences that can be used to make a chimeric polypeptide provided herein include, without limitation, KVLRRR (SEQ ID NO:23), KVLRKH (SEQ ID NO:24), KVLKRH (SEQ ID NO:25), and KVIRRH (SEQ ID NO:26).

Further examples of conservative substitutions that can be made at any position within an NP amino acid sequence used to make a chimeric polypeptide provided herein include, without limitation, those set forth in Table 1.

TABLE 1

Examples of conservative amino acid substitutions.

| Original Residue | Exemplary substitutions |
|---|---|
| Ala | Val, Leu, Ile |
| Arg | Lys, Gln, Asn |

TABLE 1-continued

Examples of conservative amino acid substitutions.

| Original Residue | Exemplary substitutions |
|---|---|
| Asn | Gln, His, Lys, Arg |
| Asp | Glu |
| Cys | Ser |
| Gln | Asn |
| Glu | Asp |
| Gly | Pro |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn |
| Met | Leu, Phe, Ile |
| Phe | Leu, Val, Ile, Ala |
| Pro | Gly |
| Ser | Thr |
| Thr | Ser |
| Trp | Tyr |
| Tyr | Trp, Phe, Thr, Ser |
| Val | Ile, Leu, Met, Phe, Ala, Norleucine |

In some cases, an NP amino acid sequence used to make a chimeric polypeptide provided herein can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the peptide variant.

A chimeric polypeptide provided herein can have any appropriate sequence. For example, a polypeptide can include the sequences set forth in SEQ ID NOs:2, 3, and 1. In some cases, a chimeric polypeptide provided herein can contain (a) an amino acid sequence that aligns to the sequence set forth in SEQ ID NO:1 with three or less (e.g., two or less, one, or zero) amino acid additions, deletions, substitutions, or combinations thereof and (b) an amino acid sequence that aligns to the sequence of $ANP_{ring}$, $BNP_{ring}$, $CNP_{ring}$, $DNP_{ring}$, or $URO_{ring}$ with five or less (e.g., four or less, three or less, two or less, one, or zero) amino acid additions, deletions, substitutions, or combinations thereof. In some cases, a chimeric polypeptide provided herein can contain (a) an amino acid sequence that aligns to the sequence set forth in SEQ ID NO:1 with three or less (e.g., two or less, one, or zero) amino acid additions, deletions, substitutions, or combinations thereof followed by (b) an amino acid sequence that aligns to the sequence of $ANP_{ring}$, $BNP_{ring}$, $CNP_{ring}$, $DNP_{ring}$, or $URO_{ring}$ with five or less (e.g., four or less, three or less, two or less, one, or zero) amino acid additions, deletions, substitutions, or combinations thereof followed by (c) an amino acid sequence that aligns to the sequence of $ANP_{C\text{-}term}$, $BNP_{C\text{-}term}$, or a $DNP_{C\text{-}term}$ sequence with five or less (e.g., four or less, three or less, two or less, one, or zero) amino acid additions, deletions, substitutions, or combinations thereof. In some cases, a chimeric polypeptide provided herein can contain (a) an amino acid sequence that aligns to the sequence of $ANP_{N\text{-}term}$, $BNP_{N\text{-}term}$, $CNP_{N\text{-}term}$, $DNP_{N\text{-}term}$, or $URO_{N\text{-}term}$ with five or less (e.g., four or less, three or less, two or less, one, or zero) amino acid additions, deletions, substitutions, or combinations thereof followed by (b) an amino acid sequence that aligns to the sequence of $ANP_{ring}$, $BNP_{ring}$, $CNP_{ring}$, $DNP_{ring}$, or $URO_{ring}$ with five or less (e.g., four or less, three or less, two or less, one, or zero) amino acid additions, deletions, substitutions, or combinations thereof followed by an amino acid sequence that aligns to the sequence set forth in SEQ ID NO:1 with three or less (e.g., two or less, one, or zero) amino acid additions, deletions, substitutions, or combinations.

A polypeptide provided herein can have any appropriate length. For example, a polypeptide provided herein can be between 20 and 55 (e.g., between 24 and 55, between 24 and 45, between 25 and 45, between 26 and 44, between 27 and 43, between 28 and 42, between 29 and 41, between 30 and 40, between 31 and 39, between 23 and 35, between 25 and 30, or between 30 and 35) amino acid residues in length. It will be appreciated that a polypeptide with a length of 20 or 55 amino acid residues is a polypeptide with a length between 20 and 55 amino acid residues.

Chimeric polypeptides provided herein as well as polypeptides containing a variant NP sequence with conservative and/or non-conservative substitutions (e.g., with respect to a natural ANP, BNP, CNP, DNP, or URO), fragments of ANP, BNP, CNP, DNP, or URO, or fragments of such variants can be assessed for biological activity using any suitable assay including, without limitation, those described herein. For example, the activity of a chimeric polypeptide having a variant NP amino acid sequence as described herein can be evaluated in vitro by measuring its effect on cGMP levels generated by cardiac fibroblasts (CFs) or by testing its ability to suppress proliferation of CFs. Such experiments can be performed, for example, in human CFs (ScienCell, San Diego, Calif.) as described elsewhere (Tsuruda et al., *Circ. Res.* 91:1127-1134 (2002)). Cells can be exposed to a polypeptide to be assessed (e.g., $10^{-11}$ to $10^{-6}$M), and samples can be assayed for cGMP using a competitive RIA cGMP kit (Perkin-Elmer, Boston, Mass.). For CF proliferation studies, cells can be treated with Cardiotrophin-1 to induce cell proliferation. A polypeptide to be assessed can be added to the Cardiotrophin-1-stimulated CFs to determine its effect on cell proliferation. Cell proliferation can be detected and measured using, for example, a colormetric bromodeoxyuridine (BrdU) cell proliferation ELISA (Roche, Indianapolis, Ind.).

In some cases, a chimeric polypeptide provided herein, a polypeptide containing a variant NP sequence with conservative and/or non-conservative substitutions (e.g., with respect to a natural ANP, BNP, CNP, DNP, or URO), a fragment of ANP, BNP, CNP, DNP, or URO, or a fragment of such variants can be assessed in vivo by, for example, testing its effects on factors such as pulmonary capillary wedge pressure, right atrial pressure, mean arterial pressure, urinary sodium excretion, urine flow, proximal and distal fractional sodium reabsorption, plasma renin activity, plasma cGMP levels, urinary cGMP excretion, net renal generation of cGMP, glomerular filtration rate, and left ventricular mass in animals. In some cases, such parameters can be evaluated after induced myocardial infarction (e.g., myocardial infarction induced by coronary artery ligation).

In some embodiments, a chimeric polypeptide provided herein can be cyclic due to disulfide bonds between cysteine residues (see, e.g., the structures depicted in FIGS. 1-20). In some embodiments, a sulfhydryl group on a cysteine residue can be replaced with an alternative group (e.g., $—CH_2CH_2—$). To replace a sulfhydryl group with a $—CH_2—$ group, for example, a cysteine residue can be replaced by alpha-aminobutyric acid. Such cyclic analog polypeptides can be generated, for example, as described elsewhere (Lebl and Hruby, *Tetrahedron Lett.,* 25:2067 (1984) and U.S. Pat. No. 4,161,521).

In some cases, ester or amide bridges can be formed by reacting the OH of serine or threonine with the carboxyl group of aspartic acid or glutamic acid to yield a bridge having the structure —$CH_2CO_2CH_2$—. In some cases, an amide can be obtained by reacting the side chain of lysine with aspartic acid or glutamic acid to yield a bridge having the structure —$CH_2C(O)NH(CH)_4$—. Methods for synthesis of these bridges are described elsewhere (see, e.g., Schiller et al., *Biochem. Biophy. Res. Comm.*, 127:558 (1985), and Schiller et al. *Int. J. Peptide Protein Res.*, 25:171 (1985)). Other bridge-forming amino acid residues and reactions are provided in, for example, U.S. Pat. No. 4,935,492. In some cases, peptide analogs that include non-peptidyl bonds can be used to link amino acid residues of a chimeric polypeptide provided herein as described elsewhere (See, e.g., Spatola et al., *Life Sci.*, 38:1243 (1986); Spatola, *Vega Data*, 1(3) (1983); Morley, *Trends Pharm. Sci.*, 463-468 (1980); Hudson et al., *Int. J. Pept. Prot. Res.*, 14:177 (1979); Spatola, in *Chemistry and Biochemistry of Amino Acid Peptides and Proteins*, B. Weinstein, ed., Marcel Dekker, New York, p. 267 (1983); Hann, *J. Chem. Soc. Perkin Trans.*, 1:307 (1982); Almquist et al., *J. Med. Chem.* 23:1392 (1980); Jennings-White et al., *Tetrahedron Lett.*, 23:2533 (1982); European Patent Application EP 45665; Holladay et al., *Tetrahedron Lett.*, 24:4401 (1983); and Hruby, *Life Sci.*, 31:189 (1982).

In some cases, a chimeric polypeptide provided herein can have an amino acid sequence with at least 85% (e.g., 85%, 86%, 87%, 88%, 89%, 90%, 91%, 92%, 93%, 94%, 95%, 96%, 97%, 98%, 99%, or 100%) sequence identity to a reference sequence (e.g., SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61). Percent sequence identity is calculated by determining the number of matched positions in aligned amino acid sequences (target amino acid sequence aligned to an identified amino acid sequence), dividing the number of matched positions by the number of amino acids of the identified amino acid sequence (e.g., SEQ ID NO:3), and multiplying by 100. A matched position refers to a position in which identical amino acids occur at the same position in aligned amino acid sequences. Percent sequence identity also can be determined for any nucleic acid sequence.

Percent sequence identity is determined by comparing a target amino acid sequence to the identified amino acid sequence (e.g., SEQ ID NO:3) using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

For example, if (1) a target sequence is compared to the sequence set forth in SEQ ID NO:3 and (2) the Bl2seq program presents the target sequence aligned with a region of the sequence set forth in SEQ ID NO:3 with the number of matches being 15, then the amino acid target sequence has a percent identity to SEQ ID NO:3 that is 88.2 (i.e., 15÷17×100=88.2). It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

A chimeric polypeptide provided herein can be produced using any suitable method, including solid phase synthesis, and can be generated using manual techniques or automated techniques (e.g., using an Applied BioSystems (Foster City, Calif.) Peptide Synthesizer or a Biosearch Inc. (San Rafael, Calif.) automatic peptide synthesizer). Disulfide bonds between cysteine residues can be introduced by mild oxidation of the linear polypeptides using KCN as described elsewhere (U.S. Pat. No. 4,757,048). In some cases, a chimeric polypeptide provided herein can be produced recombinantly, as described herein.

In some cases, a chimeric polypeptide provided herein can be a substantially pure polypeptide. As used herein, the term "substantially pure" with reference to a polypeptide means that the polypeptide is substantially free of other polypeptides, lipids, carbohydrates, and nucleic acid. In some cases, a substantially pure polypeptide can be a polypeptide that is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

Salts of carboxyl groups of a chimeric polypeptide provided herein can be prepared by contacting the polypeptide with one or more equivalents of a desired base such as, for example, a metallic hydroxide base (e.g., sodium hydroxide), a metal carbonate or bicarbonate base (e.g., sodium carbonate or sodium bicarbonate), or an amine base (e.g., triethylamine, triethanolamine, and the like). Acid addition salts of a chimeric polypeptide provided herein can be prepared by contacting the polypeptide with one or more equivalents of an inorganic or organic acid (e.g., hydrochloric acid).

Esters of carboxyl groups of a chimeric polypeptide provided herein can be prepared using any suitable means for converting a carboxylic acid or precursor to an ester. For example, one method for preparing esters of a chimeric polypeptide provided herein, when using the Merrifield synthesis technique, is to cleave the completed polypeptide from the resin in the presence of the desired alcohol under either basic or acidic conditions, depending upon the resin. The C-terminal end of the polypeptide then can be directly esterified when freed from the resin, without isolation of the free acid.

Amides of a chimeric polypeptide provided herein can be prepared using techniques for converting a carboxylic acid group or precursor to an amide. One method for amide formation at the C-terminal carboxyl group includes cleaving the polypeptide from a solid support with an appropriate amine, or cleaving in the presence of an alcohol, yielding an ester, followed by aminolysis with the desired amine.

N-acyl derivatives of an amino group of a chimeric polypeptide provided herein can be prepared by utilizing an N-acyl protected amino acid for the final condensation, or by acylating a protected or unprotected polypeptide. O-acyl derivatives can be prepared for example, by acylation of a free hydroxy peptide or peptide resin. Either acylation may be carried out using standard acylating reagent such as acyl halides, anhydrides, acyl imidazoles, and the like. Both N- and O-acylation may be carried out together, if desired.

In some cases, a chimeric polypeptide provided herein can be modified by linkage to a polymer such as polyethylene glycol (PEG), or by fusion to another polypeptide such as albumin, for example. For example, one or more PEG moieties can be conjugated to a chimeric polypeptide provided herein via lysine residues. Linkage to PEG or another suitable polymer, or fusion to albumin or another suitable polypeptide can result in a modified chimeric polypeptide having an increased half life as compared to an unmodified chimeric polypeptide. Without being bound by a particular mechanism, an increased serum half life can result from reduced proteolytic degradation, immune recognition, or cell scavanging of the modified chimeric polypeptide. Any appropriate method can be used to modify a chimeric polypeptide by linkage to PEG (also referred to as "PEGylation") or other polymers including, without limitation, those described elsewhere (U.S. Pat. No. 6,884,780; Cataliotti et al., *Trends Cardiovasc. Med.,* 17: 10-14 (2007); Veronese and Mero, *BioDrugs,* 22:315-329 (2008); Miller et al., *Bioconjugate Chem.,* 17:267-274 (2006); and Veronese and Pasut, *Drug Discov. Today,* 10:1451-1458 (2005). Examples of methods for modifying a chimeric polypeptide by fusion to albumin include, without limitation, those described elsewhere (U.S. Patent Publication No. 20040086976, and Wang et al., *Pharm. Res.,* 21:2105-2111 (2004)).

The term "cardiac remodeling" refers to effects on the heart that can occur with myocardial infarction, acute heart failure, or other conditions. These include, for example, heart dilation, myocyte hypertrophy, and cardiofibrosis (i.e., proliferation of interstitial fibroblasts). The chimeric polypeptides provided herein can be used to inhibit or prevent cardiac remodeling that occurs with myocardial infarction or acute heart failure. In some cases, parameters indicative of reduced cardiac remodeling can include one or more of the following: cardiac unloading (i.e., reduced pressure in the heart), increased glomerular filtration rate (GFR), decreased plasma renin activity (PRA), decreased levels of angiotensin II, decreased proliferation of cardiac fibroblasts, decreased left ventricular (LV) hypertrophy, decreased LV mass (indicative of reduced fibrosis and hypertrophy), decreased pulmonary capillary wedge pressure (PCWP; an indirect measure of left atrial pressure), decreased right atrial pressure, decreased mean arterial pressure, decreased levels of aldosterone (indicative of an anti-fibrotic effect), decreased ventricular fibrosis, increased ejection fraction, and decreased LV end systolic diameter. To determine whether a chimeric polypeptide provided herein is capable of inhibiting or reducing cardiac remodeling, one or more of these parameters can be evaluated (e.g., before and after treatment with the chimeric polypeptide, using methods known in the art and/or described herein, for example. The use of human amino acid sequences to construct a chimeric polypeptide provided herein can minimize the risk of immunogenicity that may be observed with protein therapeutics, as compared to the use of amino acid sequences from other species (Haller et al., *Clin. Pharmacol. Ther,* 84:624-7 (2008); and Leader et al., *Nat. Rev. Drug Discov.,* 7:21-39 (2008)).

Conditions such as acute myocardial infarction (AMI) or acute heart failure (AHF) can lead to kidney damage as well as heart damage. In some cases, the chimeric polypeptides provided herein can protect the kidneys from damage after AMI and AHF. Parameters that are indicative of favorable renal actions include, for example, decreased proximal fractional reabsorption of sodium (PFRNa), decreased distal fractional reabsorption of sodium (DFRNa), increased urinary sodium excretion (UNaV), and increased urine flow (UV). Any one or more of these parameters can be assessed (e.g., before and after administration of a chimeric polypeptide) to determine whether the chimeric polypeptide has kidney protecting effects. Methods for assessing these parameters are known in the art, and also are described herein.

In some cases, a chimeric polypeptide provided herein can inhibit or reduce cardiac remodeling such as occurs after AMI or AHF, for example. A chimeric polypeptide that can inhibit cardiac remodeling is one that can alter one or more parameters indicative of inhibited or reduced cardiac remodeling by at least 10%. To determine whether a particular chimeric polypeptide has such properties, one can carry out assays that are well known to the art, including those described herein. A chimeric polypeptide that includes a variant NP sequence can have at least about 10% (e.g., at least about 10%, 15%, 20%, 25%, 33%, 40%, 50%, 60%, 67%, 75%, 80%, 85%, 90%, 95%, 100%, or more than 100%) of the biological activity of the corresponding wild type NP sequence.

Nucleic Acids, Vectors, and Host Cells

This document also provides nucleic acids encoding a chimeric polypeptide provided herein, as well as expression vectors containing the nucleic acids, and host cells containing the nucleic acids and/or expression vectors. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding the chimeric polypeptides provided herein.

An "isolated nucleic acid" is a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing a nucleotide sequence that encodes an angiotensin polypeptide or an NP. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding variant NPs) also can be obtained by mutagenesis. For example, a reference sequence can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Non-limiting examples of variant NPs art provided herein.

Sources of nucleotide sequences from which nucleic acid molecules encoding an NP, or the nucleic acid complement thereof, can be obtained include total or polyA$^+$ RNA from any eukaryotic source, including reptilian (e.g., snake) or mammalian (e.g., human, rat, mouse, canine, bovine, equine, ovine, caprine, or feline) cellular source from which cDNAs can be derived by methods known in the art. Other sources of the nucleic acid molecules include genomic libraries derived from any eukaryotic cellular source, including mammalian sources.

Nucleic acid molecules encoding native NPs can be identified and isolated using standard methods, e.g., as described by Sambrook et al., *Molecular Cloning: A Laboratory Manual*, Cold Spring Harbor Laboratory Press, NY (1989). For example, reverse-transcriptase PCR (RT-PCR) can be used to isolate and clone NP cDNAs from isolated RNA that contains RNA sequences of interest (e.g., total RNA isolated from human tissue). Other approaches to identify, isolate, and clone NP cDNAs include, for example, screening cDNA libraries.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors, a nucleic acid (e.g., a nucleic acid encoding a chimeric polypeptide provided herein) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid or vector provided herein. The term "host cell" is intended to include prokaryotic and eukaryotic cells into which a recombinant nucleic acid or vector (e.g., an expression vector) can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Suitable methods for transforming and transfecting host cells can be found, for example, in Sambrook et al., *Molecular Cloning: A Laboratory Manual* ($2^{nd}$ edition), Cold Spring Harbor Laboratory, New York (1989). For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document also provides methods and materials for detecting a chimeric polypeptide provided herein. Such methods and materials can be used to monitor chimeric polypeptide levels within a mammal receiving the chimeric polypeptide as a therapeutic. A chimeric polypeptide provided herein (e.g., a chimeric polypeptide as set forth in any one of FIGS. 2-20 and 23-32) can be detected, for example, immunologically using one or more antibodies. As used herein, the term "antibody" includes intact molecules as well as fragments thereof that are capable of binding to an epitopic determinant of a chimeric polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and $F(ab)_2$ fragments. Polyclonal antibodies are heterogeneous populations of antibody molecules that are contained in the sera of the immunized animals. Monoclonal antibodies are homogeneous populations of antibodies to a particular epitope of an antigen.

Antibody fragments that have specific binding affinity for a chimeric polypeptide provided herein (e.g., a chimeric polypeptide as set forth in any one of FIGS. 2-20 and 23-32) can be generated by known techniques. For example, F(ab')2 fragments can be produced by pepsin digestion of the antibody molecule, and Fab fragments can be generated by reducing the disulfide bridges of F(ab')2 fragments. In some cases, Fab expression libraries can be constructed. See, for example, Huse et al., *Science*, 246:1275 (1989). Once produced, antibodies or fragments thereof can be tested for recognition of a chimeric polypeptide provided herein by standard immunoassay methods including ELISA techniques, radioimmunoassays, and Western blotting. See, *Short Protocols in Molecular Biology*, Chapter 11, Green Publishing Associates and John Wiley & Sons, Ed. Ausubel et al., 1992.

In immunological assays, an antibody having specific binding affinity for a chimeric polypeptide provided herein or a secondary antibody that binds to such an antibody can be labeled, either directly or indirectly. Suitable labels include, without limitation, radionuclides (e.g., $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive IA), or bridge immunoassays. See, for example, U.S. Pat. Nos. 5,296,347; 4,233,402; 4,098,876; and 4,034,074. Methods of detecting a chimeric polypeptide provided herein generally include contacting a biological sample with an antibody that binds to a chimeric polypeptide provided herein and detecting binding of the chimeric polypeptide to the antibody. For example, an antibody having specific binding affinity for a chimeric polypeptide provided herein can be immobilized on a solid substrate by any of a variety of methods known in the art and then exposed to the biological sample. Binding of the chimeric polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a chimeric polypeptide provided herein can be generated to aid in the quantitation of the levels of the chimeric polypeptide.

In some embodiments, a "sandwich" assay in which a capture antibody is immobilized on a solid substrate can be used to detect the presence, absence, or level of a chimeric polypeptide provided herein. The solid substrate can be contacted with the biological sample such that any chimeric polypeptide of interest in the sample can bind to the immobilized antibody. The presence, absence, or level of the chimeric polypeptide bound to the antibody can be determined using a "detection" antibody having specific binding affinity for the chimeric polypeptide. In some embodiments, a capture antibody can be used that has binding affinity for ANP, BNP, CNP, DNP, URO, or an angiotensin polypeptide as well as a chimeric polypeptide provided herein. In this embodiment, a detection antibody can be used that has specific binding affinity for a particular chimeric polypeptide provided herein (e.g., a chimeric polypeptide as set forth in any one of FIGS. 2-20 and 23-32). It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a chimeric polypeptide provided herein can be produced through standard methods. For example, a chimeric polypeptide can be recombinantly produced as described above or can be chemically synthesized, and used to immunize host animals, including rabbits, chickens, mice, guinea pigs, or rats. For example, a chimeric polypeptide as set forth in any one of FIGS. 2-20 and 23-32 can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a chimeric polypeptide provided herein and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci. USA*, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

In some cases, antibodies directed to either an NP sequence or the sequence of an angiotensin polypeptide or a combination of both types of antibodies can be used to detect a chimeric polypeptide provided herein (e.g., a chimeric polypeptide as set forth in any one of FIGS. 2-20 and 23-32).

Other techniques for detecting a chimeric polypeptide provided herein include mass-spectrophotometric techniques such as electrospray ionization (ESI), and matrix-assisted laser desorption-ionization (MALDI). See, for example, Gevaert et al., *Electrophoresis*, 22:1645-51 (2001); Chaurand et al., *J. Am. Soc. Mass Spectrom.*, 10:91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

Compositions and Methods for Administration

A chimeric polypeptide provided herein (e.g., a chimeric polypeptide as set forth in any one of FIGS. 2-20 and 23-32), or a nucleic acid encoding a chimeric polypeptide provided herein, can be incorporated into a composition for administration to a mammal (e.g., a human suffering from or at risk for AMI or AHF). Methods for formulating and subsequently administering therapeutic compositions are well known to those in the art. Dosages typically are dependent on the responsiveness of the subject to the compound, with the course of treatment lasting from several days to several months, or until a suitable response is achieved. Persons of ordinary skill in the art routinely determine optimum dosages, dosing methodologies, and repetition rates. Optimum dosages can vary depending on the relative potency of a chimeric polypeptide, and generally can be estimated based on the $EC_{50}$ found to be effective in in vitro and/or in vivo animal models. Compositions containing a chimeric polypeptide provided herein or a nucleic acid provided herein may be given once or more daily, weekly, monthly, or even less often, or can be administered continuously for a period of time (e.g., hours, days, or weeks). For example, a chimeric polypeptide provided herein or a composition containing a chimeric polypeptide provided herein can be administered to an myocardial infarction patient at a dose of at least about 0.01 ng polypeptide/kg to about 100 mg polypeptide/kg of body mass at or about the time of reperfusion, or can be administered continuously as an infusion beginning at or about the time of reperfusion and continuing for one to seven days (e.g., at a dose of about 0.01 ng polypeptide/kg/minute to about 0.5 µg polypeptide/kg/minute).

The chimeric polypeptides or nucleic acids can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain a chimeric polypeptide provided herein in combination with a pharmaceutically acceptable carrier. Pharmaceutically acceptable carriers include, for example, pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing a chimeric polypeptide provided herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions (e.g., a chimeric polypeptide provided herein).

In some cases, a chimeric polypeptide provided herein can be formulated as a sustained release dosage form. In some cases, coatings, envelopes, or protective matrices can be formulated to contain one or more of the chimeric polypeptides provided herein. Such coatings, envelopes, and protective matrices can be used to coat indwelling devices such as stents, catheters, and peritoneal dialysis tubing. In some cases, a chimeric polypeptide provided herein can be incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association an active ingredient (e.g., a chimeric polypeptide provided herein) with the desired pharmaceutical carrier(s). Typically, the formulations can be prepared by uniformly and intimately bringing an active ingredient into association with liquid carriers or finely divided solid carriers or both, and then, if necessary, shaping the product. Formulations can be sterilized if desired, provided that the method of sterilization does not interfere with the effectiveness of the molecules(s) contained in the formulation (e.g., a chimeric polypeptide provided herein).

Methods for Reducing or Inhibiting Cardiac Remodeling

This document also provides for the use of a chimeric polypeptide provided herein for treatment of, for example, AHF and AMI. For example, a chimeric polypeptide provided herein can be administered to a mammal (e.g., a human or a non-human mammal) in order to reduce or inhibit cardiac remodeling that can occur, for example, after myocardial infarction. In some embodiments, for example, a chimeric polypeptide provided herein or a composition provided herein can be administered to a mammal diagnosed as having had an AMI. The chimeric polypeptide or composition can be administered at any suitable dose, depending on various factors including, without limitation, the agent chosen, the disease, and whether prevention or treatment is to be achieved. Administration can be local or systemic.

In some embodiments, a chimeric polypeptide provided herein or a composition containing a chimeric polypeptide provided herein can be administered at a dose of at least about 0.01 ng polypeptide/kg to about 100 mg polypeptide/kg of body mass (e.g., about 10 ng polypeptide/kg to about 50 mg polypeptide/kg, about 20 ng polypeptide/kg to about 10 mg polypeptide/kg, about 0.1 ng polypeptide/kg to about 20 ng polypeptide/kg, about 3 ng polypeptide/kg to about 10 ng polypeptide/kg, or about 50 ng polypeptide/kg to about 100 µg/kg) of body mass, although other dosages also may provide beneficial results. In some cases, a chimeric polypeptide provided herein or a composition containing a chimeric polypeptide provided herein can be administered as a continuous intravenous infusion beginning at or about the time of reperfusion (i.e., at the time the occluded artery is opened), and continuing for one to seven days (e.g., one, two, three, four, five, six, or seven days). Such a composition can be administered at a dose of, for example, about 0.1 ng polypeptide/kg/minute to about 500 ng polypeptide/kg/minute (e.g., about 0.5 ng polypeptide/kg/minute, about 1 ng polypeptide/kg/minute, about 2 ng polypeptide/kg/minute, about 3 ng polypeptide/kg/minute, about 5 ng polypeptide/kg/minute, about 7.5 ng polypeptide/kg/minute, about 10 ng polypeptide/kg/minute, about 12.5 ng polypeptide/kg/minute, about 15 ng polypeptide/kg/minute, about 20 ng polypeptide/kg/minute, about 25 ng polypeptide/kg/minute, about 30 ng polypeptide/kg/minute, about 50 ng polypeptide/kg/minute, about 100 ng polypeptide/kg/minute, or about 300 ng polypeptide/kg/minute). In some embodiments, a chimeric polypeptide provided herein or a composition containing a chimeric polypeptide provided herein can be administered before reperfusion (e.g., about one hour prior to reperfusion), either as one or more individual doses or as a continuous infusion beginning about one hour prior to reperfusion). For example, a composition can be administered beginning about one hour, about 45 minutes, about 30 minutes, or about 15 minutes prior to reperfusion. In some cases, a chimeric polypeptide provided herein or a composition containing a chimeric polypeptide provided herein can be administered after reperfusion (e.g., within about ten hours of reperfusion), and can be administered either as one or more individual doses or as a continuous infusion beginning within about ten hours of reperfusion. For example, a chimeric polypeptide provided herein or a composition containing a chimeric polypeptide provided herein can be administered about one hour, about two hours, about three hours, about four hours, about five hours, about six hours, about seven hours, about eight hours, about nine hours, or about ten hours after reperfusion.

In some embodiments, a chimeric polypeptide provided herein or a composition containing a chimeric polypeptide provided herein can be administered via a first route (e.g., intravenously) for a first period of time, and then can be administered via another route (e.g., topically or subcutaneously) for a second period of time. For example, a chimeric polypeptide provided herein or a composition containing a chimeric polypeptide provided herein can be intravenously administered to a mammal (e.g., a human) at a dose of about 0.1 ng polypeptide/kg/minute to about 300 ng polypeptide/kg/minute (e.g., about 1 ng polypeptide/kg/minute to about 15 ng polypeptide/kg/minute, about 3 ng polypeptide/kg/minute to about 10 ng polypeptide/kg/minute, or about 10 ng polypeptide/kg/minute to about 30 ng polypeptide/kg/minute) for one to seven days (e.g., one, two, three, four, five, six, or seven days), and subsequently can be subcutaneously administered to the mammal at a dose of about 10 ng polypeptide/kg/day to about 100 ng polypeptide/kg/day (e.g., about 10 ng polypeptide/kg/day, about 20 ng polypeptide/kg/day, about 25 ng polypeptide/kg/day, about 30 ng polypeptide/kg/day, about 50 ng polypeptide/kg/day, or about 100 ng polypeptide/kg/day) for five to 30 days (e.g., seven, 10, 14, 18, 21, 24, or 27 days).

The methods provided herein can include administering to a mammal an effective amount of a chimeric polypeptide provided herein or a composition containing a chimeric polypeptide provided herein. As used herein, the term "effective amount" is an amount of a molecule or composition that is sufficient to alter one or more (e.g., one, two, three, four, five, six, seven, eight, nine, or ten) parameters indicative of reduced cardiac remodeling and/or kidney protection in a mammalian recipient by at least 10% (e.g., 10%, 15%, 20%, 25%, 30%, 40%, 50%, 60%, 70%, 75%, 80%, 85%, 90%, 95%, 99%, or 100%). For example, an effective amount of a chimeric polypeptide provided herein or a composition containing a chimeric polypeptide provided herein is an amount that can increase ejection fraction, GFR, urinary sodium excretion (UNaV), or urine flow (UV) by at least 10%, and/or that can decrease PRA, LV mass, CF proliferation, PCWP, RAP, MAP, aldosterone levels, LV hypertrophy, ventricular fibrosis, LV end systolic diameter, PFRNa, or DFRNa by at least 10%, and/or that can result in cardiac unloading. In some embodiments, a method can include administering to a mammal an amount of a chimeric polypeptide provided herein or a composition containing a chimeric polypeptide provided herein that is sufficient to alter one or more parameters indicative of reduced cardiac remodeling and/or kidney protection by at least 50%.

In some embodiments, for example, an "effective amount" of a chimeric polypeptide provided herein or a composition containing a chimeric polypeptide provided herein can be an amount that reduces PRA and MAP and increases GFR and UV in a treated mammal by at least 10% as compared to the levels of those parameters in the mammal prior to administration of the chimeric polypeptide or composition or without administration of the chimeric polypeptide or composition (e.g., the level of the parameters observed in a previous myocardial infarction episode).

The invention will be further described in the following example, which does not limit the scope of the invention described in the claims.

EXAMPLE

Figure 4:
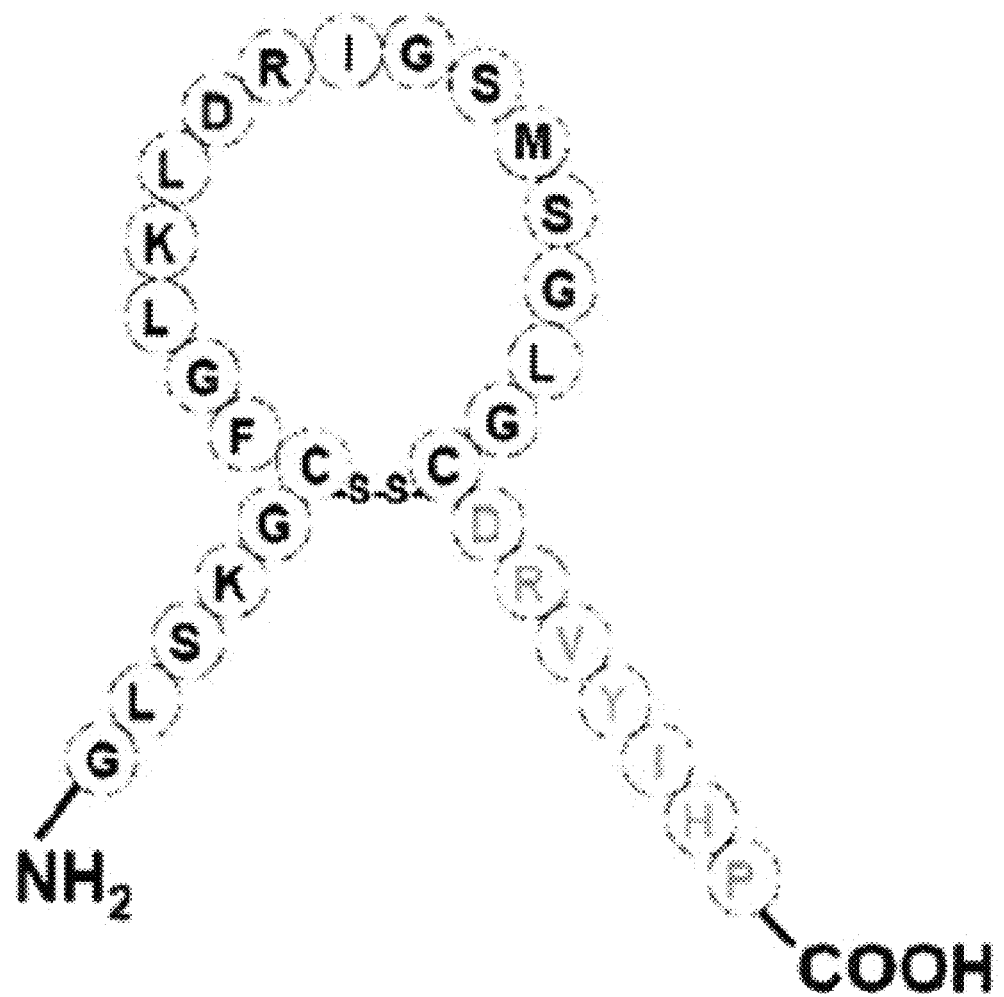
FIG. 4 is a structural schematic of a chimeric polypeptide (SEQ ID NO:45) containing an N-terminus and ring structure of CNP and a C-terminal Ang-(1-7) in accordance with some embodiments. The amino acid sequence of the N-terminal segment of CNP shown in FIG. 4 (GLSKG; SEQ ID NO:6) can be referred to as $CNP_{N-term}$, while the amino acid sequence of the ring structure segment of CNP shown in FIG. 4 (CFGLKLDRIG-SMSGLGC; SEQ ID NO:7) can be referred to as $CNP_{ring}$. The chimeric polypeptide shown in FIG. 4 can be referred to as cAng or cANG
Figure 5:
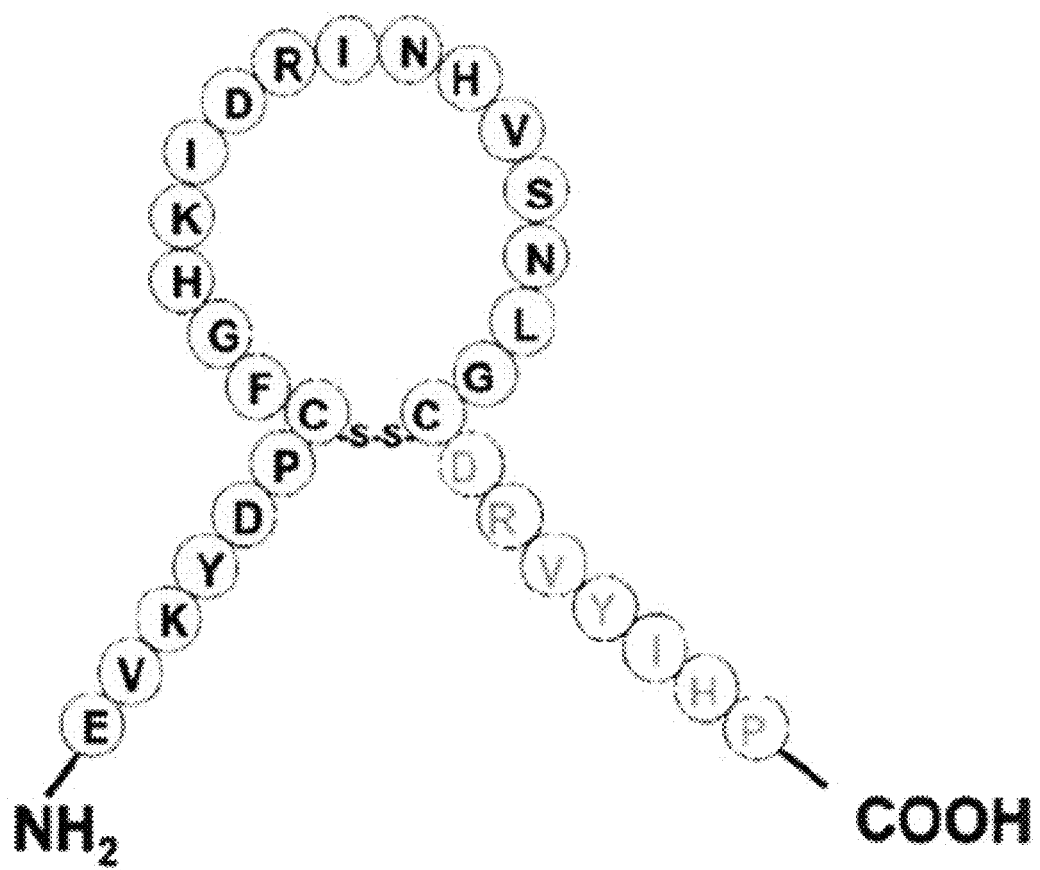
FIG. 5 is a structural schematic of a chimeric polypeptide (SEQ ID NO:46) containing an N-terminus and ring structure of DNP and a C-terminal Ang-(1-7) in accordance with some embodiments. The amino acid sequence of the N-terminal segment of DNP shown in FIG. 5 (EVKYDP; SEQ ID NO:8) can be referred to as $DNP_{N-term}$, while the amino acid sequence of the ring structure segment of DNP shown in FIG. 5 (CFGHKIDRINHVS-NLGC; SEQ ID NO:9) can be referred to as $DNP_{ring}$.
Figure 6:
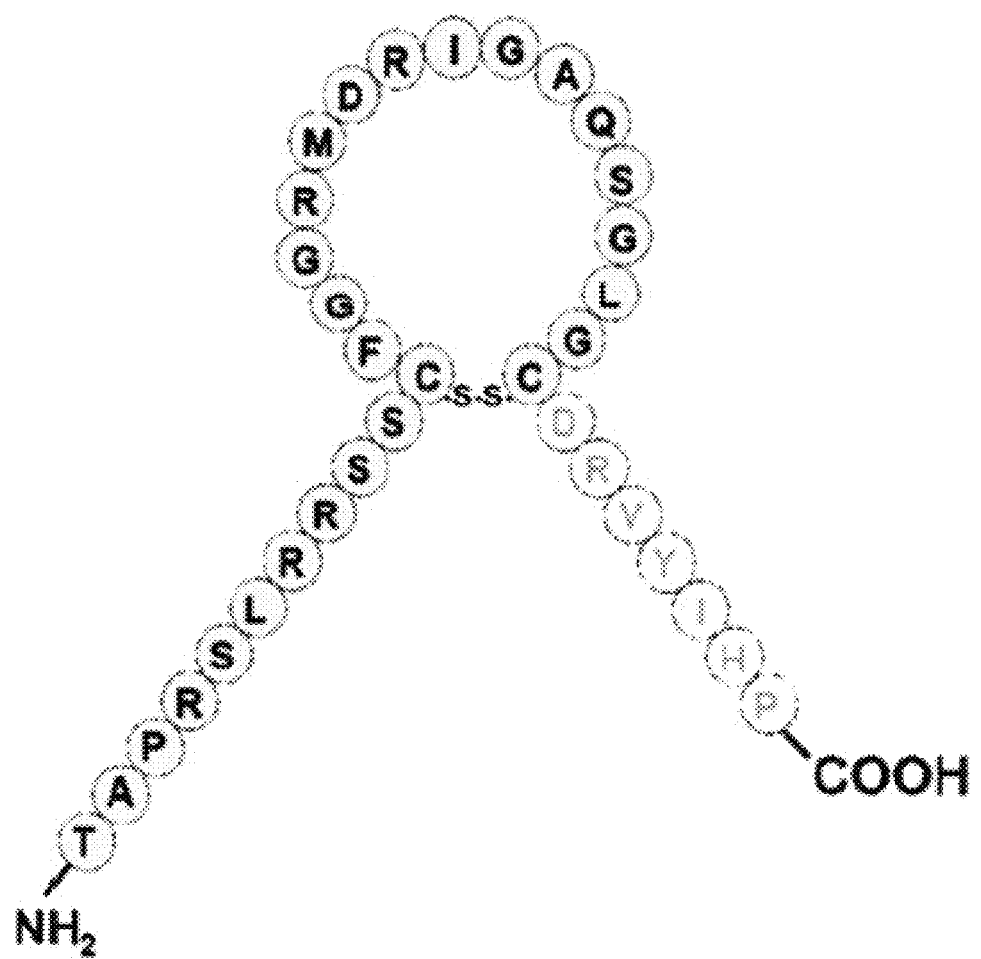
FIG. 6 is a structural schematic of a chimeric polypeptide (SEQ ID NO:47) containing an N-terminus and ring structure of URO and a C-terminal Ang-(1-7) in accordance with some embodiments. The amino acid sequence of the N-terminal segment of URO shown in FIG. 6 (TAPRSLRRSS; SEQ ID NO:10) can be referred to as $URO_{N-term}$, while the amino acid sequence of the ring structure segment of URO shown in FIG. 6 (CFGG-RMDRIGAQSGLGC; SEQ ID NO:11) can be referred to as $URO_{ring}$.
Figure 7:
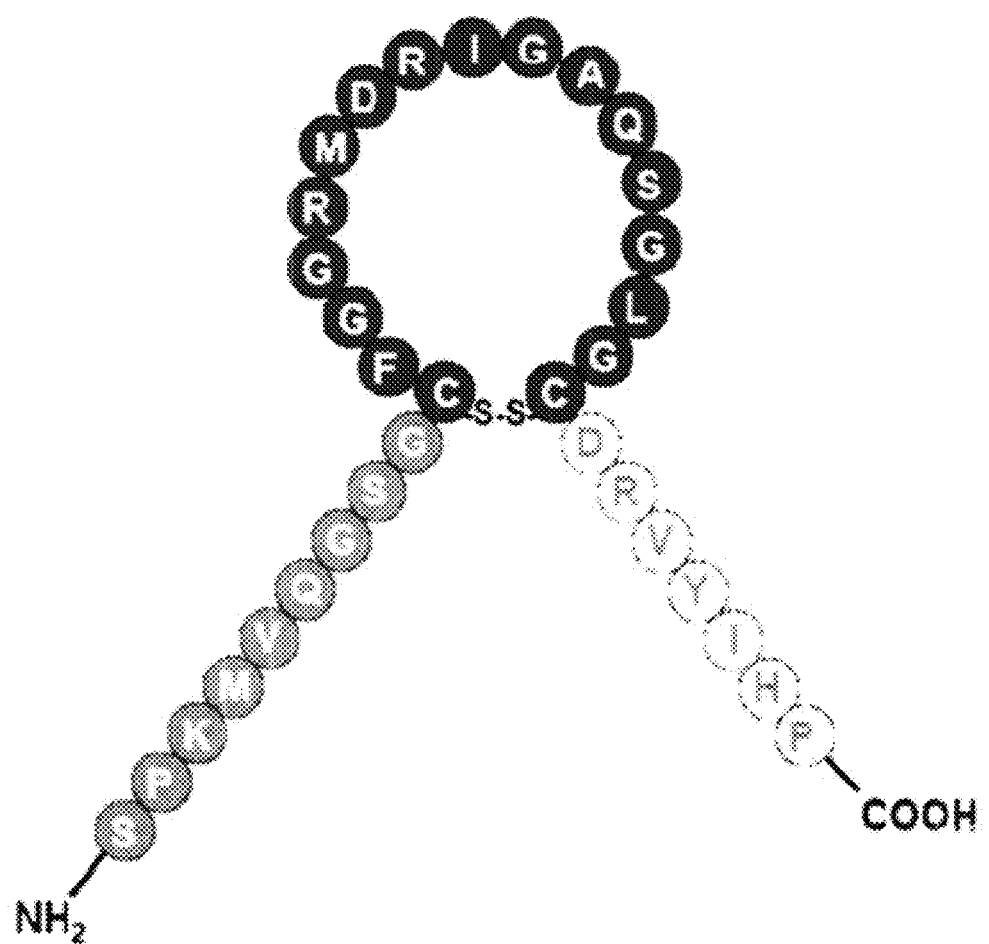
FIG. 7 is a structural schematic of a chimeric polypeptide (SEQ ID NO:48) containing an N-terminus of BNP ($BNP_{N-term}$), a ring structure of ANP ($ANP_{ring}$), and a C-terminal Ang-(1-7) in accordance with some embodiments.
Figure 8:
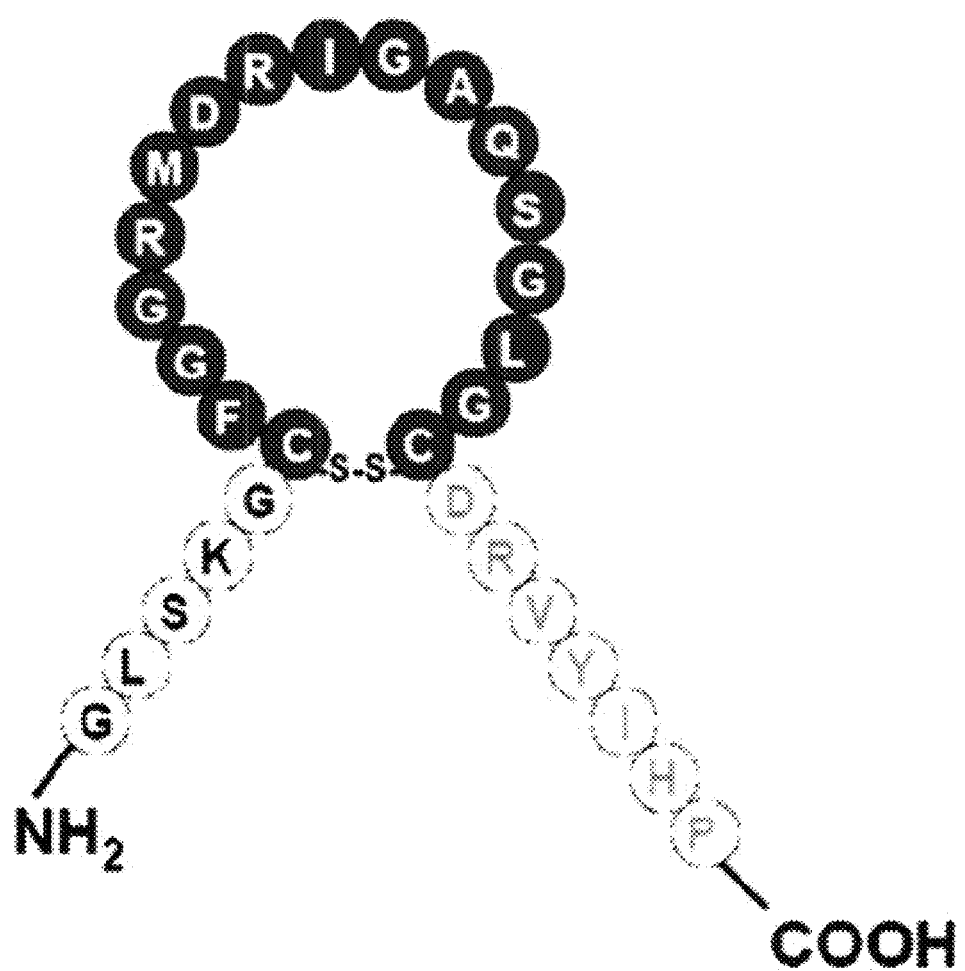
FIG. 8 is a structural schematic of a chimeric polypeptide (SEQ ID NO:49) containing an N-terminus of CNP ($CNP_{N-term}$), a ring structure of ANP ($ANP_{ring}$), and a C-terminal Ang-(1-7) in accordance with some embodiments.
Figure 9:
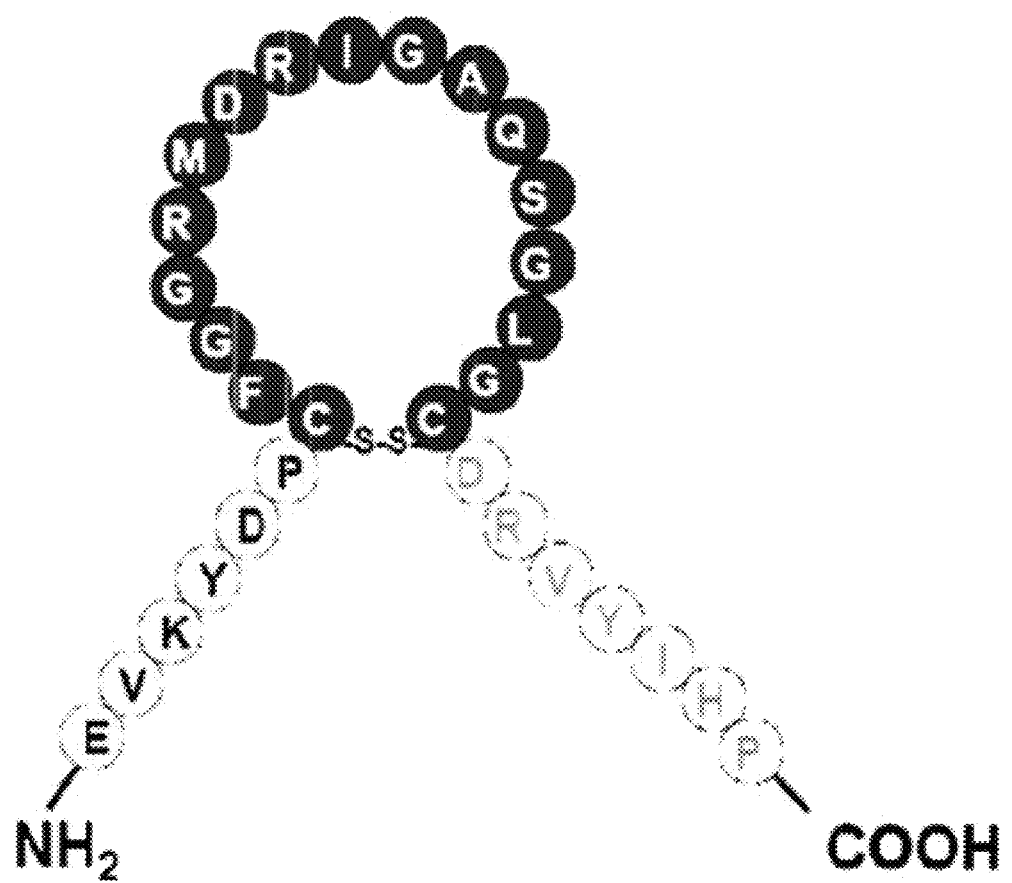
FIG. 9 is a structural schematic of a chimeric polypeptide (SEQ ID NO:50) containing an N-terminus of DNP ($DNP_{N-term}$), a ring structure of ANP ($ANP_{ring}$), and a C-terminal Ang-(1-7) in accordance with some embodiments.
Figure 10:
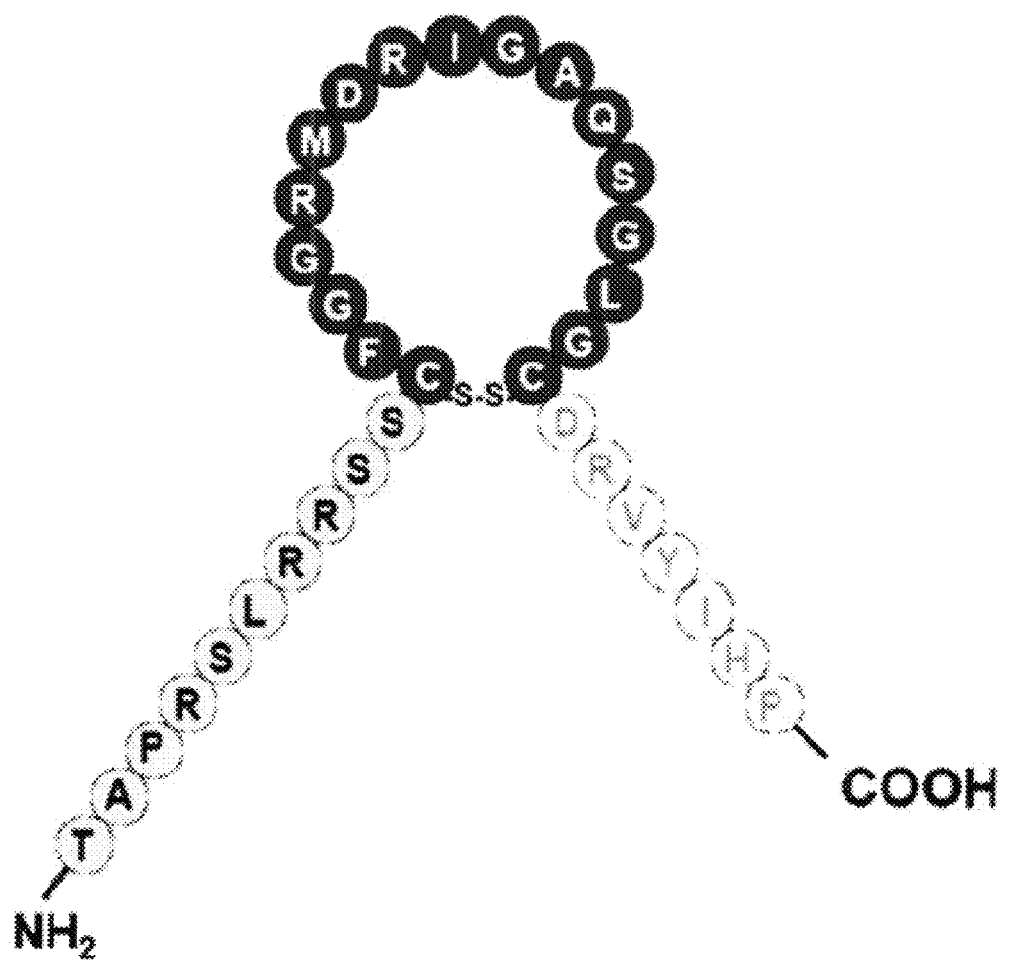
FIG. 10 is a structural schematic of a chimeric polypeptide (SEQ ID NO:51) containing an N-terminus of URO ($URO_{N-term}$), a ring structure of ANP ($ANP_{ring}$), and a C-terminal Ang-(1-7) in accordance with some embodiments.

Example 1—cANG Induce cGMP Production cANG was custom-synthesized to have the sequence set forth in FIG. 4 and confirmed by high performance liquid chromatography and mass spectroscopy to have a molecular weight of 3080.6 Da. Human cardiac fibroblasts (CFs; ScienCell, San Diego, Calif.) were cultured in the manufacturer's fibroblast media (ScienCell, San Diego, Calif.) supplemented with fibroblast growth serum (FGS), fetal bovine serum (FBS), and Pen/Strep. Cells were treated at 80-90% confluency. Only cell passages 1 through 4 were used for experiments. To perform a cyclic GMP assay, the cells were treated as described previously (Huntley et al., *J. Cell. Physiol.*, 209(3):943-9 (2006)). Briefly, cells were incubated in Hank's balanced salt solution (Invitrogen, Carlsbad, Calif.) containing 20 mmol/L N-[2-hydroxyethyl]piperazine-N'[2-ethanesulfonic acid], 0.1% bovine serum albumin, and 0.5 mmol/L 3-isobutyl-1-methylzanthine (Sigma, St. Louis, Mo.). Treated cells received $10^{-6}$ M, $10^{-8}$ M, or $10^{-10}$ M of NP or cANG for 10 minutes. Cells were lysed in 6% TCA and sonicated for 10 minutes. The samples were ether extracted four times in four volumes of ether, dried, and reconstituted in 500 ml of cGMP assay buffer.

The samples were assayed using a competitive RIA cGMP kit (Perkin-Elmer, Boston, Mass.). Briefly, samples and standards were incubated with 100 mL anti-human cGMP polyclonal antibody and $I^{125}$-antigen for 18 hours. Cyclic GMP assay buffer was added to the samples, and they were centrifuged for 20 minutes at 2500 rpm. The free fraction was aspirated off, and the bound fraction was counted and concentrations determined. Samples were corrected for dilution factors and protein concentration, and values were expressed as pmoles/mL. The assay was highly specific for cGMP, demonstrating no cross-reactivity with ANP, BNP, CNP, and Endothelin-1, and less than 0.001 percent cross-reactivity with cAMP, GMP, GDP, ATP, and GTP.

Figure 21:
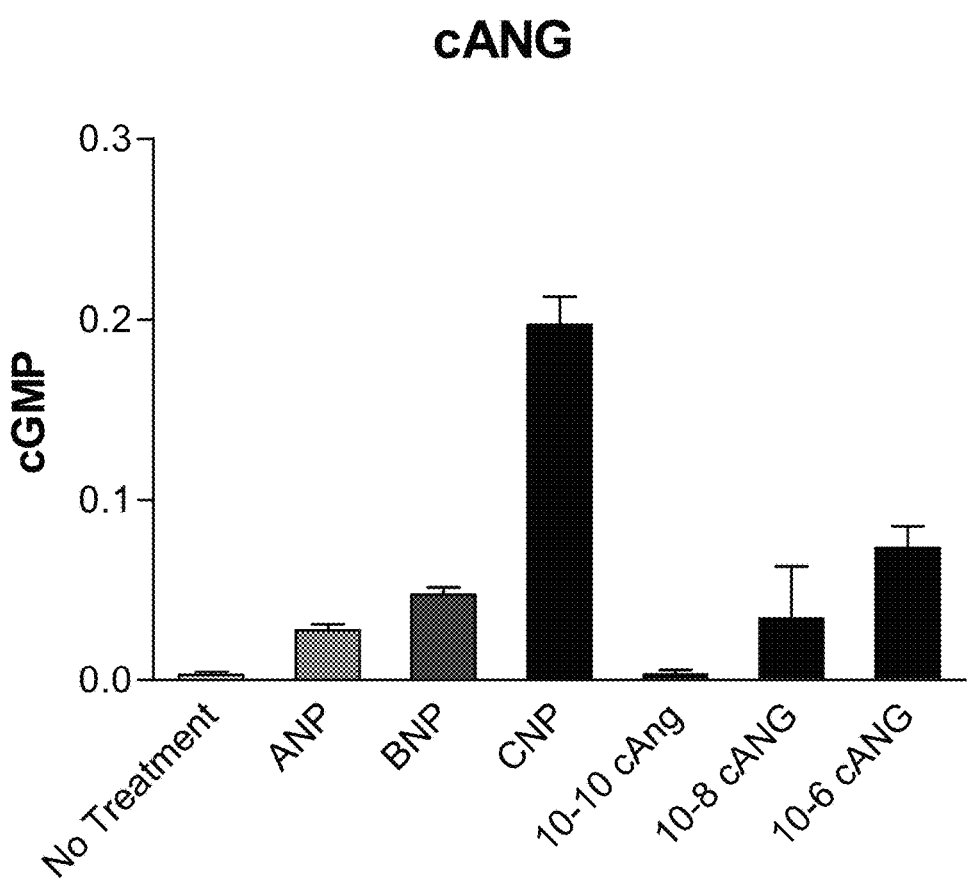
FIG. 21 is a graph plotting the level of cGMP (pmol/mL) produced by human cardiac fibroblasts when exposed to ANP ($10^{-6}$M), BNP ($10^{-6}$M), CNP ($10^{-6}$M), or cANG ($10^{-6}$, $10^{-8}$, or $10^{-10}$ M).
Figure 22:
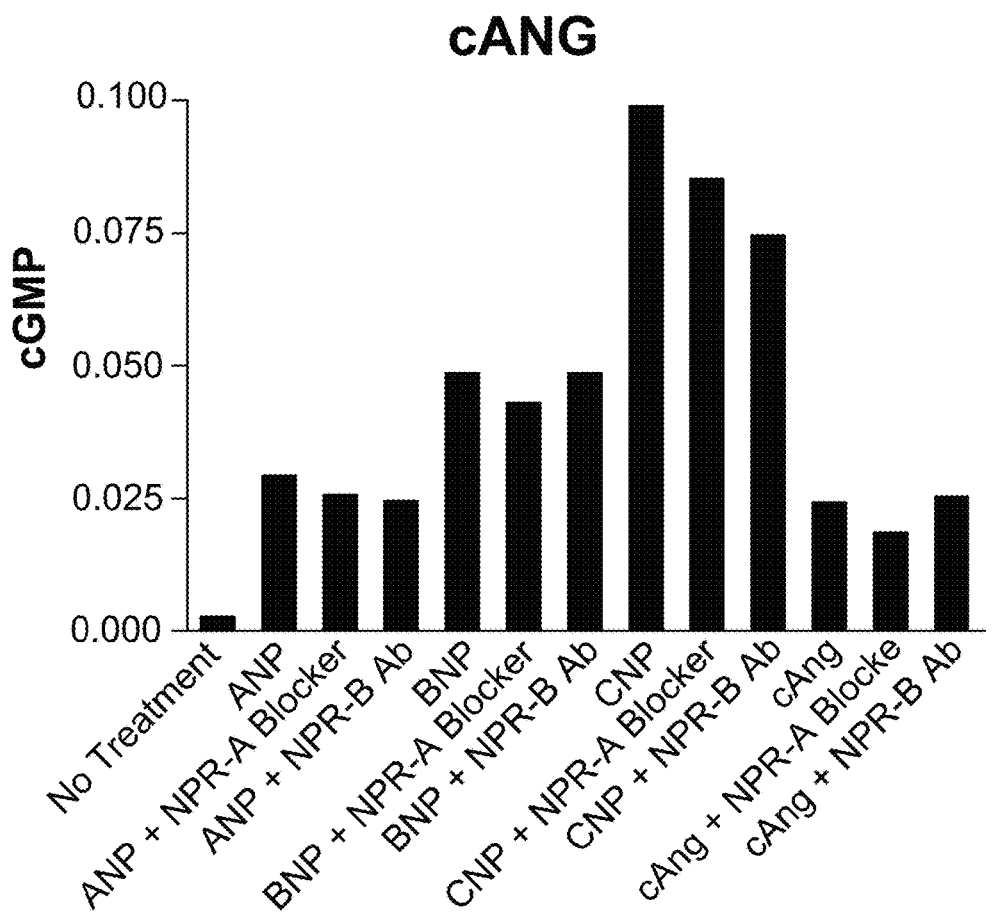
FIG. 22 is a graph plotting the level of cGMP (pmol/mL) produced by human cardiac fibroblasts when exposed to ANP ($10^{-6}$M), BNP ($10^{-6}$M), CNP ($10^{-6}$M), or cANG ($10^{-6}$M) either alone or in the presence of A-71915 (1 µM; an NPR-A blocker (see, e.g., Kumar et al., *Hypertension*, 29(1 Pt 2):414-21 (1997))) or an NPR-B antibody (1:100 dilution).
Figure 23:
FIG. 23 is a structural schematic of a chimeric polypeptide (SEQ ID NO:27) containing an N-terminal Ang-(1-7) and the C-terminus of ANP ($ANP_{C-term}$) without a ring structure in accordance with some embodiments. This polypeptide can be referred to as Ang-(1-7)-ANP-CT.
Figure 24:
FIG. 24 is a structural schematic of a chimeric polypeptide (SEQ ID NO:28) containing an N-terminal Ang-(1-7) and the C-terminus of BNP ($BNP_{C-term}$) without a ring structure in accordance with some embodiments. This polypeptide can be referred to as Ang-(1-7)-BNP-CT.
Figure 25:
FIG. 25 is a structural schematic of a chimeric polypeptide (SEQ ID NO:29) containing an N-terminal Ang-(1-7) and the C-terminus of DNP ($DNP_{C-term}$) without a ring structure in accordance with some embodiments. This polypeptide can be referred to as Ang-(1-7)-DNP-CT. The amino acid sequence of the C-terminal segment of DNP shown in FIG. 25 (PSLRDPRPNAPSTSA; SEQ ID NO:30) can be referred to as $DNP_{C-term}$.
Figure 26:
FIG. 26 is a structural schematic of a chimeric polypeptide (SEQ ID NO:31) containing the C-terminus of ANP ($ANP_{C-term}$) as an N-terminal segment followed by a C-terminal Ang-(1-7) without a ring structure in accordance with some embodiments. This polypeptide can be referred to as ANP-CT-Ang-(1-7).
Figure 27:
FIG. 27 is a structural schematic of a chimeric polypeptide (SEQ ID NO:32) containing the C-terminus of BNP ($BNP_{C-term}$) as an N-terminal segment followed by a C-terminal Ang-(1-7) without a ring structure in accordance with some embodiments. This polypeptide can be referred to as BNP-CT-Ang-(1-7).
Figure 28:
FIG. 28 is a structural schematic of a chimeric polypeptide (SEQ ID NO:33) containing the C-terminus of DNP ($DNP_{C-term}$) as an N-terminal segment followed by a C-terminal Ang-(1-7) without a ring structure in accordance with some embodiments. This polypeptide can be referred to as DNP-CT-Ang-(1-7).
Figure 29:
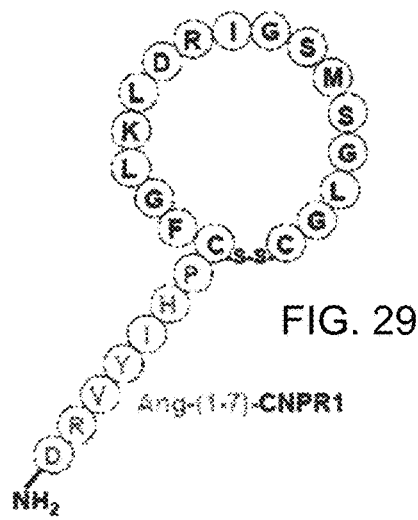
FIG. 29 is a structural schematic of a chimeric polypeptide (SEQ ID NO:34) containing an N-terminal Ang-(1-7) and a ring structure ($CNP_{ring}$) with no C-terminal tail in accordance with some embodiments. This polypeptide can be referred to as Ang-(1-7)-CNPR1.
Figure 30:
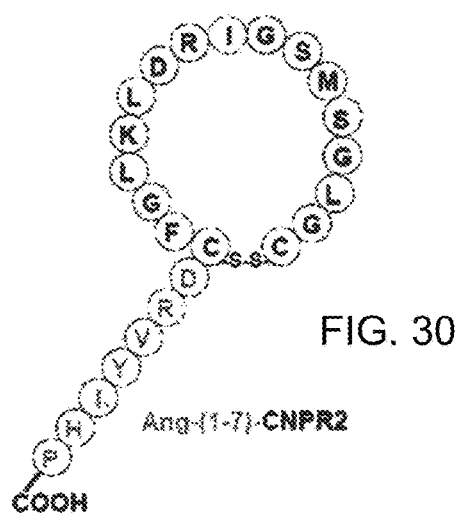
FIG. 30 is a structural schematic of a chimeric polypeptide (SEQ ID NO:35) containing a reverse ring structure of CNP and an C-terminal Ang-(1-7) and with no N-terminal tail in accordance with some embodiments. This polypeptide can be referred to as Ang-(1-7)-CNPR2. The amino acid sequence of the reverse ring structure segment of CNP shown in FIG. 30 (CGLGSMSGIRDLKLGFC; SEQ ID NO:36) can be referred to as reverse-$CNP_{ring}$.
Figure 31:
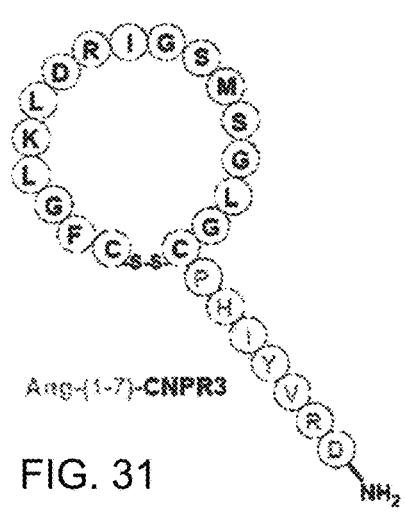
FIG. 31 is a structural schematic of a chimeric polypeptide (SEQ ID NO:37) containing an N-terminal Ang-(1-7) and a reverse ring structure (reverse-$CNP_{ring}$) with no C-terminal tail in accordance with some embodiments. This polypeptide can be referred to as Ang-(1-7)-CNPR3.
Figure 32:
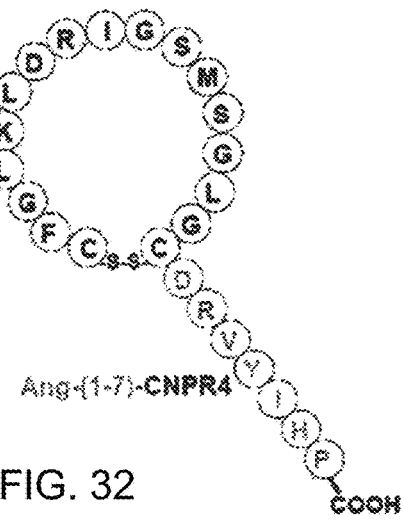
FIG. 32 is a structural schematic of a chimeric polypeptide (SEQ ID NO:38) containing a ring structure ($CNP_{ring}$) and an C-terminal Ang-(1-7) and with no N-terminal tail in accordance with some embodiments. This polypeptide can be referred to as Ang-(1-7)-CNPR4.

Like the treatment of CFs with ANP, BNP, and CNP, treatment of CFs with cANG resulted in cGMP production (FIGS. 20 and 21). These results demonstrate that addition of Ang1-7 does not interfere with receptor binding and cGMP generation.

Example 2—BNP-Ang1-7 and Ang1-7BNP Induce cGMP Production

BNP-Ang1-7 and Ang1-7BNP were synthesized to have the sequence set forth in FIG. 3 and FIG. 20, respectively.

HEK 293 cells were stably transfected to express either NPR-A (GC-A) or NPR-B (GC-B) using Lipofectamine (Invitrogen, Grand Island, N.Y.). Transfected cells were maintained in Dulbecco's modified Eagle's medium supplemented with 10% fetal bovine serum, 100 U/mL penicillin, 100 U/mL streptomycin, and 250 µg/mL G418. The reagents were obtained from Invitrogen (Grand Island, N.Y.).

The following was performed to carry out cell stimulation and cGMP assays. Cells were plated in 6-well plates and treated as described elsewhere (Tsuruda et al., *Circulation Research*, 91:1127-1134 (2002)). Briefly, cells were incubated in Hank's balanced salt solution (Invitrogen, Carlsbad, Calif.) containing 20 mmol/L N-[2-hydroxyethyl]piperazine-N'[2-ethanesulfonic acid], 0.1% bovine serum albumin, and 0.5 mmol/L 3-isobutyl-1-methylzanthine (Sigma, St. Louis, Mo.). Treated cells received $10^{-10}$ M, $10^{-8}$ M, or $10^{-6}$ M of either BNP-Ang1-7 or Ang1-7BNP for 10 minutes. Cells were lysed in 300 µL 6% TCA and sonicated for 10 minutes. The samples were ether extracted four times in 4 volumes of ether, dried, and reconstituted in 500 µL cGMP assay buffer. The samples were assayed using a competitive RIA cGMP kit (Perkin-Elmer, Boston, Mass.) as described elsewhere (Steiner et al., *J. Biol. Chem.*, 247:1106-1113 (1972)). Samples were corrected for dilution factors and protein concentration, and values were expressed as pmol cGMP/well. There was no cross-reactivity with ANP, BNP, CNP, and Endothelin-1, and less than 0.001 percent cross-reactivity with cAMP, GMP, GDP, ATP, and GTP.

Figure 33:
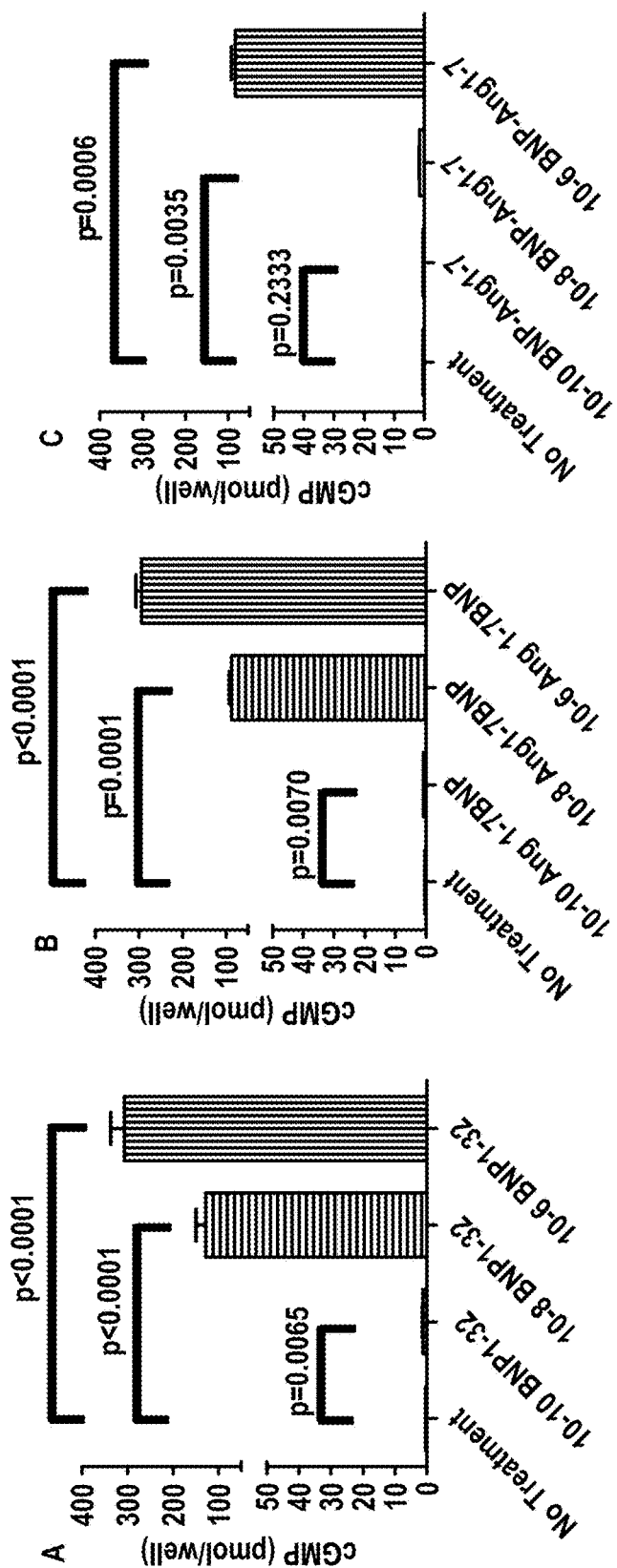
FIG. 33 contains graphs plotting cGMP levels resulting from treatment of HEK 293 cells with the indicated amount ($10^{-6}$, $10^{-8}$, or $10^{-10}$ M) of BNP (BNP1-32.
Figure 34:
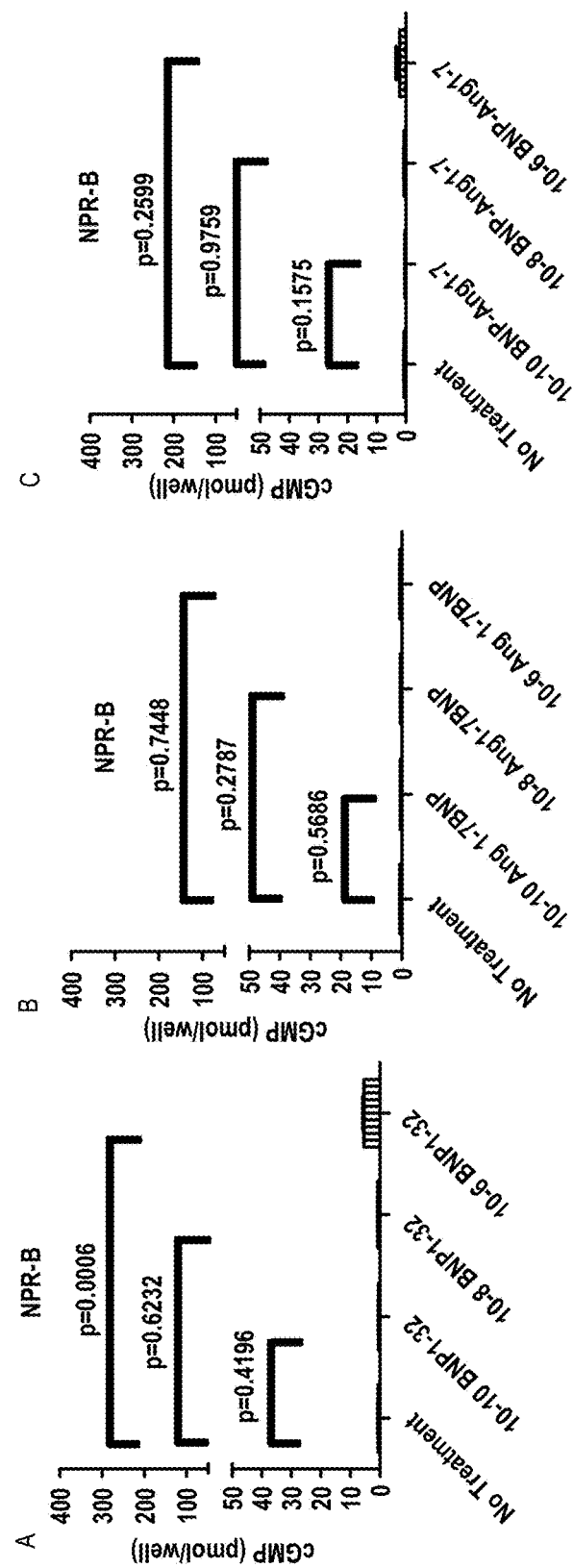
FIG. 34 contains graphs plotting cGMP levels resulting from treatment of HEK 293 cells with the indicated amount ($10^{-6}$, $10^{-8}$, or $10^{-10}$ M) of BNP (BNP1-32.
Figure 35:
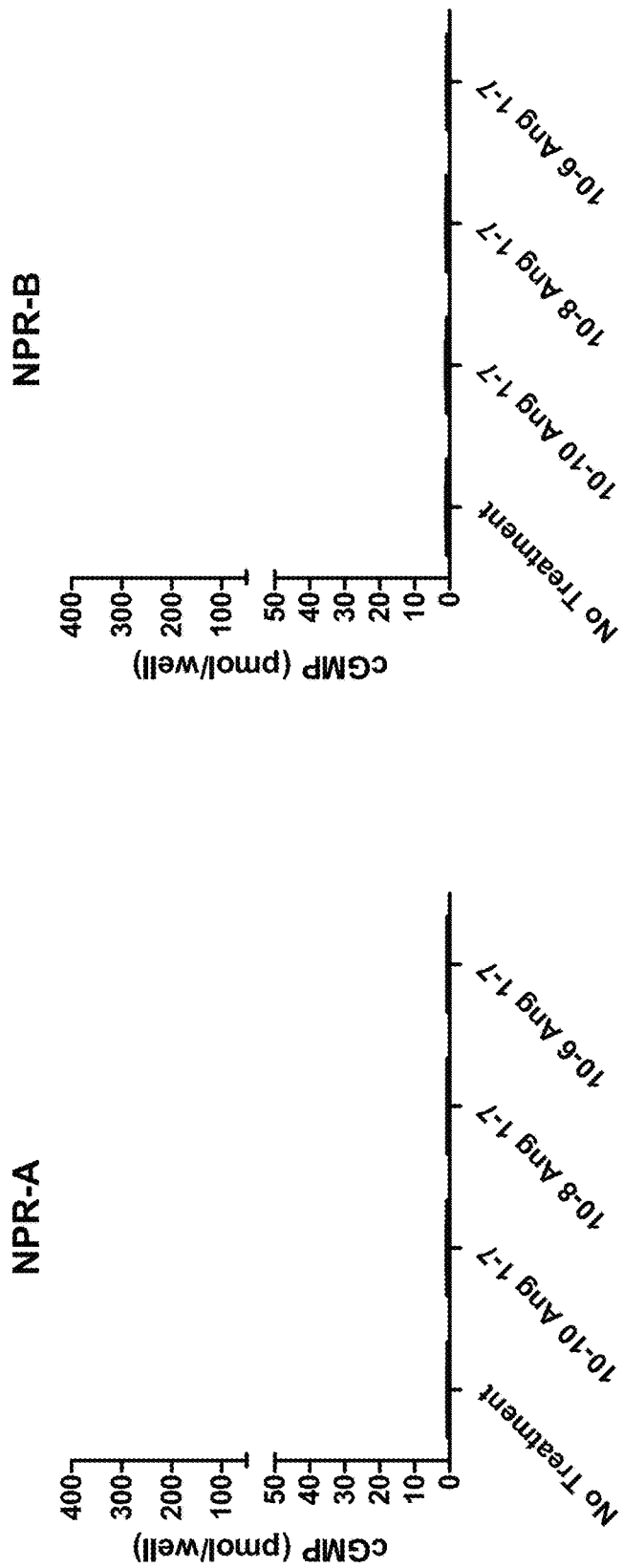
FIG. 35 contains graphs plotting cGMP levels resulting from treatment of HEK 293 cells with the indicated amount ($10^{-6}$, $10^{-8}$, or $10^{-10}$ M) of Ang1-7. The HEK 293 cells were stably transfected to express NPR-A (i.e., GC-A) (left graph) or NPR-B (i.e., GC-B) (right graph).

Like BNP (FIG. 33A), exposure of NPR-A⁺ HEK 293 cells to either BNP-Ang1-7 or Ang1-7BNP induced cGMP production (FIGS. 33B and 33C). Neither BNP-Ang1-7 nor Ang1-7BNP induced cGMP production in NPR-B⁺ HEK 293 cells (FIGS. 34B and 34C). Minimal cGMP production was observed for NPR-B⁺ HEK 293 cells exposed to BNP (FIG. 34A). Ang1-7 did not induce cGMP production when placed in contact with NPR-A⁺ HEK 293 cells (FIG. 35, left panel) or NPR-B⁺ HEK 293 cells (FIG. 35, right panel).

These results demonstrate that both BNP-Ang1-7 and Ang1-7BNP induce cGMP production. These results also demonstrate that attaching Ang1-7 to a natriuretic polypeptide or a component of a natriuretic polypeptide (e.g., a ring structure of a natriuretic polypeptide) in either an N-terminal location or a C-terminal location does not interfere with the ability of the natriuretic polypeptide or the natriuretic polypeptide component to bind to its natriuretic polypeptide receptor and induce cGMP production.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric polypeptide comprising, in an order from amino terminus to carboxy terminus:
   (a) the sequence set forth in SEQ ID NO:1 or the sequence set forth in SEQ ID NO:1 with two or less additions, deletions, or substitutions,
   (b) the sequence set forth in SEQ ID NO:7, the sequence set forth in SEQ ID NO:7 with no more than two additions, deletions, or substitutions, the sequence set forth in SEQ ID NO:9, or the sequence set forth in SEQ ID NO:9 with no more than two additions, deletions, or substitutions, and
   (c) the sequence set forth in SEQ ID NO:30 or the sequence set forth in SEQ ID NO:30 with no more than two additions, deletions, or substitutions.

2. The polypeptide of claim 1, wherein said polypeptide comprises the sequence set forth in SEQ ID NO:1.

3. The polypeptide of claim 1, wherein said polypeptide comprises the sequence set forth in SEQ ID NO:1 with one addition, deletion, or substitution.

4. The polypeptide of claim 1, wherein said polypeptide comprises the sequence set forth in SEQ ID NO:1 with two additions, deletions, or substitutions.

5. The polypeptide of claim 1, wherein said polypeptide comprises the sequence set forth in SEQ ID NO:7.

6. The polypeptide of claim 1, wherein said polypeptide comprises the sequence set forth in SEQ ID NO:7 with one addition, deletion, or substitution.

7. The polypeptide of claim 1, wherein said polypeptide comprises the sequence set forth in SEQ ID NO:7 with two additions, deletions, or substitutions.

8. The polypeptide of claim 1, wherein said polypeptide comprises the sequence set forth in SEQ ID NO:9.

9. The polypeptide of claim 1, wherein said polypeptide comprises the sequence set forth in SEQ ID NO:9 with one addition, deletion, or substitution.

10. The polypeptide of claim 1, wherein said polypeptide comprises the sequence set forth in SEQ ID NO:9 with two additions, deletions, or substitutions.

11. The polypeptide of claim 1, wherein said polypeptide comprises the sequence set forth in SEQ ID NO:30.

12. The polypeptide of claim 1, wherein said polypeptide comprises the sequence set forth in SEQ ID NO:30 with one addition, deletion, or substitution.

13. The polypeptide of claim 1, wherein said polypeptide comprises the sequence set forth in SEQ ID NO:30 with two additions, deletions, or substitutions.

* * * * *